(12) United States Patent
Brown et al.

(10) Patent No.: US 7,498,358 B2
(45) Date of Patent: Mar. 3, 2009

(54) HUMAN ADAM-10 INHIBITORS

(75) Inventors: S. David Brown, San Carlos, CA (US);
Lynne Canne-Bannen, Pacifica, CA (US); Erick Wang Co, Redwood City, CA (US); Vasu Jammalamadaka, Pleasonton, CA (US); Rickard George Khoury, Redwood City, CA (US); Moon Hwan Kim, Palo Alto, CA (US); Donna T. Le, San Jose, CA (US); Amy Lew Tsuhako, Milpitas, CA (US); Morrison B. Mac, San Francisco, CA (US); Shumeye Mamo, Oakland, CA (US); John M. Nuss, Danville, CA (US); Michael P. Prisbylla, Pleasant Hill, CA (US); Wei Xu, Danville, CA (US)

(73) Assignee: Exelixis, Inc., South San Francisco, CA (US)

( * ) Notice: Subject to any disclaimer, the term of this patent is extended or adjusted under 35 U.S.C. 154(b) by 391 days.

(21) Appl. No.: 10/498,338

(22) PCT Filed: Dec. 13, 2002

(86) PCT No.: PCT/US02/39816

§ 371 (c)(1),
(2), (4) Date: May 11, 2005

(87) PCT Pub. No.: WO03/051825

PCT Pub. Date: Jun. 26, 2003

(65) Prior Publication Data

US 2005/0227973 A1    Oct. 13, 2005

Related U.S. Application Data

(60) Provisional application No. 60/340,179, filed on Dec. 14, 2001.

(51) Int. Cl.
| | |
|---|---|
| *C07C 311/19* | (2006.01) |
| *C07C 311/29* | (2006.01) |
| *C07C 259/06* | (2006.01) |
| *C07C 259/08* | (2006.01) |
| *C07D 213/32* | (2006.01) |
| *C07D 213/68* | (2006.01) |
| *A61K 31/16* | (2006.01) |
| *A61K 31/44* | (2006.01) |
| *A61P 19/02* | (2006.01) |
| *A61P 35/00* | (2006.01) |
| *A61P 9/10* | (2006.01) |

(52) U.S. Cl. .................. 514/507; 562/621; 562/623; 564/80; 560/12; 546/272.1; 546/283.4; 514/351; 514/357; 514/518; 514/562

(58) Field of Classification Search ............... 562/621; 564/80; 514/507
See application file for complete search history.

(56) References Cited

U.S. PATENT DOCUMENTS

| | | | |
|---|---|---|---|
| 5,985,900 | A | 11/1999 | Bender et al. |
| 6,423,729 | B1 | 7/2002 | Kurihara et al. |

FOREIGN PATENT DOCUMENTS

| | | |
|---|---|---|
| EP | 1 029 541 A | 8/2000 |
| JP | 11 246527 A | 9/1999 |
| WO | WO99/42443 | 8/1999 |
| WO | 00/15213 A | 3/2000 |

OTHER PUBLICATIONS

Gough et al., Immunol., 172(6), 3678-3685, 2004.*
Lendeckel et al., J. Can. Res. Clin. Oncol., 131, 41-48, 2005.*

* cited by examiner

*Primary Examiner*—Venkataraman Balasubramanian

(57) ABSTRACT

The present invention provides compounds useful for inhibiting the ADAM-10 protein. Such compounds are useful in the in vitro study of the role of ADAM-10 (and its inhibition) in biological processes. The present invention also comprises pharmaceutical compositions comprising one or more ADAM-10 inhibitors according to the invention in combination with a pharmaceutically acceptable carrier. Such compositions are useful for the treatment of cancer, arthritis, and diseases related to angiogenesis. Correspondingly, the invention also comprises methods of treating forms of cancer, arthritis, and diseases related to angiogenesis in which ADAM-10 plays a critical role. The invention also provides methods for making bis-aryl ether sulfonyl chlorides and ADAM-10 modulators therefrom.

27 Claims, No Drawings

HUMAN ADAM-10 INHIBITORS

This application is a 371 of PCT/US02/39816, filed Dec. 13, 2002 which claims benefit of U.S. Provisional Application No. 60/340,179, filed Dec. 14, 2001.

BACKGROUND OF THE INVENTION

1. Field of the Invention

The present invention is in the field of agents that inhibit human ADAM-10 (also known as human Kuzbanian) and their use in the treatment of cancer, arthritis, and diseases related to angiogenesis, such as renal diseases, heart diseases such as heart failure, atherosclerosis, and stroke, inflammation, ulcer, infertility, scleroderma, endometriosis, mesothelioma, and diabetes.

2. Summary of the Related Art

Cell-cell interactions play an important role in regulating cell fate decisions and pattern formation during the development of multicellular organisms. One of the evolutionarily conserved pathways that plays a central role in local cell interactions is mediated by the transmembrane receptors encoded by the Notch (N) gene of *Drosophila*, the lin-12 and glp-1 genes of *C. elegans*, and their vertebrate homologs (reviewed in Artavanis-Tsakonas, S., et al. (1995) Notch Signaling. Science 268, 225-232), collectively hereinafter referred to as NOTCH receptors. Several lines of evidence suggest that the proteolytic processing of NOTCH receptors is important for their function. For example, in addition to the full length proteins, antibodies against the intracellular domains of NOTCH receptors have detected C-terminal fragments of 100-120 kd; see, e.g., Fehon, R. G., et al. (1990). Cell 61, 523-534; Crittenden, S. L., et al. (1994). Development 120, 2901-2911; Aster, J., et al. (1994) Cold Spring Harbor Symp. Quant. Biol. 59, 125-136; Zagouras, P., et al. (1995). Proc. Natl. Acad. Sci. U.S.A. 92, 6414-6418; and Kopan, R., et al. (1996). Proc. Natl. Acad. Sci. U.S.A. 93, 1683-1688. However, the mechanism(s) of NOTCH activation have been hitherto largely unknown.

During neurogenesis, a single neural precursor is singled out from a group of equivalent cells through a lateral inhibition process in which the emerging neural precursor cell prevents its neighbors from taking on the same fate (reviewed in Simpson, P. (1990). Development 109, 509-519). Genetic studies in *Drosophila* have implicated a group of "neurogenic genes" including N in lateral inhibition. Loss-of-function mutations in any of the neurogenic genes result in hypertrophy of neural cells at the expense of epidermis (reviewed in Campos-Ortega, J. A. (1993) In: The Development of *Drosophila melanogaster* M. Bate and A. Martinez-Arias, eds. pp. 1091-1129. Cold Spring Harbor Press.).

Rooke, J., Pan, D. J., Xu, T. and Rubin, G. M. (1996). Science 273, 1227-1231, discloses neurogenic gene family, kuzbanian (kuz). Members of the KUZ family of proteins are shown to belong to the recently defined ADAM family of transmembrane proteins, members of which contain both a disintegrin and metalloprotease domain (reviewed in Wolfsberg, T. G. et al., (1995). J. Cell Biol. 131, 275-278, see also Blobel, C. P., et al. (1992). Nature 356, 248-252, 1992; Yagami-Hiromasa, T., et al. (1995). Nature 377, 652-656; Black, R. A., et al. (1997). Nature 385, 729-733, 1997; and Moss, M. L., et al. (1997). Nature 385, 733-736; see also U.S. Pat. No. 5,922,546 and U.S. Pat. No. 5,935,792).

Genes of the ADAM family encode transmembrane proteins containing both metalloprotease and disintegrin domains (reviewed in Black and White, 1998 Curr. Opin. Cell Biol. 10, 654-659; Wolfsberg and White, 1996 Dev. Biol. 180, 389-401), and are involved in diverse biological processes in mammals such as fertilization (Cho et al., 1998 Science 281, 1857-1859), myoblast fusion (Yagami-Hiromasa et al., 1995 Nature 377, 652-656) and ectodomain shedding (Moss et al., 1997 Nature 385, 733-736; Black et al., 1997 Nature 385, 729-733; Peschon et al., 1998 Science 282, 1281-1284). The *Drosophila* kuzbanian (kuz) gene represents the first ADAM family member identified in invertebrates (Rooke et al., 1996 Science 273, 1227-1231). Previous genetic studies showed that kuz is required for lateral inhibition and axonal outgrowth during *Drosophila* neural development (Rooke et al., 1996; Fambrough et al., 1996 PNAS. USA 93, 13233-13238; Pan and Rubin, 1997 Cell 90, 271-280; Sotillos et al., 1997 Development 124, 4769-4779). Specifically, during the lateral inhibition process, kuz acts upstream of Notch (Pan and Rubin, 1997; Sotillos et al., 1997), which encodes the transmembrane receptor for the lateral inhibition signal encoded by the Delta gene. More recently, a homolog of kuz was identified in *C. elegans* (SUP-17) that modulates the activity of a *C. elegans* homolog of Notch in a similar manner (Wen et al., 1997 Development 124, 4759-4767).

Vertebrate homologs of kuz have been isolated in *Xenopus*, bovine, mouse, rat and human. The bovine homolog of KUZ (also called MADM or ADAM 10) was initially isolated serendipitously based on its in vitro proteolytic activity on myelin basic protein, a cytoplasmic protein that is unlikely the physiological substrate for the bovine KUZ protease (Howard et al., 1996 Biochem. J. 317, 45-50). Expression of a dominant negative form of the murine kuz homolog (mkuz) in *Xenopus* leads to the generation of extra neurons, suggesting an evolutionarily conserved role for mkuz in regulating Notch signaling in vertebrate neurogenesis (Pan and Rubin, 1997). U.S. patent application. No. 09/697,854, to Pan et al., filed Oct. 27, 2000, discloses that mkuz mutant mice die around embryonic day (E) 9.5, with severe defects in the nervous system, the paraxial mesoderm and the yolk sac vasculature. In the nervous system, mkuz mutant embryos show ectopic neuronal differentiation. In the paraxial mesoderm, mkuz mutant embryos show delayed and uncoordinated segmentation of the somites. These phenotypes are similar to those of mice lacking Notch-1 or components of the Notch pathway such as RBP-Jk (Conlon et al, 1995, Development 121, 1533-1545; Oka et al., 1995), indicating a conserved role for mkuz in modulating Notch signaling in mouse development. Furthermore, no visible defect was detected in Notch processing in the kuz knockout animals. In addition to the neurogenesis and somitogenesis defect, mkuz mutant mice also show severe defects in the yolk sac vasculature, with an enlarged and disordered capillary plexus and the absence of large vitelline vessels. Since such phenotype has not been observed in mice lacking Notch-1 or RBP-Jk (Swiatek et al., 1994 Genes Dev 15, 707-719; Conlon et al., 1995; Oka et al., 1995 Development 121, 3291-3301), Pan et al. determined that this phenotype reveals a novel function of mkuz that is distinct from its role in modulating Notch signaling, specifically, that kuz plays an essential role for an ADAM family disintegrin metalloprotease in mammalian angiogenesis.

In view of the important role of KUZ (ADAM-10) in biological processes and disease states, inhibitors of this protein are desirable.

All patents, applications, and publications recited herein are hereby incorporated by reference in their entirety.

SUMMARY OF THE INVENTION

The present invention provides compounds useful for inhibiting or otherwise modulating the activity of the ADAM-10 protein. Such compounds are useful in the in vitro study of the role of ADAM-10 (and its inhibition) in biological processes. The present invention also comprises pharmaceutical compositions comprising one or more ADAM-10 inhibitors according to the invention in combination with a pharmaceutically acceptable carrier. Such compositions are useful for the treatment of cancer, arthritis, and diseases related to angiogenesis. Correspondingly, the invention also comprises methods of treating forms of cancer, arthritis, and diseases related to angiogenesis in which ADAM-10 plays a critical role.

DETAILED DESCRIPTION OF THE INVENTION

The present invention comprises inhibitors of ADAM-10. In Aspect A, the invention comprises a compound of structural formula I:

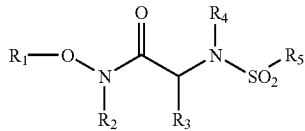

I or a pharmaceutically acceptable salt thereof, wherein
$R_1$ is selected from hydrogen, alkyl, alkanoyl, arylalkyl, and arylalkanoyl, wherein the arylalkyl and arylalkanoyl groups are unsubstituted or substituted with 1, 2, 3, 4, or 5 $R_6$ groups;
$R_6$ at each occurrence is independently selected from halogen, hydroxy, —$NO_2$, —$CO_2R_{10}$, —CN, alkyl, alkoxy, haloalkyl, and haloalkoxy;
$R_2$ is selected from hydrogen, alkyl, alkoxy, alkanoyl, arylalkyl and arylalkanoyl, wherein
  the arylalkyl and arylalkanoyl groups are unsubstituted or substituted with 1, 2, 3, 4, or 5 $R_6$ groups;
$R_3$ is —Z—Q—J, wherein
  Z is selected from alkyl, alkoxyalkyl, alkylthioalkyl, and alkenyl, each of which is unsubstituted or substituted with 1 or 2 groups that are independently selected from alkoxy, hydroxy, and halogen;
  Q is selected from a direct bond between Z and J, C(=O)—, aryl, heteroaryl, and heterocycloalkyl, wherein
    the aryl, heteroaryl, or heterocycloalkyl group is unsubstituted or substituted with 1 or 2 groups that are independently selected from alkyl, halogen, —$NR_8R_9$, and alkoxy;
  J is selected from —$NR_8R_9$, —$NR_7C(=O)NR_8R_9$, —$NR_7C(=O)$alkyl$NR_8R_9$, —$NR_7C(=O)OR_9$, —$C(=NR_7)NR_8R_9$, and —NH—$C(=NR_7)NR_8R_8$, wherein
    $R_7$ is selected from H, CN, $NO_2$, alkyl, alkanoyl, arylalkanoyl and —$C(=O)NR_{10}R_{11}$, wherein
      $R_{10}$ and $R_{11}$ are independently selected from H, and alkyl, and
    $R_8$ and $R_9$ are independently selected from H, alkyl, hydroxy, alkoxy, alkoxyalkyl, heterocycloalkylalkyl, arylalkyl, and heteroarylalkyl, wherein each of the above is unsubstituted or substituted with 1, 2, 3, or 4 $R_6$ groups; or
    $R_8$ and $R_9$ and the nitrogen to which they are attached form a 5, 6 or 7 membered heterocycloalkyl ring, which is unsubstituted or substituted with 1, 2, or 3 groups that are independently selected from alkyl, alkoxy, hydroxy, and halogen;
  or
    $R_7$, $R_8$, and the nitrogens to which they are attached form a 5, 6 or 7 membered heterocycloalkyl group that is unsubstituted or substituted with 1, 2 or 3 groups that are independently selected from alkyl, alkoxy, hydroxy, and halogen; and
    $R_9$ is selected from H, alkyl, hydroxy, alkoxy, alkoxyalkyl, heterocycloalkylalkyl, arylalkyl, and heteroarylalkyl, wherein each of the above is unsubstituted or substituted with 1, 2, 3, or 4 $R_6$ groups;
$R_4$ is selected from H, alkyl, and arylalkyl, wherein the arylalkyl group is unsubstituted or substituted with 1, 2, 3, 4, or 5 $R_6$ groups; and
$R_5$ is —M—G—A, wherein
M is selected from aryl and heteroaryl, wherein M is unsubstituted or substituted with 1, 2, 3, or 4 groups that are independently selected from halogen, alkyl, hydroxy, alkoxy, haloalkyl, —CN, haloalkoxy, and hydroxyalkyl;
G is selected from a direct bond between M and A, $CH_2$, -alkyl-O—, —O-alkyl-, O, S, SO, and $SO_2$;
A is selected from aryl and heteroaryl, wherein A is unsubstituted or substituted with 1, 2, 3, 4, or 5 groups that are independently selected from halogen, alkyl, alkoxy, haloalkyl, aryloxy, heteroaryloxy, arylalkoxy, heteroarylalkoxy, haloalkoxy, —CN, and $NO_2$;
with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl;

In embodiment 1 of Aspect A, the invention comprises a compound of formula I as described in Aspect A, wherein
$R_1$ is selected from the group consisting of hydrogen, $C_1$-$C_6$ alkyl, phenyl $C_1$-$C_6$ alkyl, and phenyl $C_1$-$C_6$ alkanoyl, wherein the phenylalkyl and phenylalkanoyl groups are unsubstituted or substituted with 1, 2, 3, 4, or 5 $R_6$ groups, and
$R_2$ is selected from the group consisting of hydrogen, $C_1$-$C_6$ alkyl, $C_1$-$C_6$ alkanoyl, phenyl $C_1$-$C_6$ alkyl and phenyl $C_1$-$C_6$ alkanoyl, wherein the phenylalkyl and phenylalkanoyl groups are unsubstituted or substituted with 1, 2, 3, 4, or 5 $R_6$ groups,
wherein $R_6$ at each occurrence is independently selected from the group consisting of halogen, hydroxy, —$NO_2$, —CN, $C_1$-$C_6$ alkyl, $C_1$-$C_6$ alkoxy, $CF_3$, and $OCF_3$.

In embodiment 2 of Aspect A, the invention comprises a compound of formula I as described in Aspect A, wherein
$R_3$ is —Z—Q—J, wherein
Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 groups independently selected from $C_1$-$C_4$ alkyl, halogen, and $C_1$-$C_4$ alkoxy;
Q is a direct bond between Z and J, —C(=Ok, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently selected from $C_1$-$C_4$ alkyl, halogen, and $C_1$-$C_4$ alkoxy;

J is —C(=NR$_7$)NR$_8$R$_9$ or —NH—C(=NR$_7$)NR$_8$R$_9$, wherein

R$_7$ is selected from the group consisting of H, —CN, —NO$_2$, $C_1$-$C_6$ alkyl, $C_1$-$C_6$ alkanoyl, phenyl $C_1$-$C_6$ alkanoyl and —C(=O)NR$_{10}$R$_{11}$, wherein R$_{10}$ and R$_{11}$ are independently selected from H and $C_1$-$C_6$ alkyl, R$_8$ and R$_9$ are each independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 R$_6$ groups; or R$_8$ and R$_9$ and the nitrogen to which they are attached form a 5, 6 or 7 membered heterocycloalkyl ring, which is unsubstituted or substituted with 1, 2, or 3 groups that are independently selected from $C_1$-$C_6$ alkyl, $C_{1-6}$ alkoxy, hydroxy, and halogen;

or

R$_7$, R$_8$, and the nitrogens to which they are attached form a 5, 6 or 7 membered heterocycloalkyl group that is unsubstituted or substituted with 1, 2 or 3 groups that are independently selected from $C_1$-$C_6$ alkyl, $C_1$-$C_6$ alkoxy, hydroxy, and halogen; and R$_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, thiomorpholinyl S-oxide, phenyl, naphthyl, thiomorpholinyl S,S-dioxide, pyrrolidinyl, pyridyl, pyridazyl, pyrimidyl, pyrazinyl, and imidazolyl, wherein each of the above is unsubstituted or substituted with 1, 2, 3, or 4 R$_6$ groups, wherein R$_6$ at each occurrence is independently selected from the group consisting of halogen, hydroxy, NO$_2$, $C_1$-$C_6$ alkyl, $C_1$-$C_6$ alkoxy, CF$_3$, and OCF$_3$.

In embodiment 3 of Aspect A, the invention comprises a compound of formula I as described in Aspect A, wherein R$_5$ is —M—G—A, wherein M is selected from the group consisting of phenyl, pyridyl, pyrimidyl, pyridazinyl, pyrazinyl, thiophenyl, and pyrrolyl, wherein M is unsubstituted or substituted with 1, 2, 3, or 4 groups that are independently selected from the group consisting of halogen, $C_1$-$C_6$ alkyl, hydroxy, $C_1$-$C_6$ alkoxy, halo $C_1$-$C_6$ alkyl, halo $C_1$-$C_6$ alkoxy, and hydroxy $C_1$-$C_6$ alkyl, G is selected from a direct bond between M and A, CH$_2$, O, S, SO, and SO$_2$;

A is selected from the group consisting of phenyl, naphthyl, pyridyl, pyrimidyl, pyridazyl, pyrazinyl, pyrrolyl, benzo[1,3]dioxyl, quinolinyl, isoquinolinyl, tetrahydroisoquinolinyl, tetrahydronaphthyl, and dihydronaphthyl, wherein each of the above is unsubstituted or substituted with 1, 2, 3, 4, or 5 groups that are independently selected from halogen, $C_1$-$C_6$ alkyl, $C_1$-$C_6$ alkoxy, halo $C_1$-$C_6$ alkyl, halo $C_1$-$C_6$ alkoxy, CN, and NO$_2$;

with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl.

In embodiment 4 of Aspect A, the invention comprises a compound of formula I as described in Aspect A, wherein R$_1$ is hydrogen, $C_1$-$C_6$ alkyl or benzyl;

R$_2$ is hydrogen, $C_1$-$C_6$ alkyl or benzyl; and

R$_3$ is —Z—Q—J, wherein

Z is $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy;

Q is a direct bond between Z and J, —C(=O)—, piperidinyl, pyrrolyl, piperazinyl, imidazolidinyl, morpholinyl, thiomorpholinyl, azepanyl, or azocanyl wherein each of the above is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ or —NH—C(=NR$_7$)NR$_8$R$_9$, wherein

R$_7$ is selected from the group consisting of H, —CN, —NO$_2$, $C_1$-$C_6$ alkyl, $C_1$-$C_6$ alkanoyl, phenyl $C_1$-$C_6$ alkanoyl and —C(=O)NR$_{10}$R$_{11}$, wherein R$_{10}$ and R$_{11}$ are independently H, or $C_1$-$C_6$ alkyl, and R$_8$ and R$_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 R$_6$ groups; or R$_8$ and R$_9$ and the nitrogen to which they are attached form a 5, 6 or 7 membered heterocycloalkyl ring, which is unsubstituted or substituted with 1, 2, or 3 groups that are independently selected from $C_1$-$C_6$ alkyl, $C_1$-$C_6$ alkoxy, hydroxy, and halogen;

or

R$_7$, R$_8$, and the nitrogens to which they are attached form a 5, 6, or 7 membered heterocycloalkyl group that is unsubstituted or substituted with 1, 2 or 3 groups that are independently selected from $C_1$-$C_6$ alkyl, $C_1$-$C_6$ alkoxy, hydroxy, and halogen, wherein each of the above is unsubstituted or substituted with 1, 2, 3, or 4 R$_6$ groups, wherein R$_6$ at each occurrence is independently selected from the group consisting of halogen, hydroxy, NO$_2$, $C_1$-$C_6$ alkyl, $C_1$-$C_6$ alkoxy, CF$_3$, and OCF$_3$; and R$_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, thiomorpholinyl S-oxide, phenyl, naphthyl, thiomorpholinyl S,S-dioxide, pyrrolidinyl, pyridyl, pyridazyl, pyrimidyl, pyrazinyl, and imidazolyl, wherein each of the above is unsubstituted or substituted with 1, 2, 3, or 4 R$_6$ groups;

R$_4$ is selected from the group consisting of H, $C_1$-$C_4$ alkyl, benzyl and phenethyl, wherein the benzyl and phenethyl groups are unsubstituted or substituted with 1, 2, 3, or 4 R$_6$ groups;

$R_5$ is —M—G—A, wherein
  M is selected from the group consisting of phenyl, pyridyl, pyrimidyl, pyridazinyl, pyrazinyl, thiophenyl, and pyrrolyl, wherein M is unsubstituted or substituted with 1, 2, 3, or 4 groups that are independently selected from the group consisting of halogen, $C_1$-$C_6$ alkyl, hydroxy, $C_1$-$C_6$ alkoxy, halo $C_1$-$C_6$ alkyl, halo $C_1$-$C_6$ alkoxy, and hydroxy $C_1$-$C_6$ alkyl,
  G is selected from a direct bond between M and A, $CH_2$, O, S, SO, and $SO_2$;
  A is selected from the group consisting of phenyl, naphthyl, pyridyl, pyrimidyl, pyridazyl, pyrazinyl, pyrrolyl, benzo[1,3]dioxyl, quinolinyl, isoquinolinyl, tetrahydroisoquinolinyl, tetrahydronaphthyl, and dihydronaphthyl, wherein each of the above is unsubstituted or substituted with 1, 2, 3, 4, or 5 groups that are independently halogen, $C_1$-$C_6$ alkyl, $C_1$-$C_6$ alkoxy, halo $C_1$-$C_6$ alkyl, halo $C_1$-$C_6$ alkoxy, CN, or $NO_2$;
  with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl.

In embodiment 5 of Aspect A, the invention comprises a compound as in embodiment 4 of Aspect A, wherein
$R_5$ is —M—G—A, wherein
  M is phenyl, pyridyl, pyrimidyl, pyridazinyl, pyrazinyl, thiophenyl, and pyrrolyl, each of which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;
  G is selected from a direct bond between M and A, $CH_2$, O, S, SO, and $SO_2$;
  A is selected from the group consisting of phenyl, naphthyl, pyridyl, pyrimidyl, pyrrolyl, benzo[1,3]dioxyl, quinolinyl, isoquinolinyl, tetrahydroisoquinolinyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, —CN, and —$NO_2$;
  with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl.

In embodiment 6 of Aspect A, the invention comprises a compound as in embodiment 5 of Aspect A, wherein
$R_3$ is —Z—Q—J, wherein
Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;
Q is a direct bond between Z and J, —C(=O)—, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein
  $R_7$ is selected from the group consisting of H, CN, $NO_2$, $C_1$-$C_6$ alkyl, $C_1$-$C_6$ alkanoyl, and —C(=O)$NR_{10}R_{11}$, wherein
    $R_{10}$ and $R_{11}$ are independently H, or $C_1$-$C_6$ alkyl, and
  $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups; wherein
    $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$;
  or
  $R_8$ and $R_9$ and the nitrogen to which they are attached form a 5 or 6 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

In embodiment 7 of Aspect A, the invention comprises a compound as in embodiment 6 of Aspect A, wherein
$R_3$ is —Z—Q—J, wherein
Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;
Q is piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy; and
J is —C(=$NR_7$)$NR_8R_9$, wherein
  $R_7$ is selected from the group consisting of H, CN, $NO_2$, $C_1$-$C_6$ alkyl, $C_1$-$C_6$ alkanoyl, and —C(=O)$NR_{10}R_{11}$, wherein
    $R_{10}$ and $R_{11}$ are independently H, or $C_1$-$C_6$ alkyl, and
  $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups, wherein
    $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$;
  or
  $R_8$ and $R_9$ and the nitrogen to which they are attached form a 5 or 6 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

In embodiment 8 of Aspect A, the invention comprises a compound as in embodiment 7 of Aspect A, wherein
$R_8$ and $R_9$ and the nitrogen to which they are attached form a morpholinyl, thiomorpholinyl, piperazinyl, piperidinyl or pyrrolidinyl ring, each of which is unsubstituted or substituted with 1, 2, or 3 groups that are independently $C_1$-$C_6$ alkyl, $C_1$-$C_6$ alkoxy, hydroxy, or halogen.

In embodiment 9 of Aspect A, the invention comprises a compound as in embodiment 5 of Aspect A, wherein $R_3$ is —Z—Q—J wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ or —NH—C(=NR$_7$)NR$_8$R$_9$, wherein $R_7$, $R_8$, and the nitrogens to which they are attached form a 5, 6, or 7 membered heterocycloalkyl group that is unsubstituted or substituted with 1, or 2 groups that are independently $C_1$-$C_6$ alkyl, $C_1$-$C_6$ alkoxy, hydroxy, or halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, phenyl, naphthyl, pyrrolidinyl, pyridyl, pyridazyl, and imidazolyl, wherein each of the above is unsubstituted or substituted with 1, or 2 $R_6$ groups; wherein $R_6$ at each occurrence is independently selected from the group consisting of halogen, hydroxy, NO$_2$, $C_1$-$C_6$ alkyl, $C_1$-$C_6$ alkoxy, CF$_3$, and OCF$_3$.

In embodiment 10 of Aspect A, the invention comprises a compound as in embodiment 5 of Aspect A, wherein $R_3$ is —Z—Q—J wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy; and J is —C(=NR$_7$)NR$_8$R$_9$ or —NH—C(=NR$_7$)NR$_8$R$_9$, wherein $R_7$ is selected from the group consisting of H, CN, NO$_2$, $C_1$-$C_6$ alkyl, $C_1$-$C_6$ alkanoyl, and —C(=O)NR$_{10}$R$_{11}$, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups; wherein $R_6$ at each occurrence is independently selected from the group consisting of halogen, hydroxy, NO$_2$, $C_1$-$C_6$ alkyl, $C_1$-$C_6$ alkoxy, CF$_3$, and OCF$_3$.

In Aspect B, the invention comprises a compound as in Aspect A of structural formula II

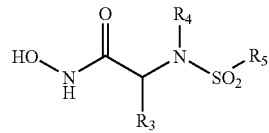

II wherein $R_3$, $R_4$, and $R_5$ are as defined in Aspect A.

In embodiment 1 of Aspect B, the invention comprises a compound as described in Aspect B, wherein $R_4$ is selected from the group consisting of H, $C_1$-$C_4$ alkyl, and benzyl wherein the benzyl group is unsubstituted or substituted with 1, 2, 3, or 4 $R_6$ groups, wherein $R_6$ at each occurrence is independently selected from the group consisting of halogen, hydroxy, —NO$_2$, $C_1$-$C_6$ alkyl, $C_1$-$C_6$ alkoxy, CF$_3$, and OCF$_3$.

In embodiment 2 of Aspect B, the invention comprises a compound as embodiment 1 of Aspect B, wherein $R_5$ is —M—G—A, wherein M is phenyl, pyridyl, pyrimidyl, pyridazinyl, pyrazinyl, thiophenyl, and pyrrolyl, each of which is unsubstituted or substituted with 1, 2, or 3 groups that are independently selected from the group consisting of F, Cl, Br, $C_1$-$C_4$ alkyl, hydroxy, methoxy, ethoxy, isopropoxy, CF$_3$, OCF$_3$, halo $C_1$-$C_4$ alkyl, halo $C_1$-$C_4$ alkoxy, and hydroxy $C_1$-$C_4$ alkyl;

G is selected from a direct bond between M and A, CH$_2$, O, S, SO, and SO$_2$;

A is selected from the group consisting of phenyl, naphthyl, pyridyl, pyrimidyl, pyrrolyl, benzo[1,3]dioxyl, quinolinyl, isoquinolinyl, tetrahydroisoquinolinyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, CF$_3$, OCF$_3$, CN, and NO$_2$;

with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl.

In embodiment 3 of Aspect B, the invention comprises a compound as in embodiment 1 of Aspect B, wherein $R_3$ is —Z—Q—J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)k, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ or —NH—C(=NR$_7$)NR$_8$R$_9$, wherein $R_7$ is selected from the group consisting of H, CN, NO$_2$, $C_1$-$C_6$ alkyl, $C_1$-$C_6$ alkanoyl, phenyl $C_1$-$C_6$ alkanoyl and —C(=O)NR$_{10}$R$_{11}$, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen, wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

In Aspect C, the invention comprises a compound as in Aspect B of structural formula III

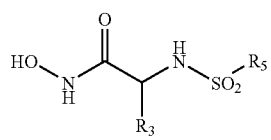

III wherein $R_3$ is —Z—Q—J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ or —NH—C(=NR$_7$)NR$_8$R$_9$, wherein $R_7$ is selected from the group consisting of H, CN, $NO_2$, $C_1$-$C_6$ alkyl, $C_1$-$C_6$ alkanoyl, phenyl $C_1$-$C_6$ alkanoyl and —C(=O)NR$_{10}$R$_{11}$, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen; wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$;

and $R_5$ is —M—G—A, wherein

M is phenyl, pyridyl, pyrimidyl, pyridazinyl, pyrazinyl, thiophenyl, and pyrrolyl, each of which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;

G is selected from a direct bond between M and A, $CH_2$, O, S, SO, and $SO_2$; and A is selected from the group consisting of phenyl, naphthyl, pyridyl, pyrimidyl, pyrrolyl, benzo[1,3]dioxyl, quinolinyl, isoquinolinyl, tetrahydroisoquinolinyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$;

with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl.

In embodiment 1 of Aspect C, the invention comprises a compound as described in Aspect C, wherein $R_3$ is —Z—Q—J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ or —NH—C(=NR$_7$)NR$_8$R$_9$, wherein $R_7$ is selected from the group consisting of H, CN, $NO_2$, $C_1$-$C_6$ alkyl, $C_1$-$C_6$ alkanoyl, and —C(=O)NR$_{10}$R$_{11}$, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, piperidinyl $C_1$-$C_6$ alkyl, pyrrolidinyl $C_1$-$C_6$ alkyl, $C_3$-$C_8$ cycloalkyl, $C_3$-$C_8$ cycloalkyl $C_1$-$C_6$ alkyl, benzyl, phenethyl, and pyridyl $C_1$-$C_6$ alkyl, pyridazyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen;

wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$; and $R_5$ is —M—G—A, wherein M is phenyl, pyridyl, pyrimidyl, pyridazinyl, pyrazinyl, thiophenyl, and pyrrolyl, each of which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;

G is selected from a direct bond between M and A, $CH_2$, and O; and

A is selected from the group consisting of phenyl, naphthyl, pyridyl, tetrahydronaphthyl, benzo[1,3]dioxyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$;

with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl.

In Aspect D, the invention comprises a compound as in embodiment 1 of Aspect C of structural formula IV

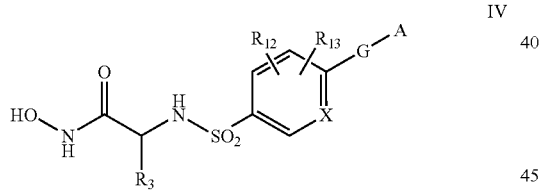

IV wherein $R_3$ is defined in embodiment 1 of Aspect C, and

X is CH, $CR_{12}$, or N;

$R_{12}$ and $R_{13}$ are at each occurrence are independently selected from the group consisting of H, halogen, $CF_3$, $C_1$-$C_4$ alkyl, and $C_1$-$C_4$ alkoxy;

A is selected from the group consisting of phenyl, naphthyl, pyridyl, benzo[1,3]dioxyl, and tetrahydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$; and G is selected from a direct bond between M and A, $CH_2$, and O;

with the proviso that when M is phenyl (in this case when X is equivalent to CH), G is a direct bond between M and A, and A is phenyl, then at least one of $R_{12}$ and $R_{13}$ cannot be H.

In Aspect E, the invention comprises a compound as described in Aspect D of structural formula V

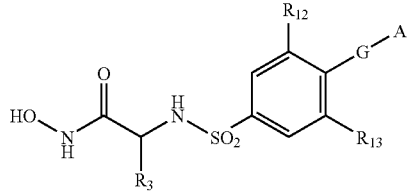

V wherein $R_3$, is as defined in paragraph [0026],

A is phenyl, 3-fluorophenyl, 4-fluorophenyl, 4-chlorophenyl, 4-cyanophenyl, benzo[1,3]dioxyl, 3,5-dimethylphenyl, 2-naphthyl, or 2-tetrahydronaphthyl;

G is a direct bond between M and A, or G is oxygen; and $R_{12}$ and $R_{13}$ are independently H, fluoro, chloro, $CF_3$, methyl or methoxy;

with the proviso that when G is a direct bond to A, and A is phenyl, then at least one of $R_{12}$ and $R_{13}$ cannot be H.

In embodiment 1 of Aspect E, the invention comprises a compounds described in Aspect E, wherein $R_3$ is —Z—Q—J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J or —C(=O)—,

J is —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, and —C(=O)$NR_{10}R_{11}$, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups, wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$, or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

In embodiment 2 of Aspect E, the invention comprises a compound as described in Aspect E, wherein $R_3$ is —Z—Q—J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J or —C(O)—,

J is —NH—C(=$NR_7$)$NR_8R_9$, wherein $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, phenyl, naphthyl, pyrrolidinyl, pyridyl, pyridazyl, pyrimidyl, pyrazinyl, and imidazolyl, wherein each of the above is unsubstituted or substituted with 1, 2, 3, or 4 $R_6$ groups, wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

In embodiment 3 of Aspect E, the invention comprises a compound as described in Aspect E, wherein $R_3$ is —Z—Q—J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ wherein $R_7$ is selected from the group consisting of H, CN, $NO_2$, $C_1$-$C_6$ alkyl, $C_1$-$C_6$ alkanoyl, and —C(=O)$NR_{10}R_{11}$, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

In Aspect F, the invention comprises a compound as described in Aspect D of structural formula VI

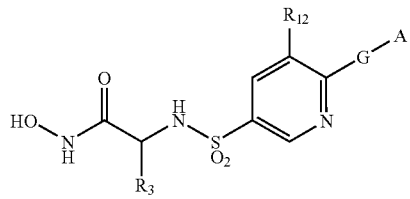

VI wherein $R_3$, is as defined in Aspect D,

A is phenyl, 3-fluorophenyl, 4-fluorophenyl, benzo[1,3]dioxyl, 4-chlorophenyl, 4-cyanophenyl, 3,5-dimethylphenyl, 2-naphthyl, or 2-tetrahydronaphthyl G is a direct bond between M and A, or G is oxygen;

$R_{12}$ is selected from the group consisting of H, halogen, $C_1$-$C_4$ alkyl, —$CF_3$, and $C_1$-$C_4$ alkoxy.

In embodiment 1 of Aspect F, the invention comprises a compound as described in Aspect F, wherein $R_3$ is —Z—Q—J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J or —C(O)—,

J is —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, and —C(=O)$NR_{10}R_{11}$, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$, or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

In embodiment 2 of Aspect F, the invention comprises a compound as described in Aspect F, wherein $R_3$ is —Z—Q—J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J or —C(=O)—,

J is —NH—C(=$NR_7$)$NR_8R_9$, wherein $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, phenyl, naphthyl, pyrrolidinyl, pyridyl, pyridazyl, pyrimidyl, pyrazinyl, and imidazolyl, wherein each of the above is unsubstituted or substituted with 1, 2, 3, or 4 $R_6$ groups, wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

In embodiment 3 of Aspect F, the invention comprises a compound as described in Aspect F, wherein $R_3$ is —Z—Q—J, wherein Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$, wherein
   R$_7$ is selected from the group consisting of H, CN, NO$_2$, C$_1$-C$_6$ alkyl, C$_1$-C$_6$ alkanoyl, and —C(=O)NR$_{10}$R$_{11}$, wherein
      R$_{10}$ and R$_{11}$ are independently H, or C$_1$-C$_6$ alkyl,
   R$_8$ and R$_9$ are independently selected from the group consisting of H, C$_1$-C$_6$ alkyl, hydroxy, C$_1$-C$_6$ alkoxy, alkoxy C$_1$-C$_6$ alkyl, morpholinyl C$_1$-C$_6$ alkyl, C$_3$-C$_8$ cycloalkyl, and C$_3$-C$_8$ cycloalkyl C$_1$-C$_6$ alkyl, wherein each of the above is unsubstituted or substituted with 1, 2, 3, or 4 R$_6$ groups;
   or
   R$_8$ and R$_9$ and the nitrogen to which they are attached form a 5, 6 or 7 membered heterocycloalkyl ring, which is unsubstituted or substituted with 1, 2, or 3 groups that are independently C$_1$-C$_6$ alkyl, C$_1$-C$_6$ alkoxy, hydroxy, or halogen; wherein
      R$_6$ at each occurrence is independently selected from the group consisting of halogen, hydroxy, NO$_2$, C$_1$-C$_6$ alkyl, C$_1$-C$_6$ alkoxy, CF$_3$, and OCF$_3$.

In Aspect G, the invention comprises a compound of structural formula VII:

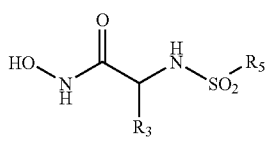

VII wherein
R$_3$ is —Z—Q—J, wherein
   Z is a C$_1$-C$_{10}$ alkyl, C$_1$-C$_6$ alkoxy C$_1$-C$_6$ alkyl, or C$_1$-C$_6$ alkylthio C$_1$-C$_6$ alkyl, each of which is unsubstituted or substituted with 1 or 2 C$_1$-C$_4$ alkyl, halogen, or C$_1$-C$_4$ alkoxy groups;
   Q is a direct bond between Z and J, —C(=O)—, piperidinyl, pyrrolyl, piperazinyl, imidazolidinyl, morpholinyl, thiomorpholinyl, azepanyl, or azocanyl wherein
      each is unsubstituted or substituted with 1 or 2 groups that are independently C$_1$-C$_4$ alkyl, halogen, or C$_1$-C$_4$ alkoxy;
   J is —NH—C(=NR$_7$)NR$_8$R$_9$, wherein
      R$_7$ is selected from the group consisting of H, CN, NO$_2$, C$_1$-C$_6$ alkyl, C$_1$-C$_6$ alkanoyl, phenyl C$_1$-C$_6$ alkanoyl and —C(=O)NR$_{10}$R$_{11}$, wherein
         R$_{10}$ and R$_{11}$ are independently H, or C$_1$-C$_6$ alkyl,
      R$_8$ and R$_9$ are independently selected from the group consisting of H, C$_1$-C$_6$ alkyl, hydroxy, C$_1$-C$_6$ alkoxy, alkoxy C$_1$-C$_6$ alkyl, morpholinyl C$_1$-C$_6$ alkyl, thiomorpholinyl, thiomorpholinyl S,S-dioxide, thiomorpholinyl S-oxide, piperidinyl C$_1$-C$_6$ alkyl, pyrrolidinyl C$_1$-C$_6$ alkyl, imidazolidinyl C$_1$-C$_6$ alkyl, C$_3$-C$_8$ cycloalkyl, C$_3$-C$_8$ cycloalkyl C$_1$-C$_6$ alkyl, phenyl C$_1$-C$_6$ alkyl, and pyridyl C$_1$-C$_6$ alkyl, pyridazyl C$_1$-C$_6$ alkyl, pyrimidyl C$_1$-C$_6$ alkyl, pyrazinyl C$_1$-C$_6$ alkyl, thienyl C$_1$-C$_6$ alkyl, and furyl C$_1$-C$_6$ alkyl, wherein each of the above is unsubstituted or substituted with 1, 2, 3, or 4 R$_6$ groups; or
      R$_8$ and R$_9$ and the nitrogen to which they are attached form a 5, 6 or 7 membered heterocycloalkyl ring, which is unsubstituted or substituted with 1, 2, or 3 groups that are independently C$_1$-C$_6$ alkyl, C$_1$-C$_6$ alkoxy, hydroxy, or halogen; or
      R$_7$, R$_8$, and the nitrogens to which they are attached form a 5, 6, or 7 membered heterocycloalkyl group that is unsubstituted or substituted with 1, 2 or 3 groups that are independently C$_1$-C$_6$ alkyl, C$_1$-C$_6$ alkoxy, hydroxy, or halogen; wherein each of the above is unsubstituted or substituted with 1, 2, 3, or 4 R$_6$ groups; wherein
         R$_6$ at each occurrence is independently selected from the group consisting of halogen, hydroxy, NO$_2$, C$_1$-C$_6$ alkyl, C$_1$-C$_6$ alkoxy, CF$_3$, and OCF$_3$;

and

R$_5$ is —M—G—A, wherein
M is phenyl, pyridyl, pyrimidyl, pyridazinyl, pyrazinyl, thiophenyl, and pyrrolyl, each of which is substituted with 1, 2, or 3 groups that are independently selected from the group consisting of F, Cl, Br, C$_1$-C$_4$ alkyl, hydroxy, methoxy, ethoxy, isopropoxy, CF$_3$, OCF$_3$, halo C$_1$-C$_4$ alkyl, halo C$_1$-C$_4$ alkoxy, and hydroxy C$_1$-C$_4$ alkyl;
G is selected from a direct bond between M and A, and O; and
A is selected from the group consisting of phenyl, naphthyl, pyridyl, pyrimidyl, pyrrolyl, benzo[1,3]dioxyl, quinolinyl, isoquinolinyl, tetrahydroisoquinolinyl, tetrahydronaphthyl, and dihydronaphthyl, wherein each is unsubstituted or substituted with 1, 2, or 3 groups that are independently selected from the group consisting of F, Cl, Br, C$_1$-C$_4$ alkyl, C$_1$-C$_4$ alkoxy, halo C$_1$-C$_4$ alkyl, CF$_3$, OCF$_3$, CN, and NO$_2$;
with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl.

In Aspect H, the invention comprises a compound or pharmaceutically acceptable salt thereof of structural formula VIII:

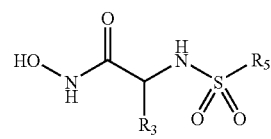

VIII wherein R$_3$ is selected from:

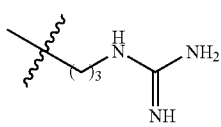

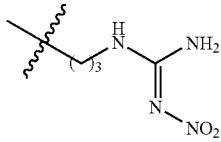

-continued
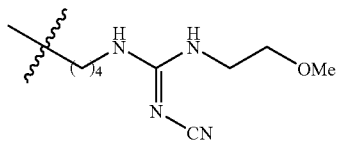
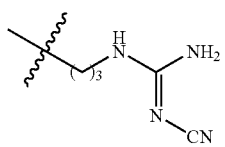
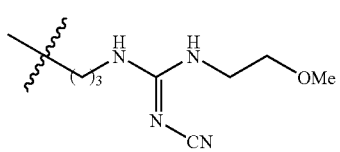
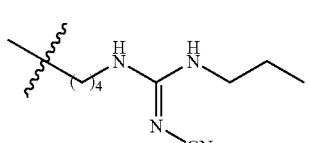
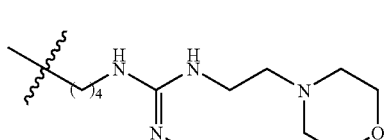
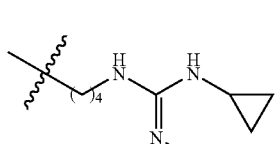
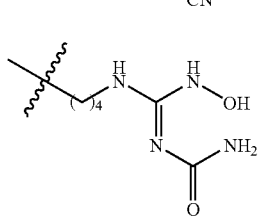
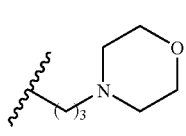
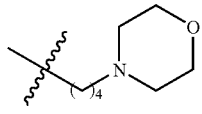
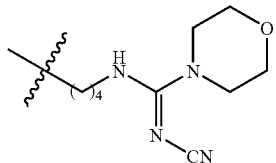
-continued
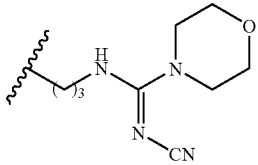
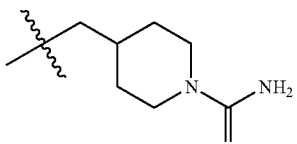
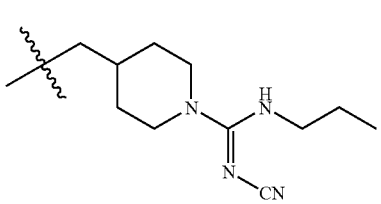
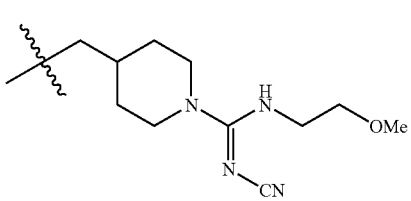
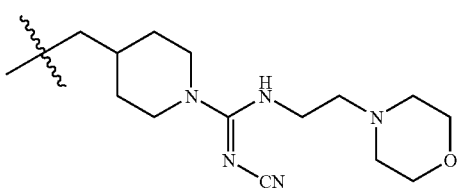
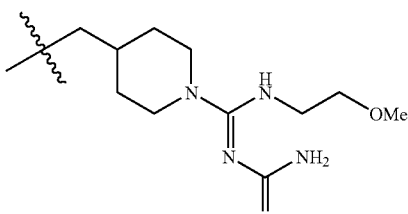
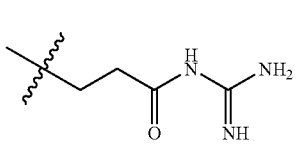
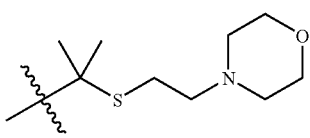
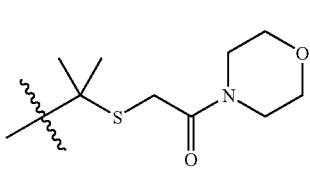

-continued
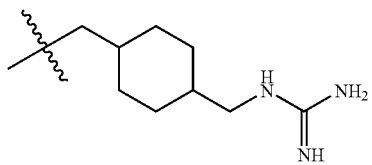
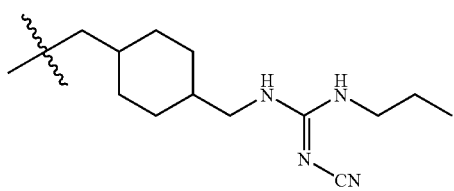
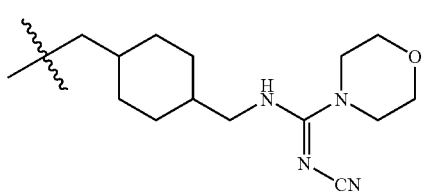
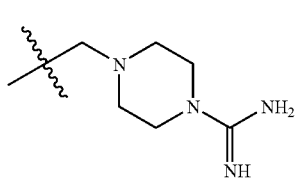
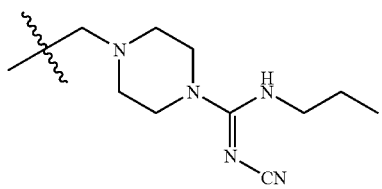
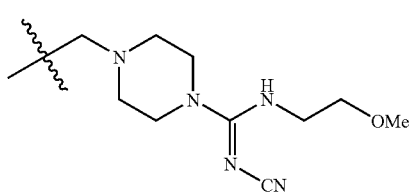
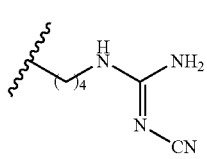
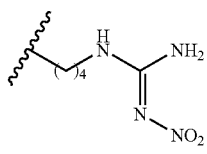
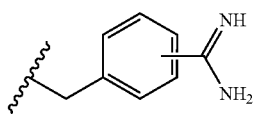
-continued
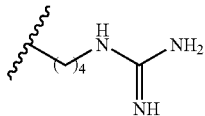
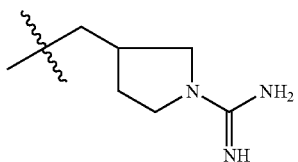
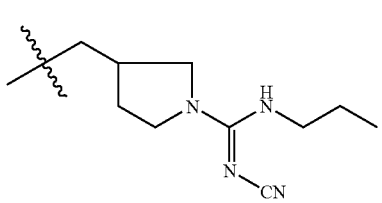
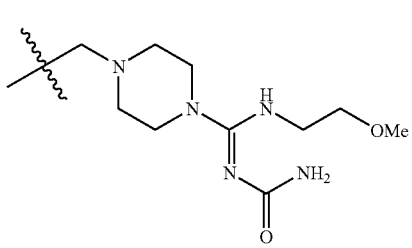
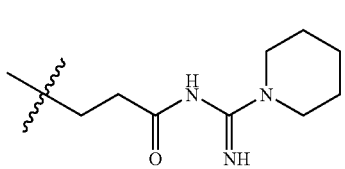
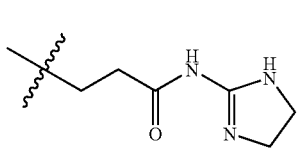
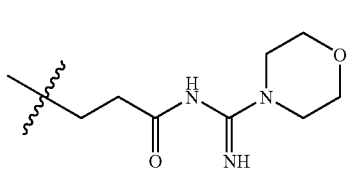
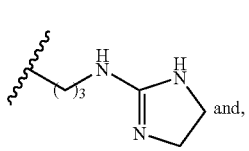 and,
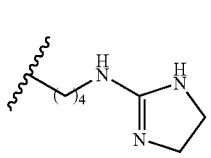

and R$_5$ is selected from
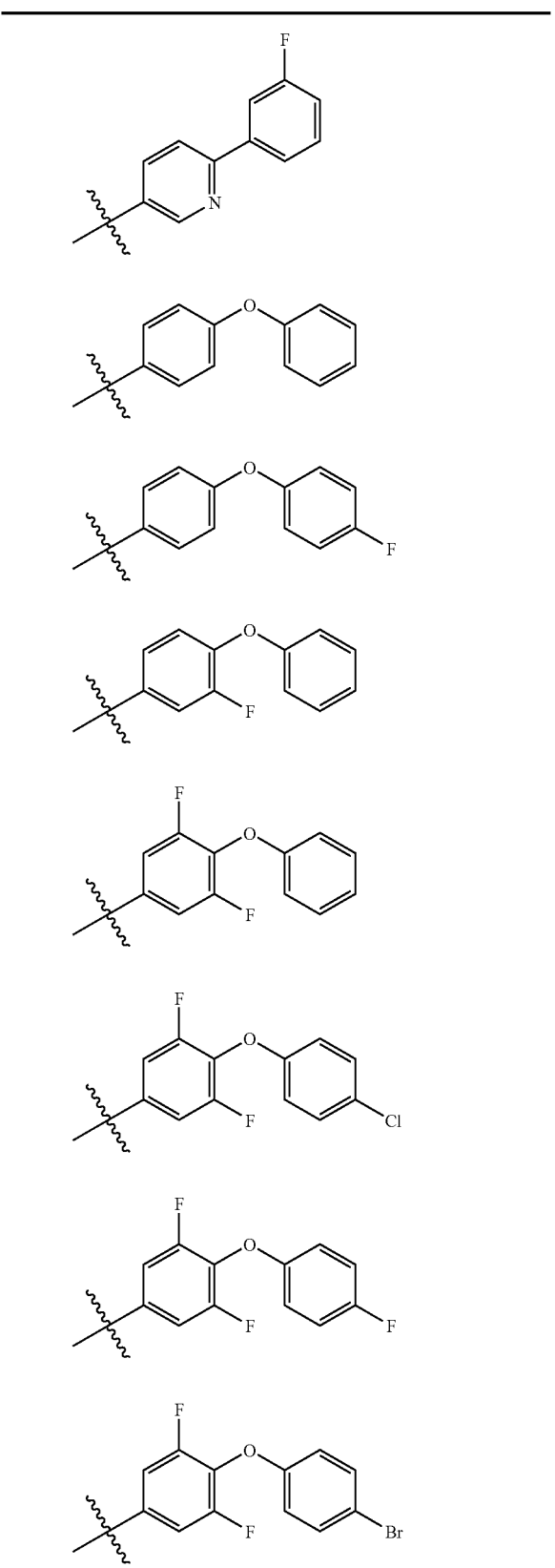
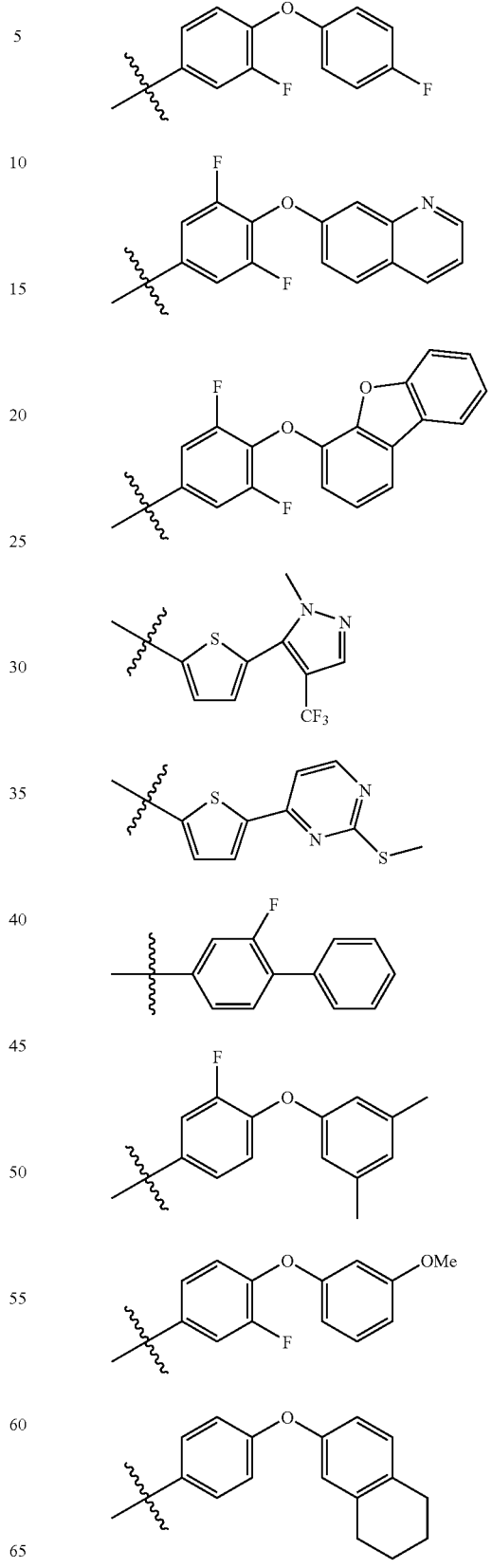

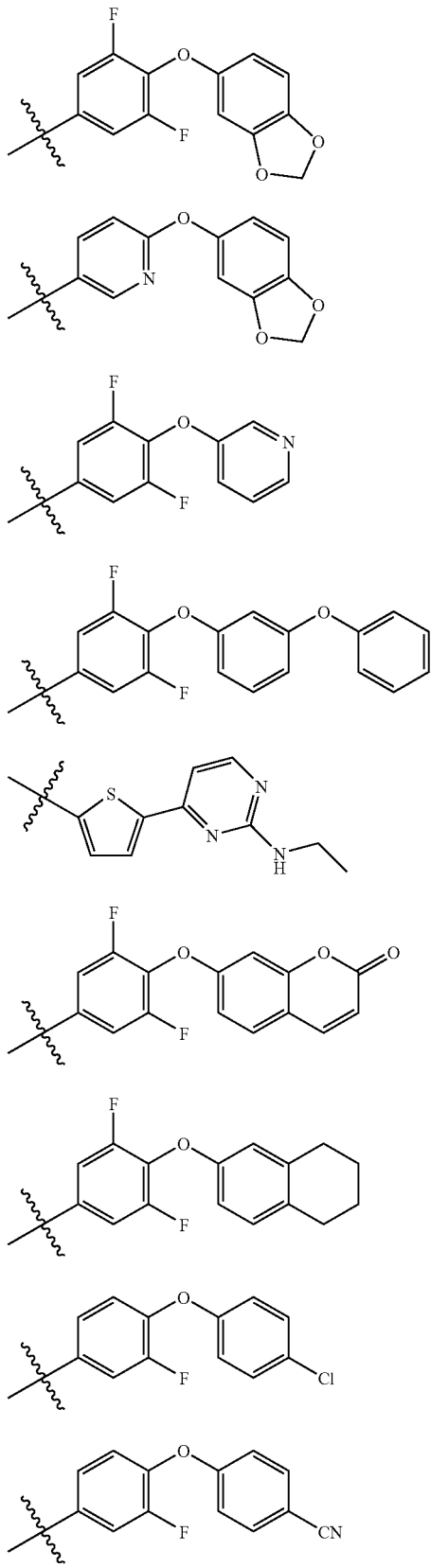
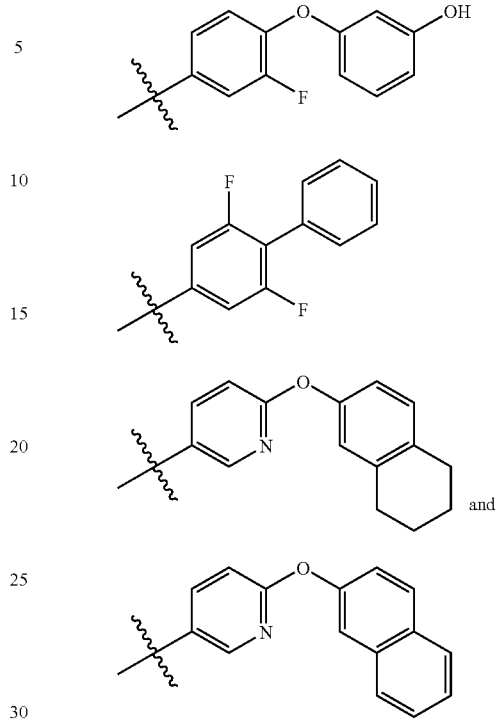

In Aspect J, the invention comprises a compound or pharmaceutically acceptable salt thereof listed in Table 1:

TABLE 1

| # | Compound Name |
|---|---|
| 1 | $N^2$-{[6-(3-fluorophenyl)pyridin-3-yl]sulfonyl}-$N^1$-hydroxy-D-argininamide |
| 2 | $N^1$-hydroxy-$N^2$-[(4-phenoxyphenyl)sulfonyl]-D-argininamide |
| 3 | $N^2$-{[4-(4-fluorophenoxy)phenyl]sulfonyl}-$N^1$-hydroxy-D-argininamide |
| 4 | $N^2$-[(3-fluoro-4-phenoxyphenyl)sulfonyl]-$N^1$-hydroxy-D-argininamide |
| 5 | $N^2$-[(3,5-difluoro-4-phenoxyphenyl)sulfonyl]-$N^1$-hydroxy-D-argininamide |
| 6 | $N^2$-{[4-(4-chlorophenoxy)-3,5-difluorophenyl]sulfonyl}-$N^1$-hydroxy-D-argininamide |
| 7 | $N^2$-{[3,5-difluoro-4-(4-fluorophenoxy)phenyl]sulfonyl}-$N^1$-hydroxy-D-argininamide |
| 8 | $N^2$-{[4-(4-bromophenoxy)-3,5-difluorophenyl]sulfonyl}-$N^1$-hydroxy-D-argininamide |
| 9 | $N^2$-{[3-fluoro-4-(4-fluorophenoxy)phenyl]sulfonyl}-$N^1$-hydroxy-D-argininamide |
| 10 | $N^2$-{[4-(4-chlorophenoxy)-3-fluorophenyl]sulfonyl}-$N^1$-hydroxy-D-argininamide |
| 11 | $N^2$-{[4-(4-cyanophenoxy)-3-fluorophenyl]sulfonyl}-$N^1$-hydroxy-D-argininamide |
| 12 | $N^2$-{[4-(3,5-dimethylphenoxy)-3-fluorophenyl]sulfonyl}-$N^1$-hydroxy-D-argininamide |
| 13 | $N^1$-hydroxy-$N^2$-{[4-(phenyloxy)phenyl]sulfonyl}-D-lysinamide |
| 14 | $N^1$-hydroxy-$N^2$-{[6-(5,6,7,8-tetrahydronaphthalen-2-yloxy)pyridin-3-yl]sulfonyl}-D-argininamide |
| 15 | $N^5$-[(Z)-amino(nitroimino)methyl]-$N^2$-{[6-(3-fluorophenyl)pyridin-3-yl]sulfonyl}-$N^1$-hydroxy-D-ornithinamide |
| 16 | $N^5$-[(Z)-amino(nitroimino)methyl]-$N^1$-hydroxy-$N^2$-[(4-phenoxyphenyl)sulfonyl]-D-ornithinamide |
| 17 | $N^6$-[(E)-amino(cyanoimino)methyl]-$N^2$-{[6-(3-fluorophenyl)pyridin-3-yl]sulfonyl}-$N^1$-hydroxy-D-lysinamide |
| 18 | $N^6$-[(E)-amino(cyanoimino)methyl]-$N^1$-hydroxy-$N^2$-[(4-phenoxyphenyl)sulfonyl]-D-lysinamide |

TABLE 1-continued

| # | Compound Name |
|---|---|
| 19 | $N^6$-{(E)-(cyanoimino)[(2-methoxyethyl)amino]methyl}-$N^2$-{[6-(3-fluorophenyl)pyridin-3-yl]sulfonyl}-$N^1$-hydroxy-D-lysinamide |
| 20 | $N^6$-{(Z)-(cyanoimino)[(2-methoxyethyl)amino]methyl}-$N^1$-hydroxy-$N^2$-[(4-phenoxyphenyl) sulfonyl]-D-lysinamide |
| 21 | $N^6$-{(Z)-(cyanoimino)[(2-methoxyethyl)amino]methyl}-$N^2$-{[4-(4-fluorophenoxy)phenyl] sulfonyl}-$N^1$-hydroxy-D-lysinamide |
| 22 | $N^6$-[(E)-(cyanoimino)(propylamino)methyl]-$N^2$-{[6-(3-fluorophenyl)pyridin-3-yl]sulfonyl}-$N^1$-hydroxy-D-lysinamide |
| 23 | $N^6$-[(E)-(cyanoimino)(propylamino)methyl]-$N^1$-hydroxy-$N^2$-[(4-phenoxyphenyl)sulfonyl]-D-lysinamide |
| 24 | $N^6$-[(E)-(cyanoimino)(propylamino)methyl]-$N^2$-{[4-(4-fluorophenoxy)phenyl]sulfonyl}-$N^1$-hydroxy-D-lysinamide |
| 25 | $N^6$-{(Z)-(cyanoimino)[(2-morpholin-4-ylethyl)amino]methyl}-$N^2$-{[6-(3-fluorophenyl)pyridin-3-yl]sulfonyl}-$N^1$-hydroxy-D-lysinamide |
| 26 | $N^6$-{(Z)-(cyanoimino)[(2-morpholin-4-ylethyl)amino]methyl}-$N^1$-hydroxy-$N^2$-[(4-phenoxyphenyl) sulfonyl]-D-lysinamide |
| 28 | $N^6$-[(Z)-(cyanoimino)(cyclopropylamino)methyl]-$N^1$-hydroxy-$N^2$-[(4-phenoxyphenyl) sulfonyl]-D-lysinamide |
| 29 | $N^6$-[(E)-[(aminocarbonyl)imino](hydroxyamino)methyl]-$N^2$-{[4-(4-fluorophenoxy)phenyl] sulfonyl}-$N^1$-hydroxy-D-lysinamide |
| 30 | $N^1$-hydroxy-5-morpholin-4-yl-$N^2$-[(4-phenoxyphenyl)sulfonyl]-D-norvalinamide |
| 31 | $N^2$-{[4-(4-fluorophenoxy)phenyl]sulfonyl}-$N^1$-hydroxy-5-morpholin-4-yl-D-norvalinamide |
| 32 | $N^2$-{[6-(3-fluorophenyl)pyridin-3-yl]sulfonyl}-$N^1$-hydroxy-6-morpholin-4-yl-D-norleucinamide |
| 33 | $N^1$-hydroxy-6-morpholin-4-yl-$N^2$-[(4-phenoxyphenyl)sulfonyl]-D-norleucinamide |
| 34 | $N^2$-{[4-(4-fluorophenoxy)phenyl]sulfonyl}-$N^1$-hydroxy-6-morpholin-4-yl-D-norleucinamide |
| 35 | $N^2$-[(3-fluoro-4-phenoxyphenyl)sulfonyl]-$N^1$-hydroxy-6-morpholin-4-yl-D-norleucinamide |
| 36 | $N^2$-{[4-(4-chlorophenoxy)-3,5-difluorophenyl]sulfonyl}-$N^1$-hydroxy-6-morpholin-4-yl-D-norleucinamide |
| 37 | $N^2$-{[3,5-difluoro-4-(4-fluorophenoxy)phenyl]sulfonyl}-$N^1$-hydroxy-6-morpholin-4-yl-D-norleucinamide |
| 38 | $N^6$-[(E)-(cyanoimino)(morpholin-4-yl)methyl]-$N^2$-{[4-(4-fluorophenoxy)phenyl]sulfonyl}-$N^1$-hydroxy-D-lysinamide |
| 39 | $N^6$-[(Z)-(cyanoimino)(morpholin-4-yl)methyl]-$N^2$-{[3-fluoro-4-(4-fluorophenoxy)phenyl]sulfonyl}-$N^1$-hydroxy-D-lysinamide |
| 40 | 3-{1-[amino(imino)methyl]piperidin-4-yl}-$N^1$-hydroxy-$N^2$-[(4-phenoxyphenyl)sulfonyl]alaninamide |
| 41 | 3-{1-[(Z)-(cyanoimino)(propylamino)methyl]piperidin-4-yl}-$N^1$-hydroxy-$N^2$-[(4-phenoxyphenyl)sulfonyl]alaninamide |
| 42 | 3-(1-{(Z)-(cyanoimino)[(2-methoxyethyl)amino]methyl}piperidin-4-yl)-$N^1$-hydroxy-$N^2$-[(4-phenoxyphenyl)sulfonyl]alaninamide |
| 43 | 3-(1-{(E)-(cyanoimino)[(2-methoxyethyl)amino]methyl}piperidin-4-yl)-$N^2$-{[3,5-difluoro-4-(4-fluorophenoxy)phenyl]sulfonyl}-$N^1$-hydroxyalaninamide |
| 44 | 3-(1-{(Z)-[(aminocarbonyl)imino][(2-methoxyethyl)amino]methyl}piperidin-4-yl)-$N^1$-hydroxy-$N^2$-[(4-phenoxyphenyl)sulfonyl]alaninamide |
| 45 | $N^2$-{[3,5-difluoro-4-(4-fluorophenoxy)phenyl]sulfonyl}-$N^1$-hydroxy-3-[(2-morpholin-4-ylethyl)thio]-D-valinamide |
| 46 | $N^2$-{[3-fluoro-4-(4-fluorophenoxy)phenyl]sulfonyl}-$N^1$-hydroxy-3-[(2-morpholin-4-ylethyl)thio]-D-valinamide |
| 47 | $N^2$-{[3-fluoro-4-(4-fluorophenoxy)phenyl]sulfonyl}-$N^1$-hydroxy-3-[(2-morpholin-4-yl-2-oxoethyl)thio]-D-valinamide |
| 48 | $N^2$-{[4-(4-chlorophenoxy)-3-fluorophenyl]sulfonyl}-$N^1$-hydroxy-3-[(2-morpholin-4-yl-2-oxoethyl)thio]-D-valinamide |
| 49 | $N^6$-4,5-dihydro-1H-imidazol-2-yl-$N^2$-{[4-(4-fluorophenoxy)phenyl]sulfonyl}-$N^1$-hydroxy-D-lysinamide |
| 50 | $N^6$-[(Z)-(cyanoimino)(cyclopropylamino)methyl]-$N^2$-{[6-(3-fluorophenyl)pyridin-3-yl] sulfonyl}-$N^1$-hydroxy-D-lysinamide |
| 51 | $N^1$-hydroxy-$N^2$-{[4-(phenyloxy)phenyl]sulfonyl}-3-piperidin-3-ylalaninamide |
| 52 | $N^1$-hydroxy-$N^2$-{[4-(phenyloxy)phenyl]sulfonyl}-3-pyrrolidin-3-ylalaninamide |
| 53 | $N^2$-{[6-(3-fluorophenyl)pyridin-3-yl]sulfony}-$N^1$-hydroxy-D-lysinamide |
| 54 | $N^1$-hydroxy-$N^2$-{[4-(phenyloxy)phenyl]sulfonyl}-D-tryptophanamide |
| 55 | $N^1$-hydroxy-$N^2$-({5-[2-(methylthio)pyrimidin-4-yl]-2-thienyl}sulfonyl)lysinamide |
| 56 | $N^1$-hydroxy-$N^2$-{[4-(phenyloxy)phenyl]sulfonyl}-D-histidinamide |
| 57 | $N^1$-hydroxy-$N^2$-methyl-$N^2$-{[4-(phenyloxy)phenyl]sulfonyl}-3-piperidin-3-ylalaninamide |
| 58 | $N^1$-hydroxy-$N^2$-{[4-(phenyloxy)phenyl]sulfonyl}-3-piperidin-4-ylalaninamide |
| 59 | $N^1$-hydroxy-$N^2$-{[4-(phenyloxy)phenyl]sulfonyl}-3-pyridin-3-yl-D-alaninamide |
| 60 | $N^6$-glycyl-$N^1$-hydroxy-$N^2$-{[4-(phenyloxy)phenyl]sulfonyl}-D-lysinamide |
| 61 | $N^1$-hydroxy-$N^2$,$N^6$,$N^6$-trimethyl-$N^2$-{[4-(phenyloxy)phenyl]sulfony}-D-lysinamide |
| 62 | 3-[4-(aminomethyl)cyclohexyl]-$N^1$-hydroxy-$N^2$-{[4-(phenyloxy)phenyl]sulfonyl}alaninamide |
| 63 | $N^1$-hydroxy-$N^2$-{[6-(naphthalen-1-yloxy)pyridin-3-yl]sulfonyl}-D-argininamide |
| 64 | $N^1$-hydroxy-$N^2$-{[6-(5,6,7,8-tetrahydronaphthalen-2-yloxy)pyridin-3-yl]sulfonyl}-D-lysinamide |
| 65 | $N^6$-[(E)-(cyanoimino)(hydroxyamino)methyl]-$N^2$-({4-[(4-fluorophenyl)oxy]phenyl}sulfonyl)-$N^1$-hydroxy-D-lysinamide |
| 66 | $N^2$-({4-[(4-fluorophenyl)oxy]phenyl}sulfonyl)-$N^1$-hydroxy-D-lysinamide |
| 67 | $N^6$-{(Z)-(cyanoimino)[(2-morpholin-4-ylethyl)amino]methyl}-{[6-(3-fluorophenyl)pyridin-3-yl]sulfonyl}-$N^1$-hydroxy-D-lysinamide |
| 68 | $N^2$-({6-[(4-fluorophenyl)oxy]pyridin-3-yl}sulfonyl)-$N^1$-hydxoxy-D-argininamide |
| 69 | $N^2$-({6-[(4-chlorophenyl)oxy]pyridin-3-yl}sulfonyl)-$N^1$-hydroxy-D-argininamide |
| 70 | $N^2$-({3,5-difluoro-4-[(4-fluorophenyl)oxy]phenyl}sulfonyl)-$N^1$-hydroxy-$N^6$-(morpholin-4-ylcarbonyl)-D-lysinamide |
| 71 | 4-cyano-$N^1$-hydroxy-$N^2$-{[4-(phenyloxy)phenyl]sulfonyl}-D-phenylalaninamide |
| 72 | 4-cyano-$N^2$-({3,5-difluoro-4-[(4-fluorophenyl)oxy]phenyl}sulfonyl)-$N^1$-hydroxy-D-phenylalaninamide |
| 73 | 3-cyano-$N^2$-({3,5-difluoro-4-[(4-fluorophenyl)oxy]phenyl}sulfonyl)-$N^1$-hydroxy-D-phenylalaninamide |
| 74 | 3-cyano-$N^1$-hydroxy-$N^2$-{[4-(phenyloxy)phenyl]sulfonyl}-D-phenylalaninamide |
| 75 | $N^2$-({3,5-difluoro-4-[(4-hydroxyphenyl)oxy]phenyl}sulfonyl)-$N^1$-hydroxyargininamide |
| 76 | $N^2$-{[3,5-difluoro-4-(pyridin-3-yloxy)phenyl]sulfonyl}-$N^1$-hydroxyargininamide |
| 77 | $N^2$-({3,5-difluoro-4-[(4-fluorophenyl)oxy]phenyl}sulfonyl)-$N^1$-hydroxy-$N^6$-({[2-(methyloxy)ethyl]amino}carbonyl)-D-lysinamide |
| 78 | $N^2$-({3,5-difluoro-4-[(4-fluorophenyl)oxy]phenyl}sulfonyl)-$N^6$-[1-(4,4-dimethyl-2,6-dioxocyclohexylidene)ethyl]-$N^1$-hydroxy-D-lysinamide |
| 79 | $N^2$-{[3,5-difluoro-4-({4-[(phenylmethyl)oxy]phenyl}oxy)phenyl]sulfonyl}-$N^1$-hydroxyargininamide |
| 80 | $N^2$-{[3,5-difluoro-4-(pyridin-3-yloxy)phenyl]sulfonyl}-$N^1$-hydroxy-6-morpholin-4-yl-D-norleucinamide |
| 81 | $N^2$-({3-fluoro-4-[(4-fluorophenyl)oxy]phenyl}sulfonyl)-$N^1$-hydroxy-3-morpholin-4-yl-D-alaninamide |
| 82 | $N^2$-({3,5-difluoro-4-[(4-fluorophenyl)oxy]phenyl}sulfonyl)-$N^1$-hydroxy-4-[(hydroxyamino)(imino)methyl]-D-phenylalaninamide |
| 83 | $N^2$-({3,5-difluoro-4-[(4-fluorophenyl)oxy]phenyl}sulfonyl)-$N^1$-hydroxy-3-[(hydroxyamino)(imino)methyl]-D-phenylalaninamide |
| 84 | $N^2$-({4-[(4-chlorophenyl)oxy]-3,5-difluorophenyl}sulfonyl)-$N^1$-hydroxy-3-[1-(morpholin-4-ylcarbonyl)piperidin-4-yl]alaninamide |
| 85 | $N^2$-({3,5-difluoro-4-[(4-fluorophenyl)oxy]phenyl}sulfonyl)-$N^1$-hydroxy-3-[1-(morpholin-4-ylcarbonyl)piperidin-4-yl]alaninamide |
| 86 | 3-[amino(imino)methyl]-$N^2$-({3,5-difluoro-4-[(4-fluorophenyl)oxy]phenyl}sulfonyl)-$N^1$-hydroxy-D-phenylalaninamide |
| 87 | 4-[amino(imino)methyl]-$N^2$-({3,5-difluoro-4-[(4-fluorophenyl)oxy]phenyl}sulfonyl)-$N^1$-hydroxy-D-phenylalaninamide |
| 88 | $N^5$-(aminocarbonyl)-$N^2$-({3-fluoro-4-[(4-fluorophenyl)oxy]phenyl}sulfonyl)-$N^1$-hydroxy-D-ornithinamide |
| 89 | (2R)-$N^2$-[({4-[(4-chlorophenyl)oxy]-3,5-difluorophenyl}sulfonyl)amino]-4-(dimethylamino)-$N^1$-hydroxybutanamide |

TABLE 1-continued

| # | Compound Name |
|---|---|
| 90 | (2R)-N²-[({4-[(4-chlorophenyl)oxy]-3,5-difluorophenyl}sulfonyl)amino]-4-{[1-(4,4-dimethyl-2,6-dioxocyclohexylidene)-2-methylbutyl]amino}-N¹-hydroxybutanamide |
| 91 | N²-({4-[(4-chlorophenyl)oxy]-3,5-difluorophenyl}sulfonyl)-N¹-hydroxy-3-[(2-morpholin-4-yl-2-oxoethyl)thio]-D-valinamide |
| 92 | (2R)-4-amino-N²-[({4-[(4-chlorophenyl)oxy]-3,5-difluorophenyl}sulfonyl)amino]-N¹-hydroxybutanamide |
| 93 | (2R)-4-{[amino(imino)methyl]amino}-N²-[({4-[(4-chlorophenyl)oxy]-3,5-difluorophenyl}sulfonyl)amino]-N¹-hydroxybutanamide |
| 94 | N²-[({4-[(4-chlorophenyl)oxy]-3,5-difluorophenyl}sulfonyl)amino]-N¹-hydroxy-2-piperidin-4-ylacetamide |
| 95 | N²-[({4-[(4-chlorophenyl)oxy]-3-fluorophenyl}sulfonyl)amino]-N¹-hydroxy-2-piperidin-4-ylacetamide |
| 96 | N²-[({3-fluoro-4-[(4-fluorophenyl)oxy]phenyl}sulfonyl)amino]-N¹-hydroxy-2-piperidin-4-ylacetamide |
| 97 | N²-[({4-[(4-fluorophenyl)oxy]phenyl}sulfonyl)amino]-N¹-hydroxy-2-piperidin-4-ylacetamide |
| 98 | N²-({[6-(3-fluorophenyl)pyridin-3-yl]sulfonyl}amino)-N¹-hydroxy-2-piperidin-4-ylacetamide |
| 99 | N²-[({4-[(3,5-dimethylphenyl)oxy]-3,5-difluorophenyl}sulfonyl)amino]-N¹-hydroxy-2-piperidin-4-ylacetamide |
| 100 | 3-[4-(aminomethyl)cyclohexyl]-N²-({4-[(4-chlorophenyl)oxy]-3,5-difluorophenyl}sulfonyl)-N¹-hydroxyalaninamide |
| 101 | 3-[4-(aminomethyl)cyclohexyl]-N²-({3,5-difluoro-4-[(4-fluorophenyl)oxy]phenyl}sulfonyl)-N¹-hydroxyalaninamide |
| 102 | 3-[4-(aminomethyl)cyclohexyl]-N²-({4-[(4-chlorophenyl)oxy]-3-fluorophenyl}sulfonyl)-N¹-hydroxyalaninamide |
| 103 | 3-[4-(aminomethyl)cyclohexyl]-N²-({3-fluoro-4-[(4-fluorophenyl)oxy]phenyl}sulfonyl)-N¹-hydroxyalaninamide |
| 104 | 3-[4-(aminomethyl)cyclohexyl]-N²-({4-[(4-fluorophenyl)oxy]phenyl}sulfonyl)-N¹-hydroxyalaninamide |
| 105 | 3-[4-(aminomethyl)cyclohexyl]-N²-{[6-(3-fluorophenyl)pyridin-3-yl]sulfonyl}-N¹-hydroxyalaninamide |
| 106 | 3-[4-(aminomethyl)cyclohexyl]-N²-({4-[(3,5-dimethylphenyl)oxy]-3,5-difluorophenyl}sulfonyl)-N¹-hydroxyalaninamide |

In Aspect K, the invention comprises a pharmaceutical composition comprising a compound as described in any of the embodiments of Aspects A, B, C, D, E, F, G, H and J and a pharmaceutically acceptable carrier.

In Aspect L, the invention comprises a method of making a compound as described in any of the embodiments of Aspects A, B, C, D, E, F, G, H and J. In particular are described, methods of making bis-aryl ether sulfonyl halide intermediates, which are used to make compounds of the invention, methods of making compounds of the invention both in solution-phase as well as on solid-phase.

The following paragraphs provide definitions of the various chemical moieties that make up the compounds of the invention and are intended to apply uniformly throughout the specification and claims unless expressly stated otherwise.

The term alkyl refers inclusively to a univalent $C_1$ to $C_{20}$ (unless explicitly stated otherwise) saturated straight, branched, cyclic, and combinations thereof alkane moiety and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. In certain instances, specific cycloalkyls are defined (e.g. $C_3$-$C_8$ cycloalkyl) to differentiate them from generically described alkyls (that, again, are intended to construe inclusion of cycloalkyls). Thus "alkyl" includes, e.g., $C_3$-$C_8$ cycloalkyl. The term "alkyl" also includes, e.g., $C_3$-$C_8$ cycloalkyl $C_1$-$C_6$ alkyl, which is a $C_1$-$C_6$ alkyl having a $C_3$-$C_8$ cycloalkyl terminus. Alkyl's can be optionally substituted with any appropriate group, including but not limited to one or more moieties selected from halo, hydroxyl, amino, arylalkyl, heteroarylalkyl, alkylamino, arylamino, alkoxy, aryloxy, nitro, cyano, sulfonic acid, sulfate, phosphonic acid, phosphate, or phosphonate, either unprotected, or protected as necessary, as known to those skilled in the art or as taught, for example, in Greene, et al., "Protective Groups in Organic Synthesis," John Wiley and Sons, Second Edition, 1991.

The term alkoxy refers to an alkyl (as defined above) moiety having a terminal —O— with a free valence, e.g., $CH_3CH_2$—O—;

The term alkenyl refers to a univalent $C_2$-$C_6$ straight, branched, or in the case of $C_{5-8}$, cyclic hydrocarbon with at least one double bond.

The term aryl refers to a univalent phenyl, biphenyl, napthyl, and the like. The aryl group can be optionally substituted with any suitable group, including but not limited to one or more moieties selected from halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991). As well, substitution on an aryl can include fused rings such as in tetrahydronaphthalene, chromen-2-one, dibenzofuran, and the like. In such cases, e.g. tetrahydronaphthalene, the aryl portion of the tetrahydronaphthalene is attached to the portion of a molecule described as having an aryl group.

The term heteroatom means O, S, or N.

The term heterocycle refers to a cyclic alkyl, alkenyl, or aryl moiety as defined above wherein one or more ring carbon atoms is replaced with a heteroatom.

The term heteroaryl specifically refers to an aryl that includes at least one of sulfur, oxygen, and nitrogen in the aromatic ring. Nonlimiting examples are pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl.

The term halo refers to chloro, fluoro, iodo, or bromo.

As used herein, the term pharmaceutically acceptable salts or complexes refers to salts or complexes that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term pharmaceutically active derivative refers to any compound that upon administration to the recipient, is capable of providing directly or indirectly, the compounds disclosed herein.

In some examples, as will be appreciated by those skilled in the art, two adjacent carbon containing groups on an aromatic system may be fused together to form a ring structure. The fused ring structure may contain heteroatoms and may be substituted with one or more substitution groups "R". It should additionally be noted that for cycloalkyl (i.e. saturated ring structures), each positional carbon may contain two substitution groups, e.g. R and R'.

Some of the compounds of the invention may have imino, amino, oxo or hydroxy substituents off aromatic heterocyclic ring systems. For purposes of this disclosure, it is understood that such imino, amino, oxo or hydroxy substituents may exist in their corresponding tautomeric form, i.e., amino, imino, hydroxy or oxo, respectively.

Compounds of the invention are generally named using ACD/Name (available from Advanced Chemistry Development, Inc. of Toronto, Canada). This software derives names from chemical structures according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. When desired, the R- and S-isomers may be resolved by methods known to one skilled in the art, for example by: formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about 1 and about 6 carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about 1 and about 6 carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference.

"Metabolite" refers to the break-down or end product of a compound or its salt produced by metabolism or biotransformation in the animal or human body; e.g., biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be synthesized such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated, prophalactically or otherwise.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one skilled in the art.

The compounds of the invention can be made following the teachings provided in the Examples, below, and method routine to those of ordinary skill in the art. The Examples describe how to make sulfonyl chloride intermediates used to make compounds of the invention, as well as solution and solid-phase methods of making compounds of the invention. The Examples are illustrative and are not intended to be limiting.

EXAMPLES

Example 1

Synthesis of Intermediates 4-(4-fluorophenoxy)-3,5-difluorophenylsulfonyl chloride Step 1: A mixture of 3,4,5-trifluoronitrobenzene (20.0 g, 113 mmol, commercially available from AsymChem of Durham, N.C.), dry DMF (100 ml), 4-fluorophenol (13.9 g, 124 mmol), and $Cs_2CO_3$ (56 g, 172 mmol) was stirred under $N_2$ at 60-70° C. for 1-2 hrs. After cooling to room temperature, the reaction mixture was partitioned between $H_2O$ and EtOAc. The phases were separated and the aqueous phase was further extracted with EtOAc (2×). The EtOAc extractions were washed with sat'd NaCl (1×), dried over $Na_2SO_4$, and concentrated in vacuo to give 4-(4-fluorophenoxy)-3,5-difluoronitrobenzene (32.0 g, 105%) which was used in the next step without further purification. $^1H$ NMR (DMSO-$d_6$): δ 7.15 (m, 2H), 7.22 (m, 2H), 8.31 (d, 2H, J=7.6 Hz).

Step 2: A mixture of 4-(4-fluorophenoxy)-3,5-difluoronitrobenzene (30.4 g, 113 mmol), EtOAc (300 ml), 10% Pd/C (2.6 g) was stirred under an atmosphere of $H_2$ at room temperature and pressure for approximately 6 hrs. The reaction mixture was filtered through Celite and concentrated in vacuo to give 4-(4-fluorophenoxy)-3,5-difluoroaniline (26.5 g, 98%) which was used in the next step without further purification. $^1H$ NMR ($CDCl_3$): δ 3.82 (s, 2H), 6.26 (d, 2H, J=8.4 Hz), 6.88 (m, 2H), 6.93 (m, 2H).

Step 3: A solution of $NaNO_2$ (8.4 g, 122 mmol) in $H_2O$ (20 ml) was added dropwise to a mixture of 4-(4-fluorophenoxy)-3,5-difluoroaniline (26.5 g, 111 mol), AcOH (160 ml), and conc. HCl (160 ml) cooled in an ice/NaCl/$H_2O$ bath. After addition was complete, the mixture was stirred an additional 20-30 minutes before a mixture of $SO_2$ (74 g, 1.15 mol) in AcOH (140 ml) and $CuCl_2 \cdot 2H_2O$ (11.1 g, 65 mmol) in $H_2O$ (16 ml) was added. The reaction mixture was removed from the ice bath and stirred at room temperature for 1-2 hrs. The reaction mixture was poured into ice water and extracted with $CH_2Cl_2$ (3×). The combined $CH_2Cl_2$ extractions were washed with sat'd NaCl (1×), dried over $Na_2SO_4$, and concentrated in vacuo. The resulting crude oil was purified by flash chromatography (9:1 hexanes:EtOAC) to give 4-(4-fluorophenoxy)-3,5-difluorophenylsulfonyl chloride (29.8 g, 83%). $^1H$ NMR ($CDCl_3$): δ 6.94 (m, 2H), 7.10 (m, 2H), 7.71 (d, 2H, J=6.4 Hz).

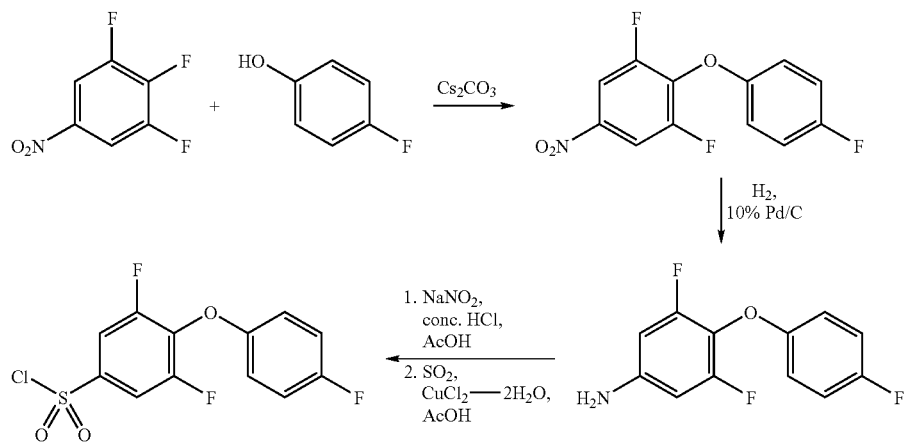

4-(4-Chlorophenoxy)-3,5-difluorophenylsulfonyl Chloride

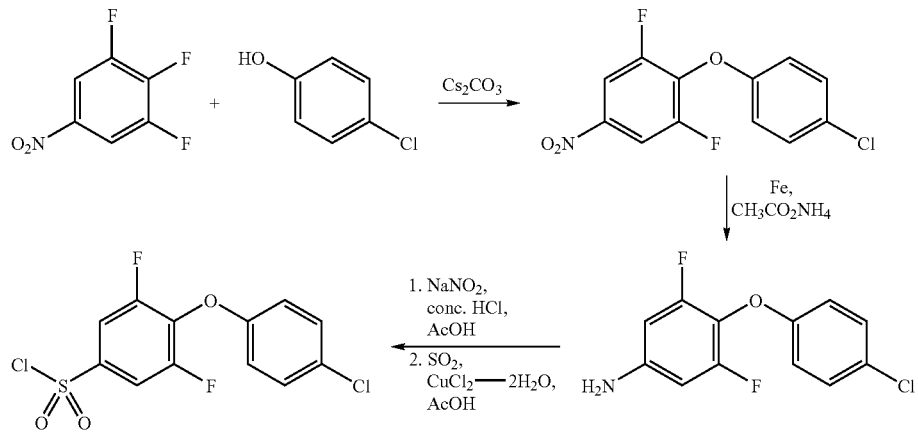

Step 1: A mixture of 3,4,5-trifluoronitrobenzene (6.6 g, 37 mmol), dry DMF (30 ml), 4-chlorophenol (5.26 g, 41 mmol), and $Cs_2CO_3$ (18.8 g, 58 mmol) was stirred under $N_2$ at 60-70 C for 1-2 hrs. After cooling to room temperature, the reaction mixture was partitioned between $H_2O$ and EtOAc. The phases were separated and the aqueous phase was further extracted with EtOAc (2×). The EtOAc extractions were washed with sat'd NaCl (1×), dried over $Na_2SO_4$, and concentrated in vacuo to give 4-(4-chlorophenoxy)-3,5-difluoronitrobenzene (11.3 g, 106%) which was used in the next step without further purification. $^1$H NMR ($CDCl_3$): δ 6.90 (d, 2H, J=7.6 Hz), 7.28 (d, 2H, J=7.6 Hz), 7.94 (d, 2H, J=6.4 Hz). Note: $K_2CO_3$/acetonitrile can be used in lieu of $Cs_2CO_3$/DMF.

Step 2: A mixture of 4-(4-chlorophenoxy)-3,5-difluoronitrobenzene (10.6 g, 37 mmol), toluene (150 ml), $H_2O$ (150 ml), iron powder (6.9 g, 124 mmol), and ammonium acetate (9.3 g, 120 mmol) was heated to reflux with stirring for 2-3 hrs. After cooling to room temperature, the reaction mixture was filtered through Celite with thorough washing with $H_2O$ and EtOAc. The filtrate was transferred to a separatory funnel and the phases separated. The aqueous phase was further extracted with EtOAc (2×). The combined organic phases were washed with $H_2O$ (1×), sat'd NaCl (1×), dried over $Na_2SO_4$, and concentrated in vacuo to give 4-(4-chlorophenoxy)-3,5-difluoroaniline (10.8 g, 113%) which was used in the next step without further purification. $^1$H NMR ($CDCl_3$): δ 3.81 (s, 2H), 6.27 (d, 2H, J=9.2 Hz), 6.85 (d, 2H, J=9.2 Hz), 7.21 (d, 2H, J=9.2 Hz).

Step 3: A solution of $NaNO_2$ (2.8 g, 41 mmol) in $H_2O$ (7.0 ml) was added dropwise to a mixture of 4-(4-chlorophenoxy)-3,5-difluoroaniline (9.5 g, 37 mmol), AcOH (50 ml), and conc. HCl (50 ml) cooled in an ice/NaCl/$H_2O$ bath. After addition was complete, the mixture was stirred an additional 20-30 minutes before a mixture of $SO_2$ (25 g, 290 mmol) in AcOH (50 ml) and $CuCl_2 \cdot 2H_2O$ (3.8 g, 22 mmol) in $H_2O$ (6.0 ml) was added. The reaction mixture was removed from the ice bath and stirred at room temperature for 1-2 hrs. The reaction mixture was poured into ice water and extracted with $CH_2Cl_2$ (3×). The combined $CH_2Cl_2$ extractions were washed with sat'd NaCl (1×), dried over $Na_2SO_4$, and concentrated in vacuo. The resulting crude oil was purified by flash chromatography (9:1 hexanes:EtOAC) to give 4-(4-chlorophenoxy)-3,5-difluorophenylsulfonyl chloride (11.0 g, 87%). $^1$H NMR ($CDCl_3$): δ 6.92 (d, 2H, J=7.2 Hz), 7.30 (d, 2H, J=7.2 Hz), 7.72 (d, 2H, J=4.8 Hz).

3,4,5-trifluorobenzenesulfonyl chloride

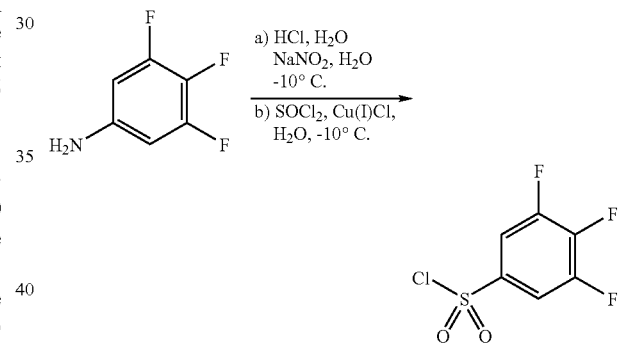

To a 2000 mL round-bottomed flask was added 800 mL distilled $H_2O$ and a stir bar. Upon stirring, the flask was cooled to −10° C. in an ice-acetone bath. The flask was fitted with a 500 mL addition funnel and $SOCl_2$ (300 mL, 4.1 mol, 10 eq.) was added dropwise over a period of 1 h. After complete addition, the solution was stirred for 4 h while warming to room temperature.

Meanwhile, in a separate 500 mL recovery flask was added 3,4,5-trifluoroaniline (61 g, 0.41 mol, 1.0 eq.), conc. HCl (150 mL), and a stir bar. The resulting suspension was stirred vigorously and cooled to −10° C. The flask was fitted with a 250 mL addition funnel and a solution of $NaNO_2$ (34.3 g, 0.50 mol, 1.2 eq.) in $H_2O$ (125 mL) was added to the suspension dropwise over a period of 10 min. The reaction mixture, now nearly homogeneous, is yellow-orange in color. The reaction mixture was stirred for an additional 30 min while carefully maintaining the temperature at −10° C.

The flask containing the $SOCl_2/H_2O$ solution is cooled again to −10° C. and a catalytic amount of Cu(I)Cl (~50 mg) was added. The solution turns dark green in color. The flask was fitted with a 500 mL addition funnel (previously chilled to 0° C.) and the 3,4,5-trifluorodiazobenzene solution was quickly transferred to the funnel. The solution was immediately added dropwise over a period of 3 min. After addition, the reaction mixture slowly turns darker green in color, but after stirring for 5 min becomes bright, lime green. The reaction was stirred for an additional hour while warming to room temperature. The reaction mixture was transferred to a separatory funnel and extracted with $CH_2Cl_2$ (3×200 mL). The organic phases are combined and dried over anhydrous $Na_2SO_4$, filtered, and concentrated to give a dark-bronze oil (79.5 g, 83%).

Example 2

Synthesis of $N^2$-{[3,5-difluoro-4-(4-fluorophenoxy)phenyl]sulfonyl}-$N^1$-hydroxy-D-argininamide Arginine-Derived Trifluoroarylsulfonamide Intermediate

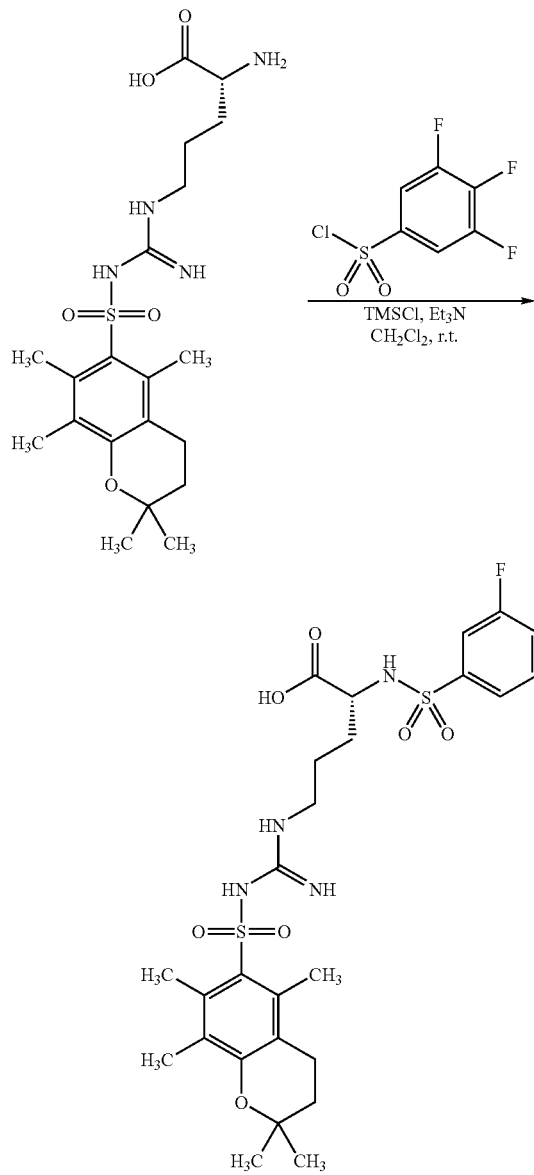

To a 1000 mL round-bottomed flask was added H-D-Arg(Pmc)-OH (15.7 g, 35.7 mmol, 1.0 eq.), $CH_2Cl_2$ (250 mL), and a stir bar. The resulting suspension was stirred vigorously and trimethylsilyl chloride (TMS-Cl) (7.76 g, 71.4 mmol, 2.0 eq.) was added via syringe over a period of 30 sec. After stirring for approximately 20 min, the solution becomes homogeneous. $Et_3N$ (20 mL, 143 mmol, 4.0 eq.) was added via syringe over a period of 1 min. After stirring for an additional 20 min, the reaction flask was fitted with a 250 mL addition funnel and a solution of 3,4,5-trifluorobenzenesulfonyl chloride (9.06 g, 39.3 mmol, 1.1 eq.) in $CH_2Cl_2$ (50 mL) was added dropwise over a period of 3 min. The reaction mixture was stirred overnight at room temperature. The reaction mixture was then concentrated in vacuo and dissolved in saturated $NaHCO_3$ (500 mL) with stirring. The homogeneous solution was transferred to a separatory funnel and extracted with $Et_2O$ (2×100 mL). The aqueous phase was drained into a 2000 mL beaker and acidified to pH 2 with 1 N HCl. Upon acidification, the desired sulfonamide precipitated as a white solid (sulfonamide). The aqueous suspension was extracted with EtOAc (2×300 mL). The organic phase was washed with brine (1×100 mL) and the organic phases were combined and dried over anhydrous $NaHCO_3$, filtered, and concentrated to give an off-white solid. The solid was purified via flash chromatography (10% MeOH in $CH_2Cl_2$ w/0.05% AcOH, $R_f$=0.33), yielding the pure sulfonamide as an off-white solid as a foam (14.5 g, 64%). LC/MSD (HP Series 1100 MSD): Expected MW: 634.17, Observed M+H, 635.1, Retention time: 1.5 min.

Arginine-Derived Bis-Aryl Ether Intermediate

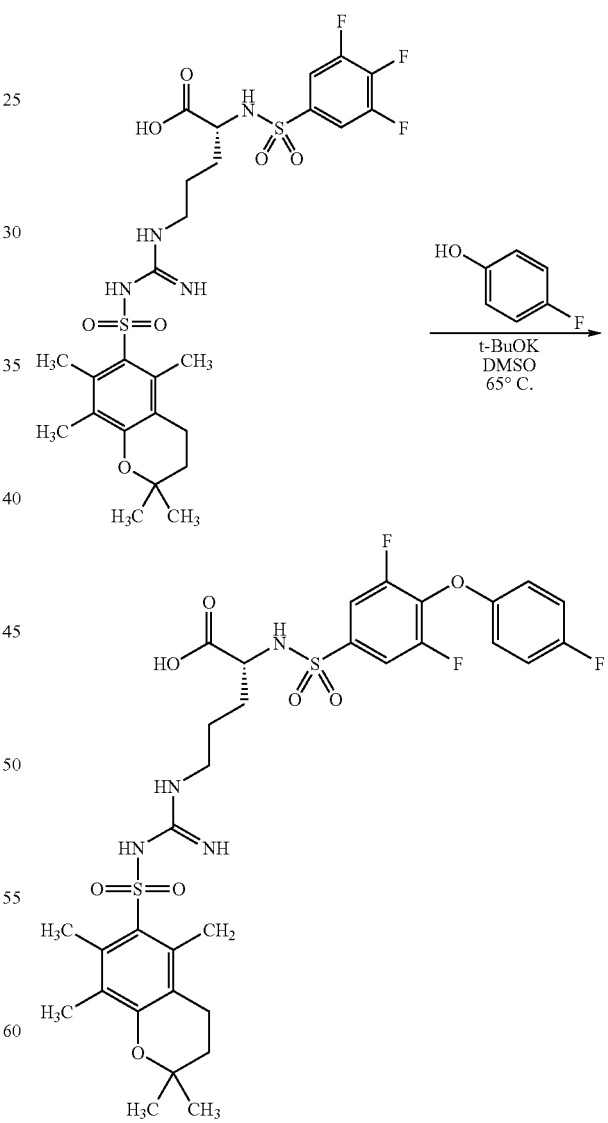

To a 1000 mL recovery flask was added trifluorobenzene sulfonamide (7.0 g, 11.0 mmol, 1.0 eq.), 4-fluorophenol (12.4 g, 110 mmol, 10 eq.), DMSO (230 mL), and a stir bar. With stirring the flask was fitted with a 100 mL addition funnel and potassium tert-butoxide (1 M in t-BuOH, 99 ml, 99 mmol, 9.0 eq.) was added dropwise over a period of 5 min. Upon complete addition the reaction flask was heated overnight in an oil bath at 65° C. The reaction color becomes an opaque brown as the reaction progressed. The reaction mixture was removed from the oil bath, allowed to cool to room temperature, and diluted with EtOAc (300 mL). The mixture was then acidified to pH 2-3 with 1N HCl. The aqueous layer was extracted with EtOAc (3×50 mL). The organic phases were combined and washed with brine (1×100 mL). The organic phase was dried over anhydrous Na$_2$SO$_4$, filtered, and concentrated to give a dark, viscous oil that was carried onto the next step without purification. LC/MSD (HP Series 1100 MSD): Expected MW: 726.20, Observed M+H, 727.1, Retention time: 1.62 min.

Arginine-Derived Bis-Aryl Ether Intermediate: Ester Formation

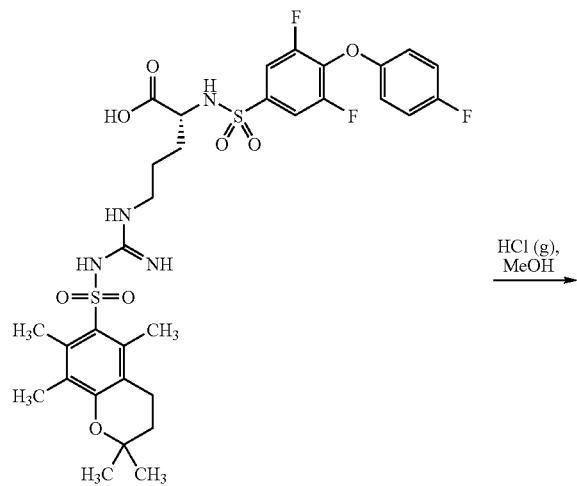

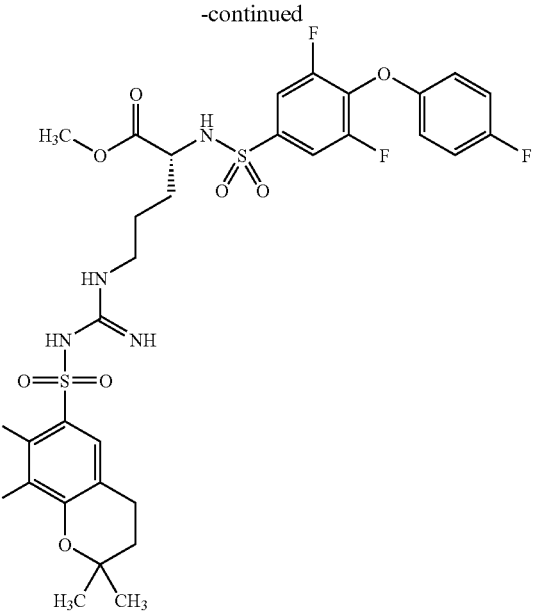

To a 200 mL recovery flask was added crude biphenyl ether (~6.6 g, 9.04 mmol, 1.0 eq.) and anhydrous MeOH (125 mL). HCl gas was bubbled into the reaction until the solution was saturated. The reaction was fitted with a septum and stirred overnight at room temperature. The reaction mixture was concentrated to a viscous oil and purified via flash chromatography (gradient of 100% Hex to 100% EtOAc) to yield a off-white bubbly solid (3.3 g, 49% over two steps from the trifluorobenzene sulfonamide free acid). LC/MSD (HP Series 1100 MSD): Expected MW: 740.22, Observed M+H, 741.1, Retention time: 1.95 min.

Arginine-Derived Bis-Aryl Ether Intermediate: Removal of Guanidine Protecting Group

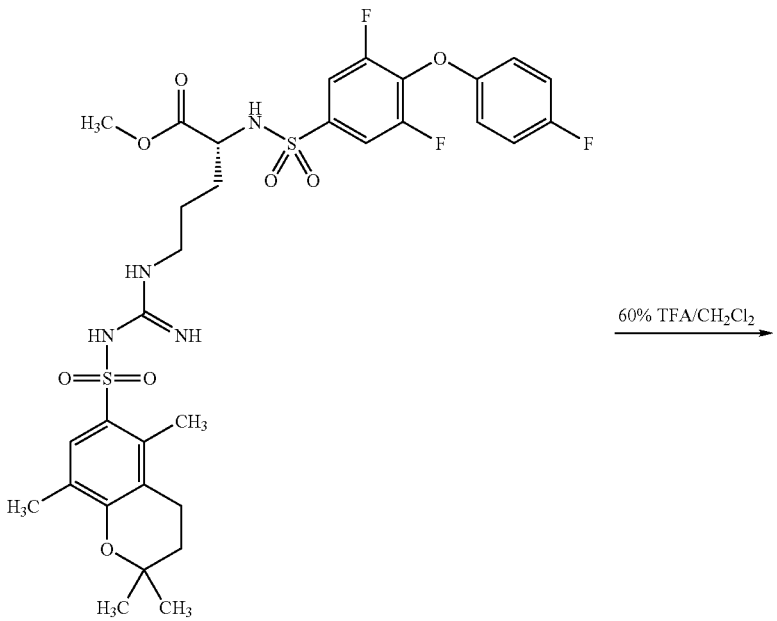

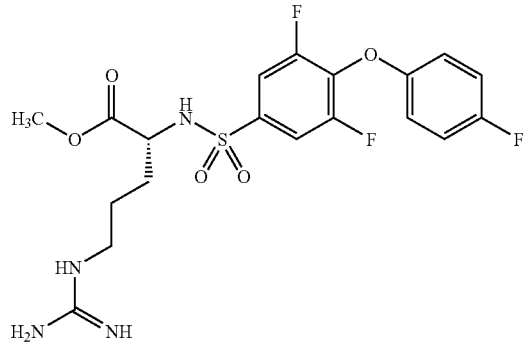

To a 500 mL recovery flask was added biphenyl ether methyl ester (3.3 g, 4.45 mmol, 1.0 eq.) and a stir bar. In a separate Erlenmeyer flask, 60% TFA/CH$_2$Cl$_2$ solution (250 mL) was prepared. The solution was added to the reaction flask and the resulting solution was stirred for 1.5 h. The reaction mixture was concentrated in vacuo and azeotroped with toluene (3×20 mL). The oil was further concentrated under high vacuum to remove residual toluene and TFA. The resulting oil was carried onto the next step with further purification. LC/MSD (HP Series 1100 MSD): Expected MW: 474.12, Observed M+H, 475.1, Retention time: 1.45 min.

$N^2$-{[3,5-difluoro-4-(4-fluorophenoxy)phenyl]sulfonyl}-$N^1$-hydroxy-D-argininamide

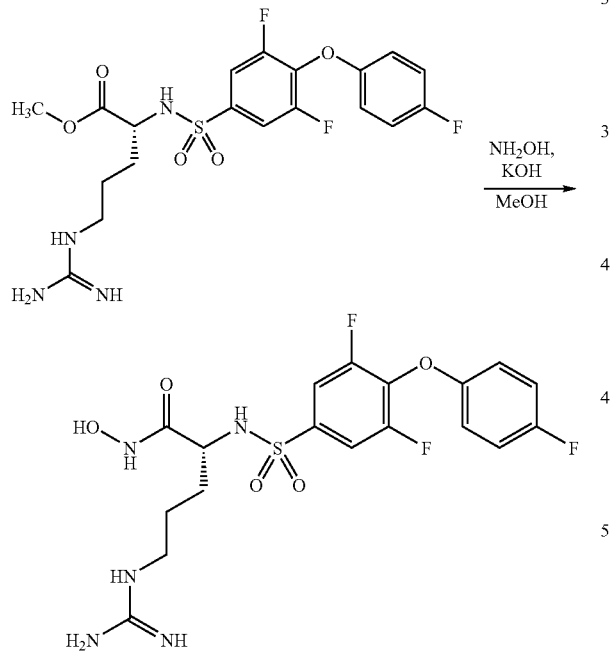

Trifluoroacetate salt of N-2-{[3,5-difluoro-4-(4-fluorophenoxy)phenyl]sulfonyl}-N-1-hydroxy-D-argininamide Solutions of HONH$_2$.HCl (6.18 g, 89.0 mmol, 20 eq.) in hot anhydrous MeOH (31 mL) and KOH (7.48 g, 133 mmol, 30.0 eq.) in hot anhydrous MeOH (19 mL) were prepared. Upon dissolving, both solutions were removed from the hotplate and the KOH solution was added directly to the HONH$_2$.HCl solution. Upon addition, a white solid (KCl) immediately precipitated. The resulting solution was allowed to stand for 20 min. The solution was filtered into a 200 mL recovery flask containing the methyl ester (2.1 g, 4.45 mmol, 1.0 eq.) and a stir bar. Considerable bubbling occurred upon addition. The reaction was stirred at room temperature for 1.5 h. The reaction mixture was acidified to pH 5 with 1N HCl. A viscous solid formed in the flask. The solution was concentrated and then redissolved in MeOH. An off-white solid (HONH$_2$) remains out of solution. The solution was filtered and concentrated. Filtration was repeated as necessary until no more HONH$_2$ was evident. The resulting dark solid was redissolved in MeOH and purified via reverse phase HPLC (0.5% TFA/AcCN, 0.5% TFA/H$_2$O) to give an off-white solid (1.0 g, 48% over two steps from Pmc-protected methyl ester). LC/MSD (HP Series 1100 MSD): Expected MW: 475.11, Observed M+H, 476.1, Retention time: 1.33 min.

Example 3

Synthesis of $N^2$-{[4-(4-chlorophenoxy)-3,5-difluorophenyl]sulfonyl}-$N^1$-hydroxy-D-argininamide and $N^2$-{[4-(4-bromophenoxy)-3,5-difluorophenyl]sulfonyl}-$N^1$-hydroxy-D-argininamide

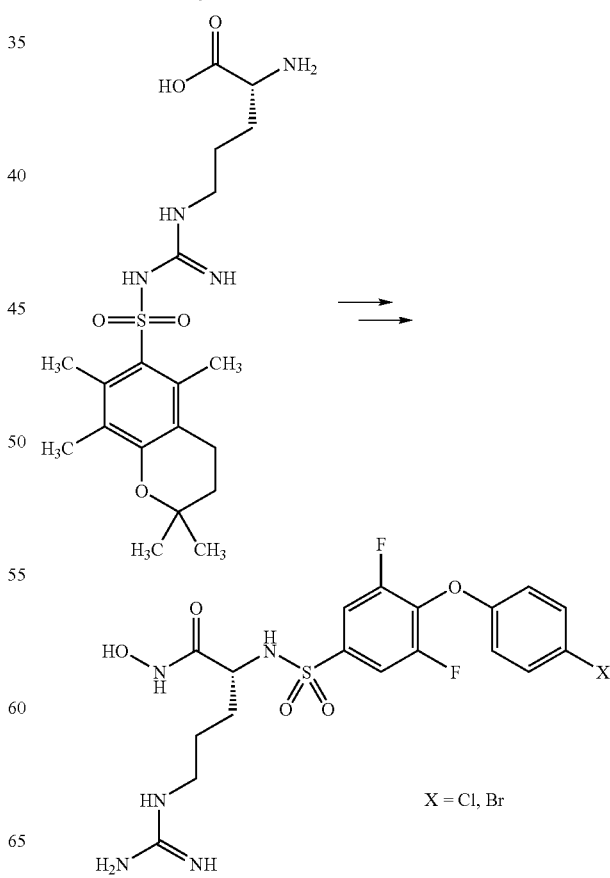

X = Cl, Br

The above compounds (X=Cl, Br) were prepared via solution phase chemistry in a manner similar to description above:

$N^2$-{[4-(4-chlorophenoxy)-3,5-difluorophenyl]sulfonyl}-$N^1$-hydroxy-D-argininamide LC/MSD (HP Series 1100 MSD): Expected MW: 491.08, Observed M+H, 492.0, Retention time: 1.37 min $N^2$-{[4-(4-bromophenoxy)-3,5-difluorophenyl]sulfonyl}-$N^1$-hydroxy-D-argininamide LC/MSD (HP Series 1100 MSD): Expected MW: 535.03, Observed M+H, 536.0, Retention time: 1.39 min

Example 4

N-2-[(3,5-difluoro-4-phenoxyphenyl)sulfonyl]-N-1-hydroxy-D-argininamide

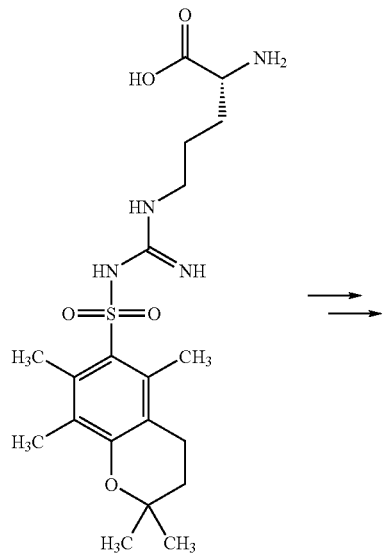

-continued

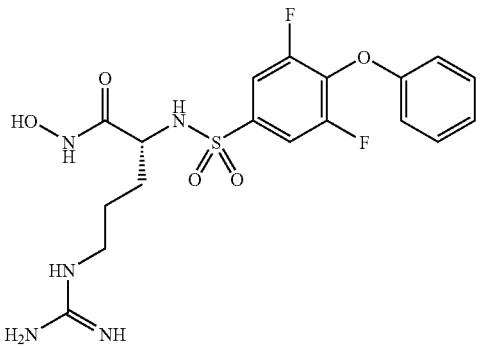

The above compound was prepared according to solid phase methods described below. LC/MSD (HP Series 1100 MSD) Expected MW: 457.12, Observed M+H, 458.1 Retention time: 1.38 min.

Example 5

Alternative Synthesis of N-2-{[4-(4-chlorophenoxy)-3,5-difluorophenyl]sulfonyl}-N-1-hydroxy-D-argininamide The following synthetic scheme illustrates how bis-aryl ether sulfonyl halide intermediates, as described above, can be used to make compounds of the invention. That is, rather than forming a bis-aryl ether sulfonamide from an existing haloaryl sulfonamide, as described above, in this case a bis-aryl ether sulfonyl halide is used to acylate, for example, an arginine-derived intermediate on its alpha-nitrogen to make the corresponding sulfonamide. Further steps to convert such bis-aryl ether sulfonamide intermediates to corresponding compounds of the invention is also illustrated, specifically regarding alternative protection deprotection strategies on route to hydroximate-derived compounds of the invention.

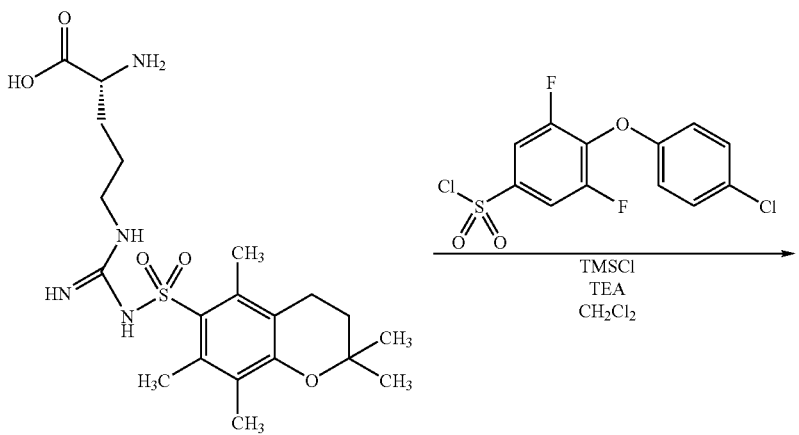

a

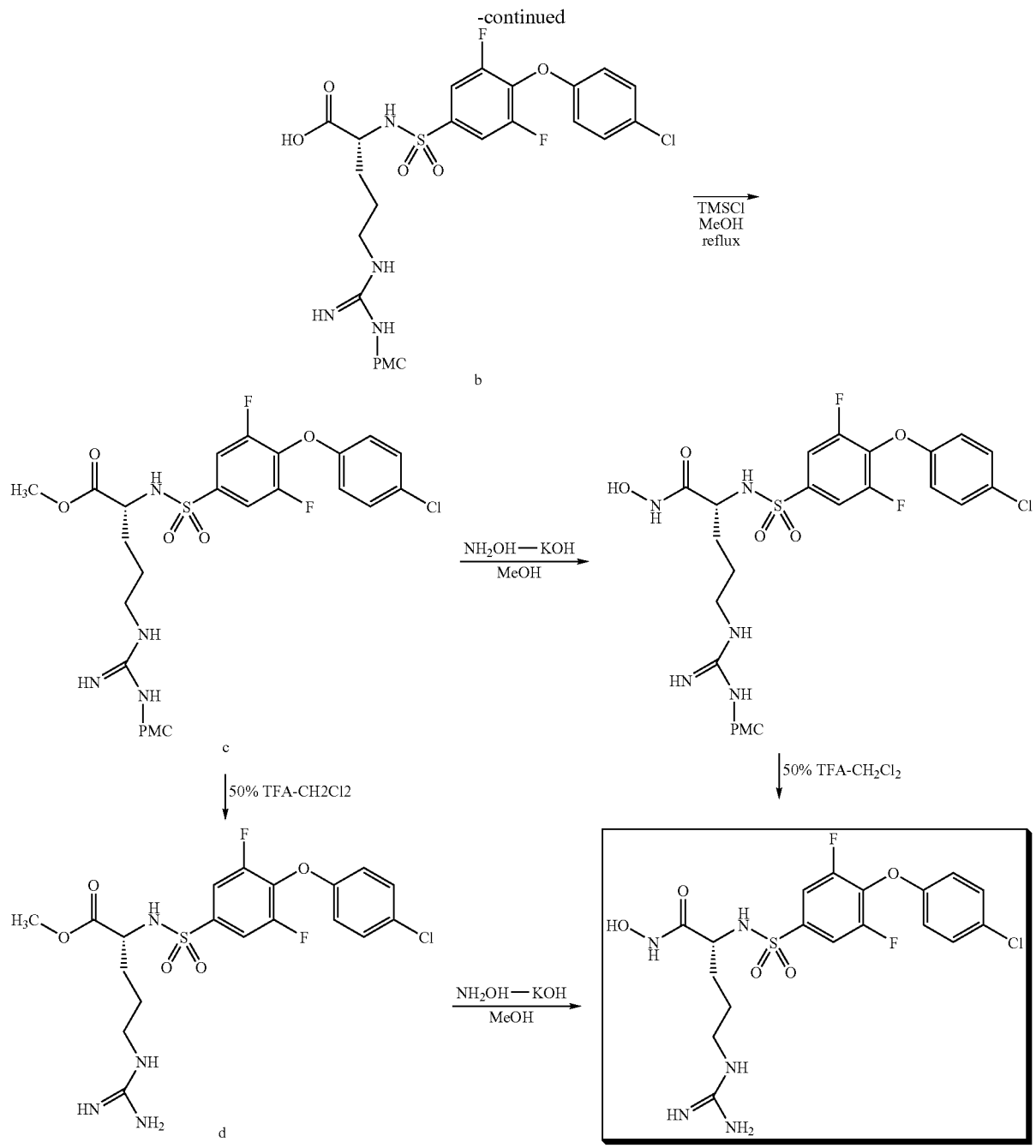

Sulfonamide b

D-Arg (pmc)-OH (3.21 g) is suspended in dichloromethane (40 ml) and 4 chlorophenoxy-3,5-difluorophenylsulfonyl chloride (2.5 g), triethylamine (4.1 ml) and catalytic amount of DMAP are added. The mixture is stirred at room temperature for 5 hrs. After concentrated the reaction mixture, sat. NaHCO3 (60 ml), water (20 ml) and diethyl ether (80 ml) are added and extracted with ether.

The aqueous phase, after acidifying with 6N HCl, is extracted with ethyl acetate. The combined organic phases are washed with brine, dried (MgSO4) and concentrated under reduced pressure to give compound b as a white solid (5.3 g, 98%). MK830-68: M+1=743.1

Methyl Ester c

Compound b is dissolved in dry MeOH (150 ml) and TMSCl (1.82 ml) is added. The reaction mixture is stirred under the reflux condition for 2 hrs. The reaction mixture is concentrated under reduced pressure to give compound 3 as a white solid. Purification by column chromatography with EtOAc-Hexane (3:1) gives 2.8 g (54%). MK830-70: M+1=757.1

Guanidine d

Compound c (2.8 g) is treated with 50%-trifluoroacetic acid in DCM (50 ml) included triethylsilane (0.5 ml) for 3 hrs. After concentrated the reaction mixture, it was co-evaporated with toluene. The residue is extracted with ether to remove the impurity and gives compound 4 as dark-gray solid (2.1 g, 116%). MK830-73: M+1=491.0

$N^2$-{[4-(4-chlorophenoxy)-3,5-difluorophenyl]sulfonyl}-$N^1$-hydroxy-D-argininamide Compound d (2.1 g) is treated with 1.76M hydroxylamine in KOH methanol solution (preparation: 6.96 g of $NH_2OH$·HCl is dissolved in MeOH (36 ml) and 8.4 g of potassium hydroxide is dissolved in MeOH (21 ml), then mix together and filtered) for 2 hrs. After neutralizing the reaction mixture with 6N HCl, the reaction mixture is filtered to move the salt. The reaction mixture is concentrated and purified by prep-HPLC. Prep-HPLC conditions: 20% to 70% in 60 min (A: water with 0.1% TFA, B: acetonitrile with 0.1% TFA), ca 25 min RT is desired product.

After lyophilization, the product was triturated with 1N—HCl three times, and then with water. White solid 0.87 g (38%). MK 830-80: M+1=492.0. H-NMR (CD3OD, 400 MHz Varian): δ 7.58 (d, J=7.2 Hz, 2H), 7.30 (d, J=9.2 Hz, 2H), 6.99 (d, J=9.2 Hz, 2H), 3.68 (t, 1H), 3.18 (m, 2H), 1.70 (m, 3H), 1.59 (m, 1H)

Example 6

Alternative Synthesis of $N^2$-{[3,5-Difluoro-4-(4-Fluorophenoxy)Phenyl]Sulfonyl}-$N^1$-Hydroxy-D-Argininamide This compound was synthesized via a similar route to $N^1$-hydroxy-$N^2$-[(4-phenoxyphenyl)sulfonyl]-D-argininamide and $N^2$-{[4-(4-chlorophenoxy)-3,5-difluorophenyl]sulfonyl}-$N^1$-hydroxy-D-argininamide:

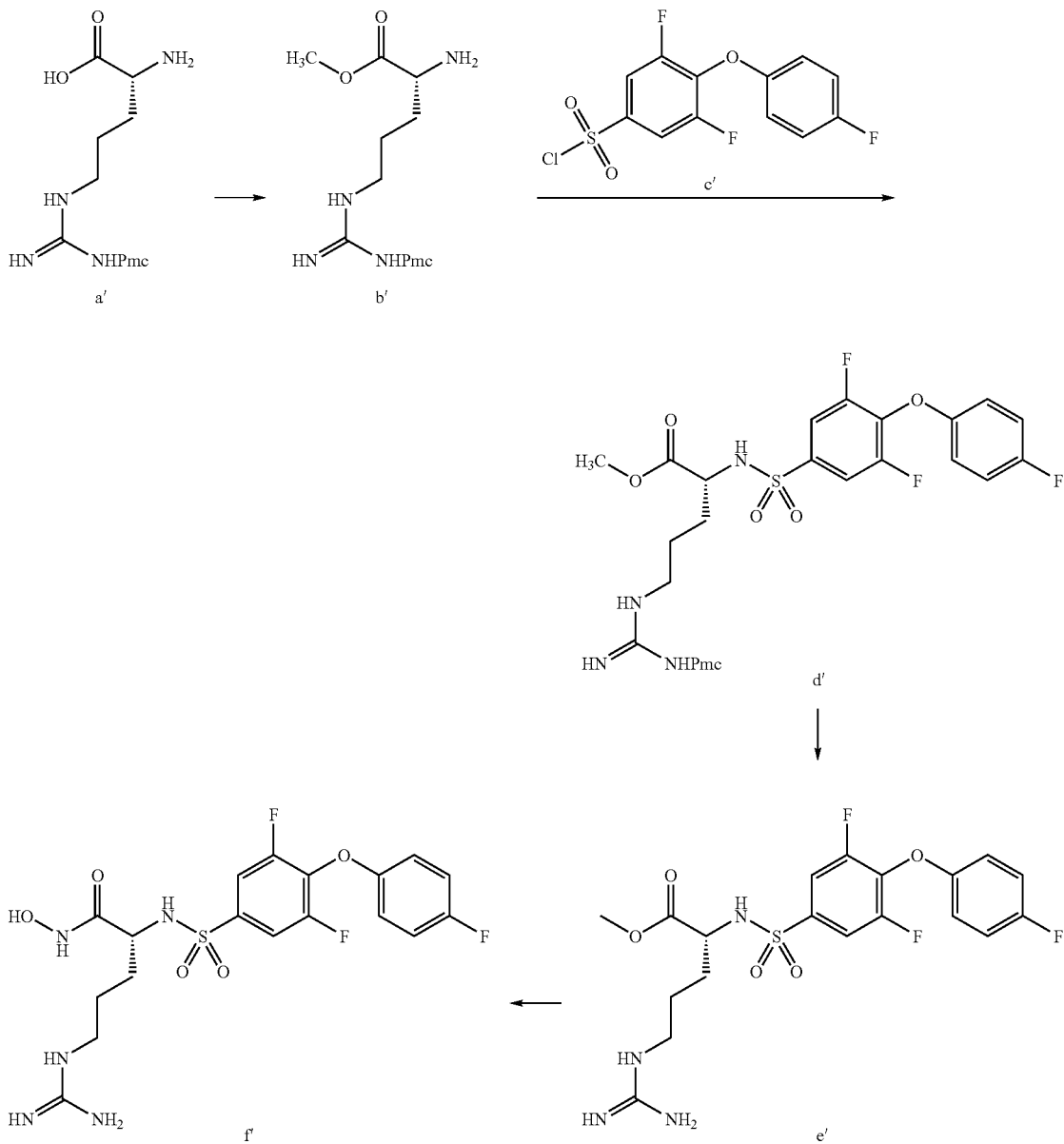

H-D-Arginine(Pmc)-OMe b'

To a round bottom flask equipped with a magnetic stir bar was added H-D-Arginine(Pmc)-OH (13.1 g, 29.7 mmol, 1.0 eq.), dry MeOH (300 mL), and trimethyl silyl chloride (TMSCl) (16.2 g, 18.9 ml, 148.8 mmol, 5.0 eq.). The reaction was then allowed to stir at rt for a total of 36 h before concentrating via rotary evaporation. The viscous oil residue was then dissolved in 400 mL of saturated NaHCO$_3$ and allowed to stir for 10 min. The aqueous layer was then extracted three times with ethyl acetate (300 mL). The combined EtOAc layers were then dried with Na$_2$SO$_4$, concentrated and dried on high vacuum overnight to give H-D-Arginine(Pmc)-OMe b' as a white foam (12.4 g, 92% yield): LC/MS Calcd for [M+H]$^+$ 454.0, found 455.1.

Sulfonamide d'

To a round bottom flask equipped with a magnetic stir bar was added H-D-Arginine(Pmc)-OMe b' (13.0 g, 27.3 mmol, 1.0 eq.), dry CH$_2$Cl$_2$ (200 mL), Triethyl amine (TEA) (7.23 g, 9.2 mL, 71.5 mmol, 2.5 eq.), and sulfonyl chloride c' (9.6 g, 30 mmol, 1.05 eq). The reaction was then allowed to stir at rt for a total of 3 h. An additional 100 ml of CH$_2$Cl$_2$ and the organic layer was washed 2× with water (200 mL), 2× with 0.5M HCl, and 2× with brine. The organic layer was dried with Na$_2$SO$_4$, concentrated, and the solid was columned using the biotage system with the eluant being 2:1 hexane/ethyl acetate. Sulfonamide d' was obtained as a pale yellow foam (20.5 g, 96% yield): LC/MS Calcd for [M+H]$^+$ 740.0, found 741.1.2.

Guanidine e'

To a round bottom flask was added Sulfonamide d' (20.5 g, 27.7 mmol), 1:1 TFA:CH$_2$Cl$_2$ (500 mL), and triethyl silane (5.0 mL). The reaction was allowed to sit at rt for 90 min before concentrating via rotary evaporation. The residual TFA was then removed via azeotroping with toluene. The oil was then triturated 3× with ether (125 mL) to give crude guanidine e' as a white solid. Guanidine e' was then dissolved in 50 mL of EtOAc, concentrated via rotary evaporation, and triturated again 2× with ether (50 mL). Drying of crude guanidine e' on high vacuum overnight afforded a yellow brown foam, which was then rinsed 2× with ether (100 mL), and dried on high vacuum, yielding guanidine e' as a yellow foam which was taken on crude to the next step. LC/MS Calcd for [M+H]$^+$ 474.46, found 475.1.

Hydrochloride Salt of N$^2$-{[3,5-difluoro-4-(4-fluorophenoxy)phenyl]sulfonyl}-N$^1$-hydroxy-D-argininamide To a round bottom flask was added the above crude Guanidine e' (12.1 g, 26.7 mmol, 1.0 eq.), and freshly made 1.76 M HONH$_2$ in MeOH (300 mL, 528 mmol, 20 eq.). The reaction was allowed to sit at rt overnight before filtering off the precipitate, and concentrating the supernatant to one fourth the original volume. The supernatant was then neutralized to pH 7.0 dropwise with neat TFA, concentrated via rotary evaporation, and triturated with ether (100 mL). The crude material was then dissolved in 60 mL of 20:80 acetonitrile:water and purified via three 20 mL injections on a Varian Prep HPLC system: gradient=15% B to 70% B in 40 min where A=100% water, 0.1% TFA, and B=100% acetonitrile, 0.1% TFA; flow rate=160 mL/min, fraction size=100 mL. Each fraction was analyzed on analytical HPLC, and LC/MS. Pure fractions were combined, lyophilized, HCl exchanged with 1N HCl 3×, and water exchanged 1× to give pure N$^2$-{[3,5-difluoro-4-(4-fluorophenoxy)phenyl]sulfonyl}-N$^1$-hydroxy-D-argininamide as a white solid (6.5 g, 45% yield). LC/MS Calcd for [M+H]$^+$ 475.44, found 476.1; $^1$HNMR (400 MHz, MeOD): δ 7.68 (dt, J=8.8, 3.2 Hz, 2H), 7.14 (M, J=8.4 Hz, 6H), 3.65 (t, J=7.6 Hz, 1H), 3.15 (t, J=6.4 Hz, 2H), 1.51-1.69 (m, 4H).

Example 7

Hydrochloride Salt of N-1-Hydroxy-N-2-[(4-Phenoxyphenyl)Sulfonyl]-D-Argininamide This compound was made via two different pathways as shown below.

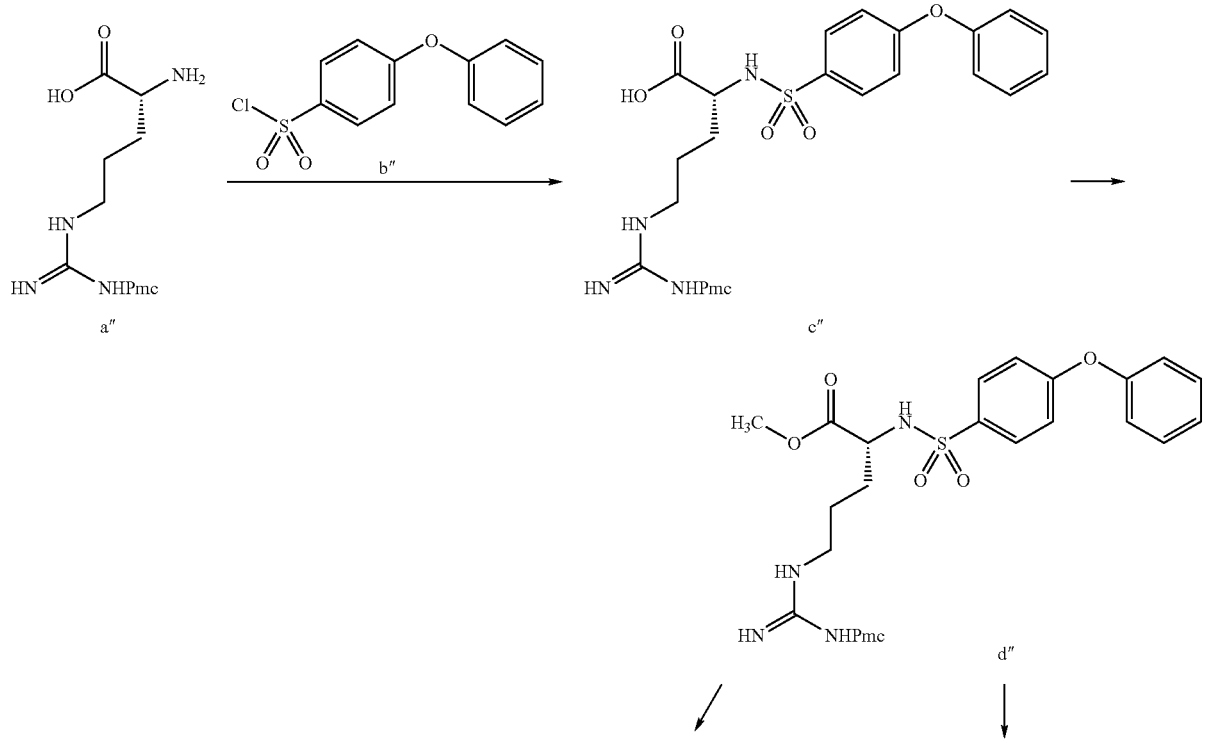

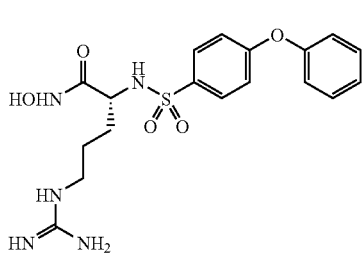
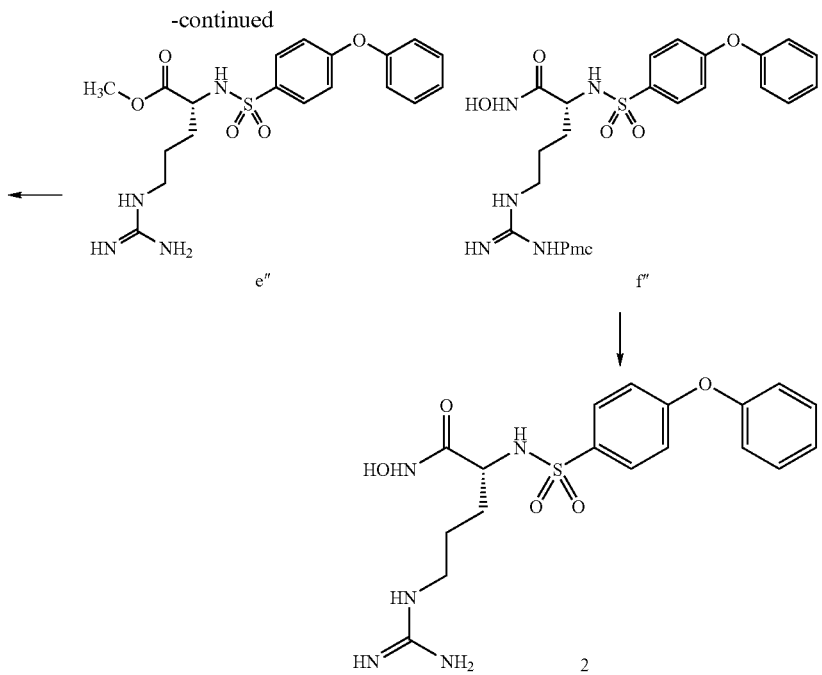

Sulfonamide c"

To a round bottom flask equipped with a magnetic stir bar was added H-D Arginine(Pmc)-OH (60.0 g, 136.4 mmol, 1.0 eq.), dry $CH_2Cl_2$ (1000 mL), 4-phenoxy benzene sulfonyl chloride (b") (36.4 g, 136 mmol, 1.0 eq.), and triethyl amine (75.0 mL, 542.4 mmol, 4.0 eq.). Trimethyl silyl chloride (34.2 mL, 271 mmol, 2.0 eq.) was then dropwise to the stirring reaction. The reaction was then allowed to stir at rt for an additional 3 h before concentrating via rotary evaporation. The solid residue was then dissolved in 300 mL of saturated $NaHCO_3$ and 300 mL $H_2O$. The aqueous layer was then washed twice with ether (200 mL), acidified with 2N HCl (200 mL), and extracted 3× with EtOAc. The combined EtOAc layers were then dried with $Na_2SO_4$, concentrated and dried on high vacuum overnight to give Sulfonamide c" as a white foam (90.0 g, 98% yield): LC/MS Calcd for $[M+H]^+$ 673.0, found 673.2.

Methyl Ester d"

To a round bottom flask equipped with a magnetic stir bar was added crude Sulfonamide c" (45.0 g, 67.0 mmol, 1.0 eq.), dry MeOH (500 mL), and Trimethyl silyl chloride (13.2 mL, 100 mmol, 1.5 eq.). The reaction was then refluxed under nitrogen for 4 h, cooled to rt, and concentrated via rotary evaporation. Water (200 mL) and saturated $NaHCO_3$ (20 mL) were added to the solid residue, and the aqueous layer was extracted 3× with EtOAc (200 mL), dried with $Na_2SO_4$, concentrated and further dried on high vacuum overnight to give Methyl Ester d" as a pale yellow foam (43.0 g, 93.5% yield): LC/MS Calcd for $[M+H]^+$ 687.0, found 687.2.

Guanidine e"

To a round bottom flask was added crude Methyl Ester d" (32.0 g, 46.6 mmol), 1:1 TFA:$CH_2Cl_2$ (500 mL), and triethyl silane (5.0 mL). The reaction was allowed to sit at rt for 90 min before concentrating via rotary evaporation. The residual TFA was then removed via azeotroping with toluene. The oil was then triturated 3× with ether (125 mL) to give crude guanidine e" as a white solid. Guanidine e" was then dissolved in 50 mL of EtOAc, concentrated via rotary evaporation, and triturated again 2× with ether (50 mL). Drying of crude guanidine e" on high vacuum overnight afforded a yellow brown foam, which was then rinsed 2× with ether (100 mL), and dried on high vacuum, yielding guanidine e" as a yellow foam which was taken on crude to the next step. LC/MS Calcd for $[M+H]^+$ 421.0, found 421.1.

Hydrochloride salt of $N^1$-hydroxy-$N^2$-[(4-phenoxyphenyl)sulfonyl]-D-argininamide To a round bottom flask was added to the above crude Guanidine e" (19.0 g, 45.2 mmol, 1.0 eq.), and freshly made 1.76 M $HONH_2$ in MeOH (380 mL, 668.8 mmol, 14.8 eq.). The reaction was allowed to sit at rt overnight before filtering off the precipitate, and concentrating the supernatant to one fourth the original volume. The supernatant was then neutralized to pH 7.0 dropwise with neat TFA, concentrated via rotary evaporation, and triturated with ether (100 mL). Crude EXEL-00987124 was then dissolved in 60 mL of 20:80 acetonitrile:water and purified via three 20 mL injections on a Varian Prep HPLC system: gradient=15% B to 70% B in 40 min where A=100% water, 0.1% TFA, and B=100% acetonitrile, 0.1% TFA; flow rate=160 mL/min, fraction size=100 mL. Each fraction was analyzed on analytical HPLC, and LC/MS. Pure fractions were combined, lyophilized, HCl exchanged with 1N HCl 3×, and water exchanged 1× to give pure $N^1$-hydroxy-$N^2$-[(4-phenoxyphenyl)sulfonyl]-D-argininamide as a white solid (6.8 g, 35.9% yield). Mixed fractions contaminated with a small impurity were also collected in a separate flask and repurified (2.0 g, 10.5% yield). LC/MS Calcd for $[M+H]^+$ 422.0, found 422.1; $^1$HNMR (400 MHz, MeOD): δ 7.81 (dt, J=8.8, 3.2 Hz, 2H), 7.42 (t, J=7.4 Hz, 2H), 7.22 (t, J=7.4 Hz, 1H), 7.1 (d, J=8.4 Hz, 2H), 7.05 (d, J=8.8 Hz, 2H), 3.65 (t, J=7.6 Hz, 1H), 3.15 (t, J=6.4 Hz, 2H), 1.51-1.69 (m, 4H).

Hydroxamic Acid f"

To a round bottom flask was added methyl ester d" (46.0 g, 67.0 mmol, 1.0 eq.) and freshly prepared 1.76 M $HONH_2$ in MeOH (152.0 mL, 268 mmol, 4.0 eq.). The reaction was allowed to sit at rt for 3 h before adding another 152 mL of 1.76M HONH$_2$. The reaction was continued for another 4 h before quenching with 1N HCl (250 mL) to a pH of 5.0. The methanol was evaporated and the water was decanted from the residual solid crude product. The crude hydroxamic acid f'' was purified in two batches (approximately 25 g each batch) by dissolving in EtOAc, and dry loading onto a Biotage FLASH 75 L pre-packed cartridge, and eluted with 100% EtOAc to afford pure hydroxamic acid f'' as an orange solid (34.7 g, 75% yield). LC/MS Calcd for [M+H]$^+$ 688.0, found 688.2

Hydrochloride salt of N$^1$-hydroxy-N$^2$-[(4-phenoxyphenyl)sulfonyl]-D-argininamide To a round bottom flask was added hydroxamic acid f'' (19.7 g, 46.9 mmol), 1:1 TFA:CH$_2$Cl$_2$ (400 mL), and triethyl silane (4.0 mL). The reaction was stirred at rt for 90 min, and concentrated via rotary evaporation. The residual TFA was then removed via azeotroping with toluene. The oil was then triturated 3× with ether (125 mL) to give crude 2 as a brown solid. The solid was then dissolved in 40 mL of 20:80 acetonitrile:water and purified via two 20 mL injections on a Varian Prep HPLC system: gradient=15% B to 70% B in 40 min where A=100% water, 0.1% TFA, and B=100% acetonitrile, 0.1% TFA; flow rate=160 mL/min, fraction size=100 mL. Each fraction was analyzed on analytical HPLC, and LC/MS. Pure fractions were combined, lyophilyzed, HCl exchanged with 1N HCl 3×, and water exchanged 1× to give pure N$^1$-hydroxy-N$^2$-[(4-phenoxyphenyl)sulfonyl]-D-argininamide as a white solid (5.2 g, 26.3% yield). Mixed fractions contaminated with a small impurity were also collected in a separate flask and repurified (1.4 g, 7.2% yield). LC/MS Calcd for [M+H]$^+$ 422.0, found 422.1; $^1$HNMR (400 MHz, MeOD): δ 7.81 (dt, J=8.8, 3.2 Hz, 2H), 7.42 (t, J=7.4 Hz, 2H), 7.22 (t, J=7.4 Hz, 1H), 7.1 (d, J=8.4 Hz, 2H), 7.05 (d, J=8.8 Hz, 2H), 3.65 (t, J=7.6 Hz, 1H), 3.15 (t, J=6.4 Hz, 2H), 1.51-1.69 (m, 4H).

Example 8

General Experimental Procedures for the Synthesis of Cyanoguanidines

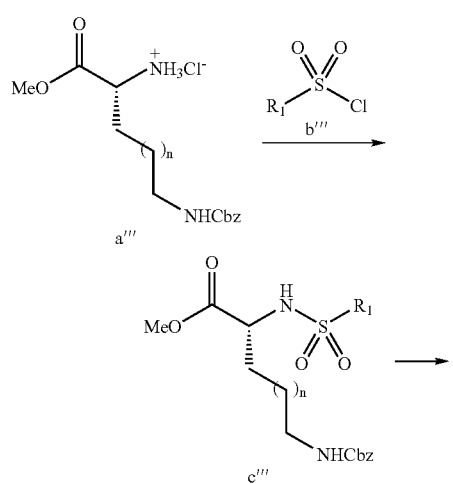

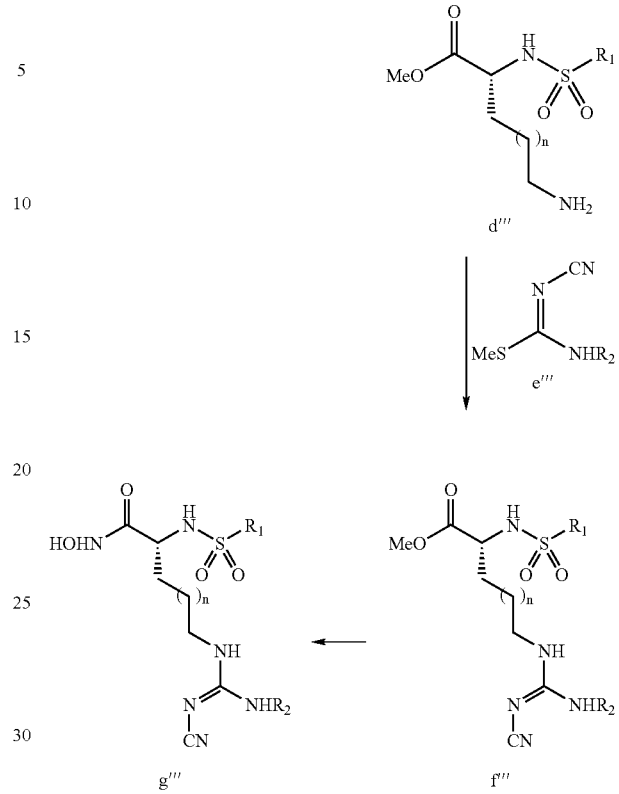

Sulfonamide c'''

To a round bottom flask equipped with a magnetic stirrer was added Methylester a''' (17.0 mmol, 1.0 eq.), dry CH$_2$Cl$_2$ (170 mL), Sulfonyl Chloride b''' (18.5 mmol, 1.1 eq.), and 2,6-lutidine (42.5 mmol, 2.5 eq.). The reaction was stirred at rt for 5 h before quenching with H$_2$O (100 mL) and saturated NH$_4$Cl (20 mL). The aqueous layer was extracted 3× with EtOAc (100 mL), and the combined organic layers were dried with Na$_2$SO$_4$ before concentrating to give crude sulfonamide c''' as a clear oil. Trituration with 20:80 EtOAc:Hexanes, followed by drying on high vacuum then affords relatively pure sulfonamide c''' as a white solid that can be taken on directly to the next step.

Amine d'''

To a round bottom flask equipped with a magnetic stir bar was added Sulfonamide c''' (1.14 mmol), dry MeOH (20.0 mL), dry CH$_2$Cl$_2$ (3.0 mL) and 10% Pd/C (120 mg). The reaction was stirred at rt over an atmosphere of hydrogen for 5 h before filtering over a pad of celite and rinsing 3× with EtOAc. The washes were combined and concentrated to give crude amine d''' as a clear oil which can be taken directly onto the next step.

Cyanoguanidine f'''

To a round bottom flask equipped with a magnetic stir bar was added amine d''' (1.14 mmol, 1.0 eq.), dry DMF (6.0 mL), dry triethylamine (6.0 mL), thiomethylcyanoguanidine e''' (1.14 mmol, 1.0 eq.), and AgNO$_3$ (1.23 mmol, 1.1 eq.). The brown slurry was stirred at rt overnight in the absence of light before filtering out the brown precipitate. The filtrate was concentrated and placed on high vacuum to remove any residual DMF. Crude cyanoguanidine f''' was then purified via silica gel chromatography.

Hydroxamic Acid g'''

To a round bottom flask was added cyanoguanidine f''' (0.47 mmol, 1.0 eq.) and freshly prepared 1.76 M HONH$_2$ (1.9 mmol, 4.0 eq.). The reaction was stirred at rt for 1 h before adding another 1.0 mL of 1.76 M HONH$_2$. After stirring for an additional 3 h, the reaction was neutralized to a pH of 7.0 with 1N HCl. (Care was taken during the neutralization such that the pH was never below 7.0 to prevent cyanoguanidine conversion to the urea.) Silica gel chromatography then afforded pure hydroxamic acid g'''. Alternatively, hydroxamic acid g''' can be purified via prep HPLC (solvent system=water/acetonitrile with 0.1% TFA), although fractions containing hydroxamic acid g''' must be neutralized with saturated NaHCO$_3$ prior to concentration to prevent hydrolysis of the cyanoguanidine to the corresponding urea).

In the case where R$_2$=H:

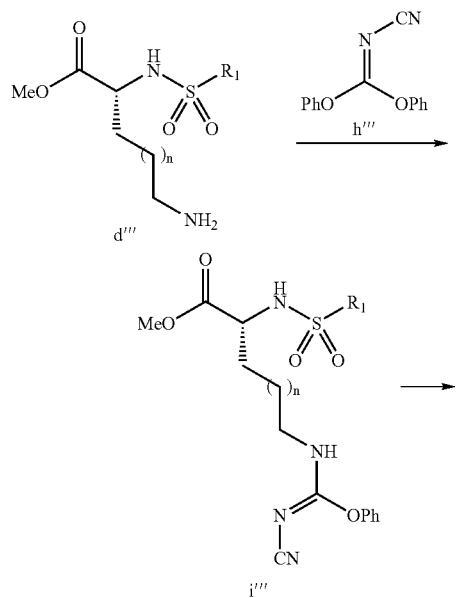

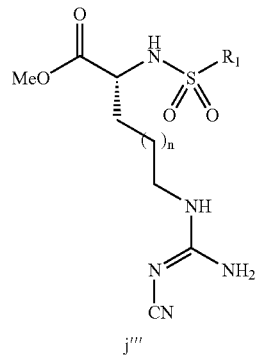

Cyanoimine i'''

To a round bottom flask equipped with a magnetic stir bar was added amine d''' (0.51 mmol, 1.0 eq.), isopropanol (3.0 mL), triethyl amine (0.51 mmol, 1.0 eq.), and diphenyl cyano carbonimidate (0.56 mmol, 1.1 eq.). The reaction was stirred at rt overnight, concentrated via rotary evaporation, and purified via silica gel chromatography.

Cyanoguanidine j'''

To a round bottom flask was added cyanoimine i''' (0.11 mmol), isopropanol (2.0 mL), and concentrated NH$_4$OH (1.0 mL). The reaction was stirred at rt overnight, and concentrated via rotary evaporation to afford crude cyanoguanidine j''' which can be carried onto the next step without further purification.

Example 9

Preparation of Sulfonamide Hydroxamates on Solid Support

General Procedure for the Sulfonamide Hydroxamate Synthesis on Solid Support:

General Procedure in Solid Phase Syntheses:

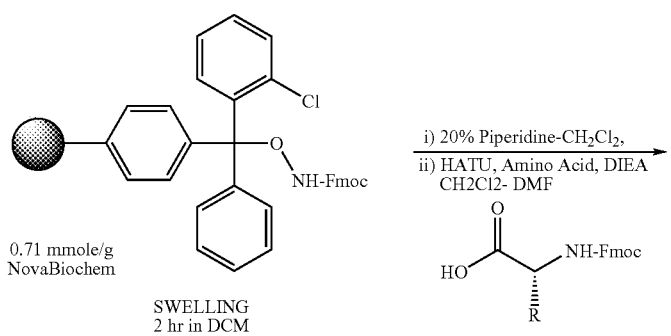

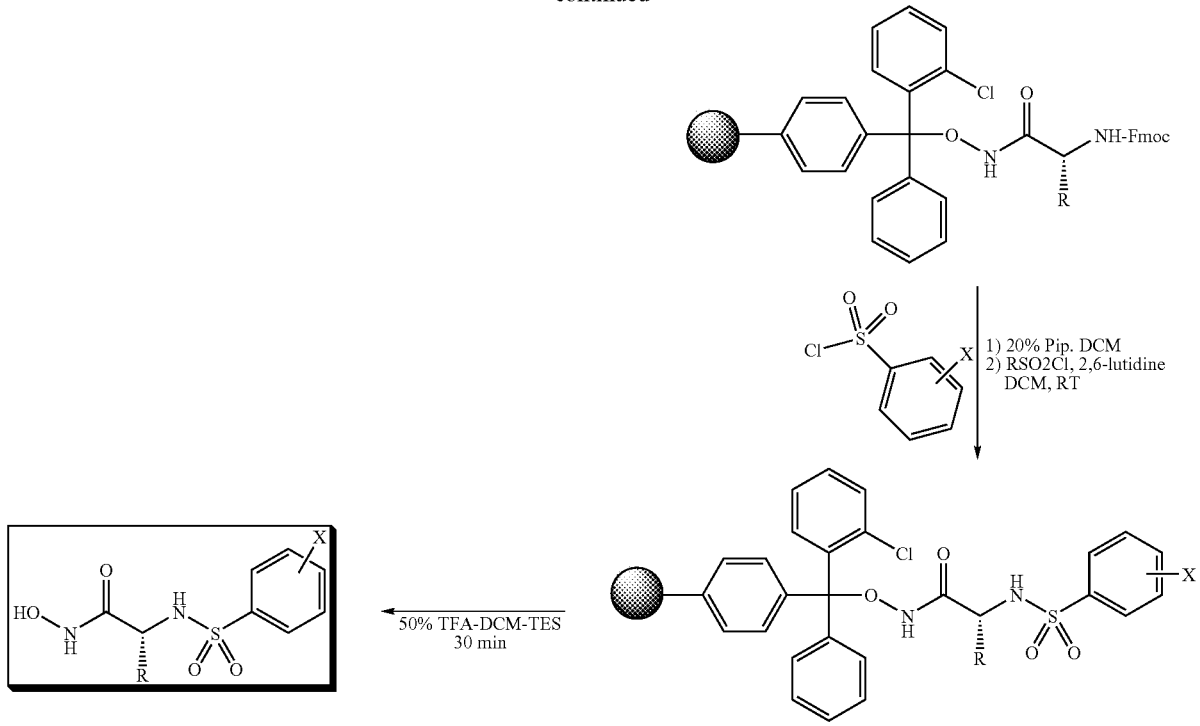

Fmoc Deprotection of Resin Bound N-(Fmoc)hydroxylamine:

2-Chlorotrityl polystyrene resin functionalized with N-(Fmoc)hydroxylamine (0.2 g, 0.154 mmole) was welling in dichloromethane (DCM). The resin was treated with 20% piperidine in DCM for 1 hr. After filtration the resin was washed with DCM then with methanol (MeOH) and DCM.

Amino Acid Coupling to O-(resin)hydroxylamine:

O-(resin)hydroxylamine (0.154 mmole) was treated with a solution of the appropriate N-(Fmoc) protected amino acid (2 eq.) in dimethylformamide (DMF)-DCM containing HATU (O(7-azabenzotriazol-1-yl)-N,N,N',N',-tetramethyluronium hexafluorophosphate, 2 eq.) and diisopropylethylamine (DIEA, 4 eq.). The resulting slurry was agitated for 13 hrs. The resin was filtered and washed with DMF, MeOH, and DC

α-N-Fmoc Deprotection of Resin Bound Amino Acid Hydroxylamine:

O-(resin)hydroxylamine-amino acid (α-N-Fmoc) (0.154 mmole) was treated with 20% piperidine in DCM. The resin was agitated for 1 hr then filtered, washed with DCM, MeOH and DCM.

Formation of Sulfonamide:

O-(resin)hydroxylamino-amino acid (0.154 mmole) was treated with appropriate sulfonyl chloride (2 eq.) containing 2,6-lutidine (2 eq.) in DCM for 13 hrs. The resin was filtered and washed with DCM, MeOH and DCM.

Compound Release from the Resin:

The α-N-substituted resin bound amino acid sulfonamide hydroxamate was treated with 20% Trifluoroacetic acid (TFA) containing 2% triethylsilane in DCM for 30 min. The resin filtered and evaporated to dryness then purified by semi-prep HPLC.

Following compounds are prepared using method described above: N-2-{[6-3-fluorophenyl)pyridin-3-yl]sulfonyl}-N-1-hydroxy-D-argininamide, N-1-hydroxy-N-2-[(4-phenoxyphenyl)sulfonyl]-D-argininamide, N-2-{[4-(4-fluorophenoxy)phenyl]sulfonyl}-N-1-hydroxy-D-argininamide, N-2-[(3-fluoro-4-phenoxyphenyl)sulfonyl]-N-1-hydroxy-D-argininamide, N-2-{[4-(4-chlorophenoxy)-3,5-difluorophenyl]sulfonyl}-N-1-hydroxy-D-argininamide, N-2-{[3,5-difluoro-4-(4-fluorophenoxy)phenyl]sulfonyl}-N-1-hydroxy-D-argininamide, and N-2-(1,1'-biphenyl-4-ylsulfonyl)-N-1-hydroxy-D-argininamide

Example 9

Preparation of Pyridylether Sulfonamide Hydroxamate on Solid Support

Formation of Pyridylarylether-Sulfonamide:

O-(resin)hydroxylamino-amino acid (0.154 mmole) was treated with 2-chloropyridyl sulfonyl chloride (2 eq.) containing 2,6-lutidine (2 eq.) in DCM for 13 hrs. The resin was filtered and washed with DCM, MeOH and DCM.

Formation of Pyridyl-Aryl Ether:

The α-N-substituted resin bound amino acid sulfonamide hydroxamate was treated with arylalcohol (10 eq.), cesium carbonate (5 eq.) in N-methylpyrrolidinone (NMP) at 80° C. for 13 hrs. The resin filtered and washed with DMF, MeOH, water, MeOH and DCM.

Compound Release from the Resin:

The α-N-substituted resin bound amino acid sulfonamide hydroxamate was treated with 20% Trifluoroacetic acid (TFA) containing 2% triethylsilane in DCM for 30 min. The resin filtered and evaporated to dryness then purified by semi-prep HPLC.

Following compounds are prepared using method described above:

N-1-hydroxy-N-2-{[6-(5,6,7,8-tetrahydronaphthalen-2-yloxy)pyridin-3-yl]sulfonyl}-D-argininamide
Series of Mono-fluoro aryl ether: 3,4-difluorosulfonyl chloride is used instead of 2-chloropyridyl sulfonyl chloride.

Example 10

Preparation of Pyridylether Sulfonamide Hydroxamate on Solid Support

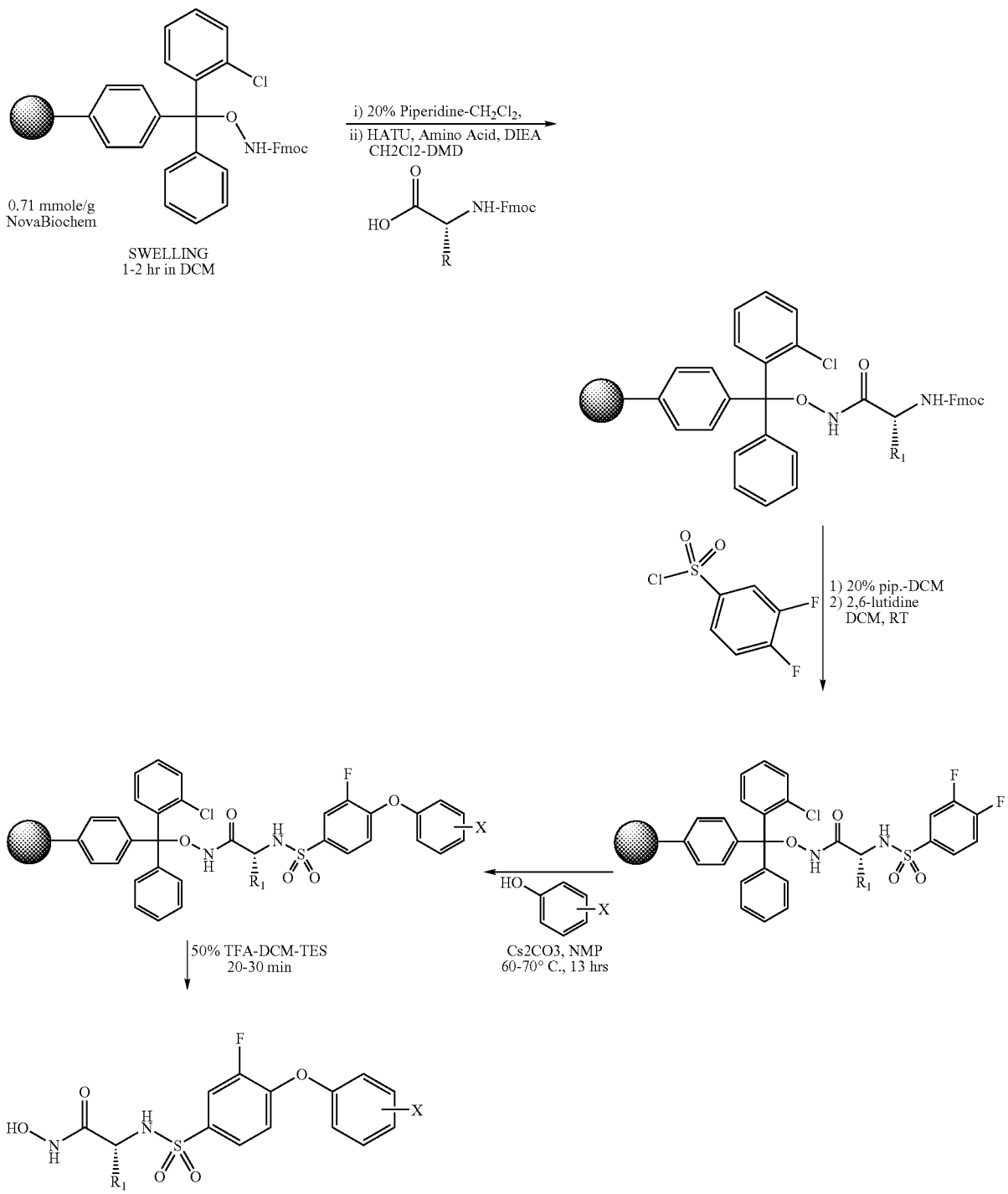

Following compounds are prepared using method described above:

N-2-[(3-fluoro-4-phenoxyphenyl)sulfonyl]-N-1-hydroxy-D-argininamide (4)

N-2-{[3-fluoro-4-(4-fluorophenoxy)phenyl]sulfonyl}-N-1-hydroxy-D-argininamide (9)

N-2-{[4-(4-chlorophenoxy)-3-fluorophenyl]sulfonyl}-N-1-hydroxy-D-argininamide (10)

N-2-([4-(4-cyanophenoxy)-3-fluorophenyl]sulfonyl)-N-1-hydroxy-D-argininamide (11)

N-2-{[4-(3,5-dimethylphenoxy)-3-fluorophenyl]sulfonyl}-N-1-hydroxy-D-argininamide (12)

The following, Table 2, provides some physical data for some of the compounds synthesized. The compound numbers in Table 2 correlate to compound numbers in Table 1.

TABLE 2

| Cmpd # | Calculated MWt | Observed MWt | Retention Time (min.) | |
|---|---|---|---|---|
| 1 | 424.4 | M + H = 425.1 | 1.1 | HP |
| 2 | 518.6 | M + H = 519.1 | 1.39 | HP |
| 3 | 536.577 | M + H = 537.1 | 1.31 | Shimadzu |
| 4 | 502.2 | M + H = 503.1 | 1.45 | HP |
| 5 | 463.5 | M + H = 464.1 | 1.25 | HP |
| 6 | 520.578 | M + H = 521.1 | 1.71 | Shimadzu |
| 7 | 460.5 | M + H = 461.1 | 1.35 | HP |
| 8 | 521.6 | M + H = 522.1 | 1.35 | HP |
| 9 | 469.4 | M + H = 470.0 | 1.25 | HP |
| 10 | 576.6 | M + H = 577.1 | 1.25 | HP |
| 11 | 466.5 | M + H = 467.0 | 1.32 | HP |
| 12 | 573.2 | M + H = 574.2 | 1.32 | HP |
| 14 | 512.513 | M + H = 513.1 | 1.32 | Shimadzu |
| 15 | 421.47 | M + H = 422.1 (100%) | 1.15 | HP |
| 16 | 457 | M + H = 458 | 1.28 | HP |
| 17 | 439.46 | M + H = 440.1 (100%) | 1.2 | HP |
| 18 | 473.9 | M + H = 474.0 (100%) | 1.3 | HP |
| 19 | 439.46 | M + H = 440.1 (100%) | 1.25 | HP |
| 20 | 505.6 | M + H = 506.2 | 1.4 | HP |
| 21 | 548.588 | M + H = 549.1 | 1.51 | Shimadzu |
| 22 | 457.12 | M + H = 458.1 | 1.38 | HP |
| 23 | 464 | M + H = 465 | 1.25 | HP |
| 24 | 566.57 | M + H = 567.1 (100%) | 1.4 | HP |
| 25 | 491.89 | M + H = 492.1 (100%) | 1.32 | HP |
| 26 | 467.51 | M + H = 468.1 (100%) | 1.31 | HP |
| 28 | 405.47 | M + H = 406.1 (100%) | 1.46 | HP |
| 29 | 575.56 | M + H = 576 | 1.22 | HP |
| 30 | 449.52 | M + H = 450.1 (100%) | 1.21 | HP |
| 31 | 476.55 | M + H = 477.1 (100%) | 1.32 | HP |
| 32 | 535.03 | M + H = 536.0 | 1.39 | HP |
| 33 | 467.5 | M + H = 468.14 | 1.793 | Shimazu |
| 34 | 528.6 | M + H = 529 | 1.45 | HP |
| 35 | 466 | M + H = 467.1 | 1.15 | HP |
| 36 | 544.62 | M + H = 545 | 1.59 | HP |
| 37 | 598.6 | M + H = 599 | 1.48 | HP |
| 38 | 563.61 | M + H = 564.1 (100%) | 1.5 | HP |
| 39 | 463.54 | M + H = 464.2 (100%) | 1.32 | HP |
| 40 | 559.6 | M + H = 598.0 (M + K, 100%) | 1.44 | HP |
| 41 | 576.05 | M + H = 614.0 (M + K, 100%) | 1.6 | HP |
| 42 | 479.526 | M + H = 480.1 | 1.34 | Shimadzu |
| 43 | 562.64 | M + H = 563 | 1.25 | HP |
| 44 | 503.5 | M + H = 504.1 | 1.37 | HP |
| 45 | 481.538 | M + H = 482.1 | 1.27 | HP |
| 46 | 481.53 | M + H = 482.1 (100%) | 1.23 | HP |
| 47 | 517.519 | M + H = 518.1 | 1.42 | Shimadzu |
| 48 | 533.973 | M + H = 534.1 | 1.39 | HP |
| 49 | 545.62 | M + H = 546.1 (100%) | 1.45 | HP |
| 50 | 475.11 | M + H = 476.1 | 1.33 | HP |

Table 3 shows proton NMR data for selected compounds:

TABLE 3

| Entry | Name | $^1$H-NMR |
|---|---|---|
| 1 | $N^1$-hydroxy-$N^2$-{[4-(phenyloxy)phenyl]sulfonyl}-D-lysinamide | H-NMR; δ(CD3OD): 7.79(d, 2H), 7.42(t, 2H), 7.22(t, 1H), 7.09(d, 2H), 7.05(d, 2H), 3.63(t, 1H), 2.87(t, 2H), 1.57-1.68(m, 4H), 1.44(m, 1H), 1.37(m, 1H) |
| 2 | $N^1$-hydroxy-$N^2$-{[4-(phenyloxy)phenyl]sulfonyl}-3-piperidin-3-ylalaninamide | H-NMR; δ(CD3OD): 7.79(q, 2H), 7.42(t, 2H), 7.22(t, 1H), 7.10(d, 2H), 7.05(d, 2H), 3.72(m, 1H), 3.23-3.47(m, 2H), 2.87(m, 1H), 2.64(t, 1H), 1.83-2.01(m, 3H), 1.17-1.74(m, 4H) |
| 3 | $N^1$-hydroxy-$N^2$-{[4-(phenyloxy)phenyl]sulfonyl}-3-pyrrolidin-3-ylalaninamide | H-NMR; δ(CD3OD): 7.80(d, 2H), 7.42(t, 2H), 7.22(t, 1H), 7.10(d, 2H), 7.06(d, 2H), 3.72(q, 2H), 2.22-2.3(m, 1H), 1.96-2.18(m, 4H), 1.83(m, 1H), 1.65(m, 1H) |
| 4 | $N^2$-{[6-(3-fluorophenyl)pyridin-3-yl]sulfonyl}-$N^1$-hydroxy-D-lysinamide | (CD$_3$OD) 9.21(br. s, 1H), 9.01(d, 1H), 8.24(dd, 1H), 8.04(d, 1H), 7.92(dd, 1H), 7.88(dt, 1H), 7.54(m, 1H), 7.22(td, 1H), 3.72(t, 1H), 3.20(br. q, 2H), 1.65(m, 2H), 1.53(m, 2H), 1.45(m, 2H) ppm |
| 5 | N-hydroxy-N-{[4-(phenyloxy)phenyl]sulfonyl}-D-tryptophanamide | H-NMR; δ(CD3OD): 7.50(d, 2H), 7.42(m, 3H), 7.32(d, 1H), 7.24(m, 2H), 7.06(m, 2H), 6.99(s, 1H), 6.94(t, 1H), 6.76(d, 1H), 6.64(d, 1H), 3.84(t, 1H), 3.13(q, 1H), 2.87(q, 1H) |
| 6 | $N^1$-hydroxy-$N^2$-({5-[2-(methylthio)pyrimidin-4-yl]-2-thienyl}sulfonyl)lysinamide | H-NMR; δ(CD3OD): 8.6(d, 1H), 7.9(d, 1H), 7.6(d, 1H), 7.58(d, 1H), 3.8(t, 1H), 2.9(t, 2H), 2.6(s, 3H), 1.6-1.75(m, 4H), 1.5(m, 1H), 1.4(m, 1H) |

TABLE 3-continued

| Entry | Name | $^1$H-NMR |
|---|---|---|
| 7 | N-hydroxy-N-{[4-(phenyloxy)phenyl]sulfonyl}-D-histidinamide | H-NMR; δ(CD3OD): 8.78(s, 1H), 7.74(d, 2H), 7.43(t, 2H), 7.31(s, 1H), 7.23(t, 1H), 7.10(d, 2H), 7.02(d, 2H), 3.94(q, 1H), 2.96-3.12(q, 2H) |
| 8 | $N^1$-hydroxy-$N^2$-methyl-$N^2$-{[4-(phenyloxy)phenyl]sulfonyl}-3-piperidin-3-ylalaninamide | H-NMR; δ(CD3OD): 7.75(m, 2H), 7.42(m, 2H), 7.23(m, 1H), 7.01-7.12(m, 4H), 3.34(m 1H), 3.30(s, 3H), 2.82-3.00(m, 3H), 2.63-2.71(m, 1H), 1.85-2.06(m, 9H) |
| 9 | $N^1$-hydroxy-$N^2$-{[4-(phenyloxy)phenyl]sulfonyl}-3-piperidin-4-ylalaninamide | H-NMR; δ(CD3OD): 7.80(d, 2H), 7.43(t, 2H), 7.22(t, 1H), 7.10(d, 2H), 7.05(d, 2H), 3.71(q, 1H), 3.35(d, 1H), 2.91(dt, 2H), 1.89(d, 2H), 1.24-1.76(m, 6H) |
| 10 | $N^1$-hydroxy-$N^2$-{[4-(phenyloxy)phenyl]sulfonyl}-3-pyridin-3-yl-D-alaninamide | H-NMR; δ(CD3OD): 8.71(d, 1H), 8.64(s, 1H), 8.34(d, 1H), 7.91(q, 1H), 7.79(d, 1H), 7.69(d, 2H), 7.43(t, 2H), 7.23(t, 1H), 7.10(d, 2H), 7.00(d, 2H), 3.94(q, 1H), 3.18(q, 1H), 3.05(q, 1H) |
| 11 | $N^6$-glycyl-$N^1$-hydroxy-$N^2$-{[4-(phenyloxy)phenyl]sulfonyl}-D-lysinamide | H-NMR; δ(CD3OD): 7.79(d, 2H), 7.42(t, 2H), 7.22(t, 1H), 7.10(d, 2H), 7.05(d, 2H), 3.64(s, 2H), 3.60(t, 1H), 3.19(m, 2H), 1.60(m, 2H), 1.48(m, 2H), 1.34(m, 2H) |
| 12 | $N^1$-hydroxy-$N^2$,$N^6$,$N^6$-trimethyl-$N^2$-{[4-(phenyloxy)phenyl]sulfonyl}-D-lysinamide | H-NMR; δ(CD3OD): 7.80(d, 2H), 7.42(m, 2H), 7.22(t, 1H), 6.96-7.10(m, 4H), 3.66(t, 1H), 3.30(m, 2H), 3.11(s, 9H), 1.75-1.85(m, 2H), 1.69(q, 2H), 1.36-1.50(m, 2H) |
| 13 | 3-[4-(aminomethyl)cyclohexyl]-$N^1$-hydroxy-$N^2$-{[4-(phenyloxy)phenyl]sulfonyl}alaninamide | H-NMR; δ(CD3OD): 7.80(d, 2H), 7.42(m, 2H), 7.22(t, 1H), 7.10(d, 2H), 7.05(d, 2H), 3.67(q, 1H), 2.99(m, 1H), 1.99(m, 2H), 1.79(m, 2H), 1.54(t, 1H), 1.35-1.42(m, 3H), 1.26(m, 1H), 1.06(q, 1H), 0.96(q, 1H) |
| 14 | $N^1$-hydroxy-$N^2$-{[6-(naphthalen-1-yloxy)pyridin-3-yl]sulfonyl}-D-argininamide | H-NMR; δ(CD$_3$OD): 8.46(br. d, 1H), 8.18(d, 1H), 7.95(d, 1H), 7.84(m, 2H), 7.50(m, 3H), 7.30(d, 1H), 7.18(d, 1H), 3.54(br. t, 1H), 3.04(br. t, 2H), 2.50(m, 1H), 1.8(m, 3H) ppm. |
| 17 | $N^6$-[(E)-(cyanoimino)(hydroxyamino)methyl]-$N^2$-({4-[(4-fluorophenyl)oxy]phenyl}sulfonyl)-$N^1$-hydroxy-D-lysinamide | H-NMR; δ(CD3OD): 7.78(d, 2H), 7.14(m, 4H), 7.01(d, 2H), 3.56(t, 1H), 1.47(m, 4H), 1.37(m, 2H), 1.19(m, 2H) |
| 18 | $N^2$-({4-[(4-fluorophenyl)oxy]phenyl}sulfonyl)-$N^1$-hydroxy-D-lysinamide | H-NMR; δ(CD3OD): 7.67(d, 2H), 7.04(m, 4H), 6.92(d, 2H), 3.52(t, 1H), 1.53(m, 4H), 1.38(m, 2H), 1.25(m, 2H) |
| 19 | $N^6$-{(Z)-(cyanoimino)[(2-morpholin-4-ylethyl)amino]methyl}-$N^2$-{[6-(3-fluorophenyl)pyridin-3-yl]sulfonyl}-$N^1$-hydroxy-D-lysinamide | H-NMR; δ(CD$_3$OD) 9.01(br. s, 1H), 8.26(d, 1H), 8.06(d, 1H), 7.89(dd, 2H), 7.52(br. q, 1H), 7.24(br. t, 1H), 3.72(m, 4H), 3.32(m, 4H), 3.15(br. t, 2H), 2.52(m, 6H), 1.3-1.8(m, 5H) ppm. |
| 20 | $N^2$-({6-[(4-fluorophenyl)oxy]pyridin-3-yl}sulfonyl)-$N^1$-hydroxy-D-argininamide | H-NMR; δ(CD$_3$OD) 8.45(br. s, 1H), 8.19(br s, 1H), 7.20(m, 5H), 3.65(br. s, 1H), 3.25(m, 4H), 1.65(m, 3H) ppm |
| 21 | $N^2$-({6-[(4-chlorophenyl)oxy]pyridin-3-yl}sulfonyl)-$N^1$-hydroxy-D-argininamide | H-NMR; δ(CD$_3$OD): 8.45(d, 1H), 8.19(dd, 1H), 7.42(d, 2H), 7.19(dd, 3H), 3.85(br. t, 1H), 3.20(m, 2H), 1.80(m, 4H) ppm |
| 22 | $N^2$-({3,5-difluoro-4-[(4-fluorophenyl)oxy]phenyl}sulfonyl)-$N^1$-hydroxy-$N^6$-(morpholin-4-ylcarbonyl)-D-lysinamide | H-NMR; δ(CD3OD): 7.52(d, 2H), 6.95(d, 2H), 6.91(m, 2H), 3.26 m, 5H), 3.22(4H, m), 3.04(m, 2H), 1.54(m, 2H), 1.40(m, 2H), 1.25(m, 2H) |
| 23 | 4-cyano-N-hydroxy-N-{[4-(phenyloxy)phenyl]sulfonyl}-D-phenylalaninamide | H-NMR; δ(CD3OD): 7.4(m, 4H), 7.28(m, 1H), 7.25(s, 2H), 7.05(m, 4H), 6.78(M, 2H), 4.03(m, 1H), 3.10(m, 1H), 2.85(m, 1H) |
| 25 | 3-cyano-N-({3,5-difluoro-4-[(4-fluorophenyl)oxy]phenyl}sulfonyl)-N-hydroxy-D-phenylalaninamide | H-NMR; δ(CDCl3): 7.1-7.4(m, 6H), 6.94(m, 2H), 6.84(m, 2H), 4.2(m, 1H), 3.0-3.3(m, 2H) |
| 26 | 3-cyano-N-hydroxy-N-{[4-(phenyloxy)phenyl]sulfonyl}-D-phenylalaninamide | H-NMR; δ(CDCl3): 7.42(m, 2H), 7.39(t, 2H), 7.34(d, 1H), 7.26(m, 1H), 7.21(t, 2H), 7.15(m, 1H), 7.04(d, 2H), 6.74(d, 2H), 4.1(m, 1H), 3.2(m, 1H), 2.9(m, 1H) |

TABLE 3-continued

| Entry | Name | $^1$H-NMR |
|---|---|---|
| 27 | $N^2$-({3,5-difluoro-4-[(4-hydroxyphenyl)oxy]phenyl}sulfonyl)-$N^1$-hydroxyargininamide | H-NMR: δ(CD3OD): 7.6(d, 2H), 6.8(d, 2H), 6.7(d, 2H), 3.7(t, 1H), 3.2(t, 2H), 1.6-1.8(m, 4H) |
| 28 | $N^2$-{[3,5-difluoro-4-(pyridin-3-yloxy)phenyl]sulfonyl}-$N^1$-hydroxyargininamide | H-NMR: δ(CD3OD): 8.5(s, 1H), 8.4(s, 1H), 7.62(d, 2H), 7.5(m, 2H), 3.7(t, 1H), 3.2(t, 2H), 1.7(m, 4H) |
| 30 | $N^2$-({3,5-difluoro-4-[(4-fluorophenyl)oxy]phenyl}sulfonyl)-$N^6$-[1-(4,4-dimethyl-2,6-dioxocyclohexylidene)ethyl]-$N^1$-hydroxy-D-lysinamide | H-NMR: δ(CD$_3$OD) 7.60(d, 2H), 7.05(m, 4H), 3.65(t, 1H), 3.45(t, 1H), 2.60(s, 3H), 2.40(s, 3H), 1.65(m, 4H), 1.45(m, 3H), 1.0(s, 4H) ppm |
| 31 | $N^2$-{[3,5-difluoro-4-({4-[(phenylmethyl)oxy]phenyl}oxy)phenyl]sulfonyl}-$N^1$-hydroxyargininamide | H-NMR: δ(CD3OD): 7.6(d, 2H), 7.4(d, 2H), 7.35(m, 2H), 6.9(s, 5H), 5.02(s, 2H), 3.65(t, 1H), 3.1(t, 2H), 1.7(m, 4H) |
| 32 | $N^2$-{[3,5-difluoro-4-(pyridin-3-yloxy)phenyl]sulfonyl}-$N^1$-hydroxy-6-morpholin-4-yl-D-norleucinamide | H-NMR: δ(CD3OD): 1.3-1.5(m, 2H), 1.5-1.7(m, 4H), 1.99(s, 3H), 2.57(t, 2H), 2.70(br s, 4H), 3.68(t, 1H), 3.76(t, 4H), 7.43(d, 1H), 7.63(d, 2H), 8.33(dd, 1H), 8.42(d, 1H |
| 33 | $N^2$-({3-fluoro-4-([4-fluorophenyl)oxy]phenyl}sulfonyl)-$N^1$-hydroxy-3-morpholin-4-yl-D-alaninamide | H-NMR: δ(CD$_3$OD): 7.70(m, 2H), 7.10(m, 5H), 3.80(br. t, 2H), 3.20(m, 6H) ppm |
| 34 | N-({3,5-difluoro-4-[(4-fluorophenyl)oxy]phenyl}sulfonyl)-N-hydroxy-4-[(hydroxyamino)(Imino)methyl]-D-phenylalaninamide | H-NMR: δ(CD$_3$OD): 7.61(d, 2H), 7.49(m, 4H), 7.01(m, 4H), 3.90(dd, 1H), 3.00(m, 2H) ppm |
| 36 | N-({3,5-difluoro-4-[(4-fluorophenyl)oxy]phenyl}sulfonyl)-N-hydroxy-3-[(hydroxyamino)(imino)methyl]-D-phenylalaninamide | H-NMR: δ(CD$_3$OD): 7.54(m, 6H), 7.02(m, 4H), 3.94(t, 1H), 3.01(m, 2H) ppm |
| 37 | $N^2$-({4-[(4-chlorophenyl)oxy]-3,5-difluorophenyl}sulfonyl)-$N^1$-hydroxy-3-[1-(morpholin-4-ylcarbonyl)piperidin-4-yl]alaninamide | H-NMR: δ(CDCl3): 7.54(d, 2H), 7.23(d, 2H), 6.85(d, 2H), 3.98(m, 1H), 3.63(br, 4H), 3.21(br, 2H), 2.81(m, 1H), 2.66(m, 1H), 1.60(br, 2H), 1.10(m, 1H) |
| 38 | $N^2$-({3,5-difluoro-4-[(4-fluorophenyl)oxy]phenyl}sulfonyl)-$N^1$-hydroxy-3-[1-(morpholin-4-ylcarbonyl)piperidin-4-yl]alaninamide | H-NMR: δ(DMSO-d6): 10.65(s, 1H), 8.45(d, 1H), 7.62(d, 2H), 7.18(d, 2H), 7.10(d, 2H), 3.64(m, 1H), 3.54(m, 4H), 3.08(m, 2H), 2.63(m, 1H), 2.49(m, 1H), 1.53(m, 1H), 1.38(m, 1H), 1.0(m, 1H) |
| 39 | 3-[amino(imino)methyl]-N-({3,5-difluoro-4-[(4-fluorophenyl)oxy]phenyl}sulfonyl)-N-hydroxy-D-phenylalaninamide | H-NMR: δ(CD$_3$OD): 7.58(m, 6H), 6.99(m, 4H), 3.88(t, 1H), 3.01(m, 2H) ppm |
| 40 | 4-[amino(imino)methyl]-N-({3,5-difluoro-4-[(4-fluorophenyl)oxy]phenyl}sulfonyl)-N-hydroxy-D-phenylalaninamide | H-NMR: δ(CD$_3$OD): 7.75(d, 2H), 7.50(d, 4H), 7.01(m, 4H), 3.90(dd, 1H), 3.05(m, 2H) ppm. |
| 41 | $N^5$-(aminocorbonyl)-N~2~-({3-fluoro-4-[(4-fluorophenyl)oxy]phenyl}sulfonyl)-$N^1$-hydroxy-D-ornithinamide | H-NMR: δ(CD$_3$OD): 7.65(d, 1H), 7.60(d, 1H), 7.10 (m, 5H), 3.82(t, 1H), 3.05(m, 2H), 1.60(m, 4H) ppm |
| 42 | (2R)-2-[({4-[(4-chlorophenyl)oxy]-3,5-difluorophenyl}sulfonyl)amino]-4-(dimethylamino)-N-hydroxybutanamide | H-NMR: δ(CD3OD): 1.97(q, 2H), 2.11(q, 2H), 2.78(s, 6H), 3.71(t, 1H), 6.90(dd, 2H), 7.21(d, 2H), 7.51(dd, 2H) |
| 43 | (2R)-2-[({4-[(4-chlorophenyl)oxy]-3,5-difluorophenyl}sulfonyl)amino]-4-{[1-(4,4-dimethyl-2,6-dioxocyclohexylidene)-2-methylbutyl]amino}-N-hydroxybutanamide | H-NMR: δ(CD3OD): 7.61(d, 2H), 7.31(d, 2H), 7.00(d, 2H), 3.77(t, 1H), 3.64(t, 2H), 3.04(m, 2H), 2.38(s, 4H), 1.97(m, 3H), 0.99-1.02(m, 12H) |
| 44 | $N^2$-({4-[(4-chlorophenyl)oxy]-3,5-difluorophenyl}sulfonyl)-$N^1$-hydroxy-3-[(2-morpholin-4-yl-2-oxoethyl)thio]-D-valinamide | H-NMR: δ(CD$_3$OD): 7.60(d, 2H), 7.30(m, 2H), 7.00(d, 2H), 3.80(m, 10H), 1.40(d, 6H) ppm |
| 45 | (2R)-4-amino-2-[({4-[(4-chlorophenyl)oxy]-3,5-difluorophenyl}sulfonyl)amino]-N-hydroxybutanamide | H-NMR: δ(CD3OD): 7.62(d, 2H), 7.32(d, 2H), 7.01(d, 2H), 3.79(t, 1H), 3.08(m, 1H), 2.98(m, 1H), 1.99(q, 2H) |
| 46 | (2R)-4-{[amino(imino)methyl]amino}-2-[({4-[(4-chlorophenyl)oxy]-3,5-difluorophenyl}sulfonyl)amino]-N-hydroxybutanamide | H-NMR: δ(CD3OD): 7.61(d, 2H), 7.32(d, 2H), 7.00(d, 2H), 3.80(t, 1H), 3.10(m, 1H), 2.98(m, 1H), 2.00(q, 2H) |

Example 11

Enzyme Assays mADAM-10 or hADAM-10 activity was measured as the ability to cleave a 10-residue peptide (DABCYL-Leu-Leu-Ala-Gln-Lys-*-Leu-Arg-Ser-Ser-Arg-EDANS). This peptide is based on the TNF-α cleavage site (Leu$^{62}$-Arg$^{71}$), however, we found that replacement of Ala$^{76}$-Val$^{77}$ with Lys-Leu resulted in a peptide with a 5-fold greater affinity for ADAM-10 than the native TNF-α peptide. Enzyme was diluted to a final active concentration of 5 nM in Buffer A (50 mM HEPES 8.0, 100 mM NaCl, 1 mM CaCl2 and 0.01% NP-40). Serial dilutions for compounds were performed ranging from 100 uM to 0.5 nM using a Beckman Biomek 2000 in polypropylene plates (Greiner). 20 µl of enzyme solution was added to 10 µl of compound in buffer A, and allowed to incubate for 15 min in 384 well black, Greiner, microtiter plates (#781076). 20 µl of substrate (12.5 uM in Buffer A) was then added, resulting in final reaction conditions of 2 nM ADAM-10, 5 µM substrate, and compound concentrations ranging from 20 uM to 0.1 nM. The reaction was incubated for 2 hr at RT, and fluorescence was measured at Ex355, Em460 on a Wallac Victor 2 fluorescence reader. For final analysis of potent inhibitors, a similar reaction was set up with a final active ADAM-10 concentration of 0.1 nM. This reaction was incubated for 16 hr at RT and fluorescence was read using identical conditions.

Table 4 below shows structure activity relationship data for selected compounds of the invention when tested in vitro with various metalloproteases. Inhibition is indicated as $IC_{50}$ with the following key: A=$IC_{50}$ less than 50 nM, B=$IC_{50}$ greater than 50 nM, but less than 1000 nM, C=$IC_{50}$ greater than 50 nM, but less than 20,000 nM, and D=$IC_{50}$ greater than 20,000 nM.

One aspect of the invention is the combination of, for example, guanidine-containing sidechains on an amino acid derived hydroximate; and substitution (particularly halo, more particularly fluoro) on the proximal ring (ring bonded directly to the sulfonamide moiety) of a two-ring-substituted sulfonamide derivative of the amino acid derived hydroximate. For example, by combining an arginine-derived hydroximate having a bis-aryl ether sulfonamide on the alpha-nitrogen, particularly when the proximal ring of the bis-aryl ether is substituted with, for example at least one fluorine, inhibitors that are selective for ADAM-10 are produced.

TABLE 4

| # | Compound Name | ADAM-10 $IC_{50}$ | MMP1 $IC_{50}$ | MMP2 $IC_{50}$ | MMP3 $IC_{50}$ | MMP8 $IC_{50}$ | MMP9 $IC_{50}$ | MMP13 $IC_{50}$ | TACE $IC_{50}$ |
|---|---|---|---|---|---|---|---|---|---|
| 1 | N$^1$-hydroxy-N$^2$-{[4-(phenyloxy)phenyl]sulfonyl}-D-lysinamide | A | B | C | A | | | A | B |
| 2 | N$^1$-hydroxy-N$^2$-{[4-(phenyloxy)phenyl]sulfonyl}-D-argininamide | A | C | A | B | A | A | A | B |
| 3 | N$^1$-hydroxy-N$^2$-{[4-(phenyloxy)phenyl]sulfonyl}-3-piperidin-3-ylalaninamide | A | B | A | A | | | A | A |
| 4 | N$^1$-hydroxy-N$^2$-{[4-(phenyloxy)phenyl]sulfonyl}-3-pyrrolidin-3-ylalaninamide | A | B | A | A | | | A | C |
| 5 | N$^2$-{[6-(3-fluorophenyl)pyridin-3-yl]sulfonyl}-N$^1$-hydroxy-D-lysinamide | A | C | A | B | | | A | C |
| 6 | N-hydroxy-N-{[4-(phenyloxy)phenyl]sulfonyl}-D-tryptophanamide | A | B | A | A | | | A | A |
| 7 | N$^1$-hydroxy-N$^2$-({5-[2-(methylthio)pyrimidin-4-yl]-2-thienyl}sulfonyl)lysinamide | B | D | A | C | | | A | C |
| 8 | N-hydroxy-N-{[4-(phenyloxy)phenyl]sulfonyl}-D-histidinamide | A | B | A | A | | | A | B |
| 9 | N$^1$-hydroxy-N$^2$-methyl-N$^2$-{[4-(phenyloxy)phenyl]sulfonyl}-3-piperidin-3-ylalaninamide | A | B | A | A | | | A | B |
| 10 | N$^1$-hydroxy-N$^2$-{[4-(phenyloxy)phenyl]sulfonyl}-3-piperidin-4-ylalaninamide | A | B | A | A | | | A | B |
| 11 | N$^1$-hydroxy-N$^2$-{[4-(phenyloxy)phenyl]sulfonyl}-3-pyridin-3-yl-D-alaninamide | A | D | A | A | | | A | A |
| 12 | N$^1$-hydroxy-6-morpholin-4-yl-N$^2$-{[4-(phenyloxy)phenyl]sulfonyl}-D-norleucinamide | A | B | A | A | | | A | C |
| 13 | N$^6$-glycyl-N$^1$-hydroxy-N$^2$-{[4-(phenyloxy)phenyl]sulfonyl}-D-lysinamide | A | A | A | | | | | B |
| 14 | N$^2$-{[6-(3-fluorophenyl)pyridin-3-yl]sulfonyl}-N$^1$-hydroxy-D-argininamide | A | B | A | B | | | A | C |
| 15 | N$^1$-hydroxy-N$^2$,N$^6$,N$^6$-trimethyl-N$^2$-{[4-(phenyloxy)phenyl]sulfonyl}-D-lysinamide | A | B | A | A | | | A | B |

TABLE 4-continued

| # | Compound Name | ADAM-10 IC$_{50}$ | MMP1 IC$_{50}$ | MMP2 IC$_{50}$ | MMP3 IC$_{50}$ | MMP8 IC$_{50}$ | MMP9 IC$_{50}$ | MMP13 IC$_{50}$ | TACE IC$_{50}$ |
|---|---|---|---|---|---|---|---|---|---|
| 16 | 3-[4-(aminomethyl)cyclohexyl]-N$^1$-hydroxy-N$^2$-{[4-(phenyloxy)phenyl]sulfonyl}alaninamide | A | B | A | A | | | A | B |
| 17 | N$^2$-{[6-(3-fluorophenyl)pyridin-3-yl]sulfonyl}-N$^1$-hydroxy-6-morpholin-4-yl-D-norleucinamide | A | D | A | B | | | A | C |
| 18 | N$^6$-[(E)-(cyanoimino)(propylamino)methyl]-N$^2$-{[6-(3-fluorophenyl)pyridin-3-yl]sulfonyl}-N$^1$-hydroxy-D-lysinamide | A | C | A | B | | | A | C |
| 19 | N$^1$-hydroxy-5-morpholin-4-yl-N$^2$-{[4-(phenyloxy)phenyl]sulfonyl}-D-norvalinamide | A | B | A | A | | | A | A |
| 20 | N$^6$-[(E)-amino(cyanoimino)methyl]-N$^2$-{[6-(3-fluorophenyl)pyridin-3-yl]sulfonyl}-N$^1$-hydroxy-D-lysinamide | A | C | A | B | | | A | B |
| 21 | N$^1$-hydroxy-N$^2$-{[6-(naphthalen-1-yloxy)pyridin-3-yl]sulfonyl}-D-argininamide | B | C | B | C | | | A | |
| 22 | N$^2$-{[3-fluoro-4-(phenyloxy)phenyl]sulfonyl}-N$^1$-hydroxy-D-argininamide | A | B | A | A | | | A | B |
| 23 | N$^6$-[(E)-(cyanoimino)(propylamino)methyl]-N$^1$-hydroxy-N$^2$-{[4-(phenyloxy)phenyl]sulfonyl}-D-lysinamide | A | B | A | A | | | A | A |
| 24 | N$^6$-((Z)-(cyanoimino){[2-(methyloxy)ethyl]amino}methyl)-N$^1$-hydroxy-N$^2$-{[4-(phenyloxy)phenyl]sulfonyl}-D-lysinamide | A | B | A | A | | | A | B |
| 25 | N$^6$-[-(E)-amino(cyanoimino)methyl]-N$^1$-hydroxy-N$^2$-{[4-(phenyloxy)phenyl]sulfonyl}-D-lysinamide | A | B | A | A | | | A | A |
| 26 | N$^2$-({4-[(4-fluorophenyl)oxy]phenyl}sulfonyl)-N$^1$-hydroxy-D-argininamide | A | B | A | A | | | A | A |
| 27 | N$^5$-[(Z)-amino(nitroimino)methyl]-N$^1$-hydroxy-N$^2$-{[4-(phenyloxy)phenyl]sulfonyl}-D-ornithinamide | A | B | A | A | | | A | A |
| 28 | N$^1$-hydroxy-N~2~-{[6-(5,6,7,8-tetrahydronaphthalen-2-yloxy)pyridin-3-yl]sulfonyl}-D-lysinamide | | D | | B | | | A | |
| 29 | N$^6$-{(Z)-(cyanoimino)[(2-morpholin-4-ylethyl)amino]methyl}-N$^1$-hydroxy-N$^2$-{[4-(phenyloxy)phenyl]sulfonyl}-D-lysinamide | A | B | A | | | | A | A |
| 30 | N$^6$-[(Z)-(cyanoimino)(cyclopropylamino)methyl]-N$^1$-hydroxy-N$^2$-{[4-(phenyloxy)phenyl]sulfonyl}-D-lysinamide | A | A | A | | | | A | A |
| 31 | N$^2$-{[3,5-difluoro-4-(phenyloxy)phenyl]sulfonyl}-N$^1$-hydroxy-D-argininamide | A | | | | | | | B |
| 32 | N$^2$-({4-[(4-chlorophenyl)oxy]-3-fluorophenyl}sulfonyl)-N$^1$-hydroxy-D-argininamide | A | B | A | A | | | A | A |

TABLE 4-continued

| # | Compound Name | ADAM-10 IC$_{50}$ | MMP1 IC$_{50}$ | MMP2 IC$_{50}$ | MMP3 IC$_{50}$ | MMP8 IC$_{50}$ | MMP9 IC$_{50}$ | MMP13 IC$_{50}$ | TACE IC$_{50}$ |
|---|---|---|---|---|---|---|---|---|---|
| 33 | N$^2$-({3,5-difluoro-4-[(4-fluorophenyl)oxy]phenyl}sulfonyl)-N$^1$-hydroxy-D-argininamide | A | D | C | C | B | B | A | B |
| 34 | 3-[1-((Z)-(cyanoimino){[2-(methyloxy)ethyl]amino}methyl)piperidin-4-yl]-N$^1$-hydroxy-N$^2$-{[4-(phenyloxy)phenyl]sulfonyl}alaninamide | | B | | A | | | A | |
| 35 | 3-{1-[(Z)-(cyanoimino)(propylamino)methyl]piperidin-4-yl}-N$^1$-hydroxy-N$^2$-{[4-(phenyloxy)phenyl]sulfonyl}alaninamide | A | B | | | | | A | |
| 36 | N$^5$-[(Z)-amino(nitroimino)methyl]-N$^2$-{[6-(3-fluorophenyl)pyridin-3-yl]sulfonyl}-N$^1$-hydroxy-D-ornithinamide | A | B | A | B | | | A | B |
| 37 | N$^2$-({4-[(4-chlorophenyl)oxy]-3,5-difluorophenyl}sulfonyl)-N$^1$-hydroxy-D-argininamide | A | C | A | B | B | B | A | B |
| 38 | N$^1$-hydroxy-N$^2$-{[6-(5,6,7,8-tetrahydronaphthalen-2-yloxy)pyridin-3-yl]sulfonyl}-D-argininamide | A | C | A | A | | | A | B |
| 39 | N$^2$-({4-[(3,5-dimethylphenyl)oxy]-3-fluorophenyl}sulfonyl)-N$^1$-hydroxy-D-argininamide | A | C | A | B | | | A | A |
| 40 | N$^2$-({3-fluoro-4-[(4-fluorophenyl)oxy]phenyl}sulfonyl)-N$^1$-hydroxy-D-argininamide | A | B | A | A | | | A | B |
| 41 | N$^2$-({4-[(4-cyanophenyl)oxy]-3-fluorophenyl}sulfonyl)-N$^1$-hydroxy-D-argininamide | A | C | | A | | | A | A |
| 42 | N$^6$-[(E)-(cyanoimino)(morpholin-4-yl)methyl]-N$^2$-({4-[(4-fluorophenyl)oxy]phenyl}sulfonyl)-N$^1$-hydroxy-D-lysinamide | A | A | | A | | | A | |
| 43 | 3-[1-((Z)-[(aminocarbonyl)imino]{[2-(methyloxy)ethyl]amino}methyl)piperidin-4-yl]-N$^1$-hydroxy-N$^2$-{[4-(phenyloxy)phenyl]sulfonyl}alaninamide | A | B | A | A | | | A | |
| 44 | N$^6$-(4,5-dihydro-1H-imidazol-2-yl)-N$^2$-({4-[(4-fluorophenyl)oxy]phenyl}sulfonyl)-N$^1$-hydroxy-D-lysinamide | A | A | A | A | | | A | |
| 45 | N$^6$-[(E)-(cyanoimino)(propylamino)methyl]-N$^2$-({4-[(4-fluorophenyl)oxy]phenyl}sulfonyl)-N$^1$-hydroxy-D-lysinamide | A | B | A | A | | | A | |
| 46 | N$^6$-[(E)-[(aminocarbonyl)imino](hydroxyamino)methyl]-N$^2$-({4-[(4-fluorophenyl)oxy]phenyl}sulfonyl)-N$^1$-hydroxy-D-lysinamide | A | | A | A | | | A | |

TABLE 4-continued

| # | Compound Name | ADAM-10 IC$_{50}$ | MMP1 IC$_{50}$ | MMP2 IC$_{50}$ | MMP3 IC$_{50}$ | MMP8 IC$_{50}$ | MMP9 IC$_{50}$ | MMP13 IC$_{50}$ | TACE IC$_{50}$ |
|---|---|---|---|---|---|---|---|---|---|
| 47 | N$^6$-[(E)-(cyanoimino)(hydroxyamino)methyl]-N$^2$-({4-[(4-fluorophenyl)oxy]phenyl}sulfonyl)-N$^1$-hydroxy-D-lysinamide | A | B | A | A | | | A | |
| 48 | N$^6$-((E)-(cyanoimino){[2-(methyloxy)ethyl]amino}methyl)-N$^2$-{[6-(3-fluorophenyl)pyridin-3-yl]sulfonyl}-N$^1$-hydroxy-D-lysinamide | A | B | A | A | | | A | |
| 49 | N$^6$-[(Z)-(cyanoimino)(cyclopropylamino)methyl]-N$^2$-{[6-(3-fluorophenyl)pyridin-3-yl]sulfonyl}-N$^1$-hydroxy-D-lysinamide | A | D | A | B | | | A | |
| 50 | N$^2$-({4-[(4-fluorophenyl)oxy]phenyl}sulfonyl)-N$^1$-hydroxy-D-lysinamide | A | B | A | A | | | A | |
| 51 | N$^6$-((Z)-(cyanoimino){[2-(methyloxy)ethyl]amino}methyl)-N$^2$-({4-[(4-fluorophenyl)oxy]phenyl}sulfonyl)-N$^1$-hydroxy-D-lysinamide | A | B | A | A | | | A | |
| 52 | N$^6$-{(Z)-(cyanoimino)[(2-morpholin-4-ylethyl)amino]methyl}-N$^2$-{[6-(3-fluorophenyl)pyridin-3-yl]sulfonyl}-N$^1$-hydroxy-D-lysinamide | A | B | A | A | | | A | |
| 53 | 3-{1-[amino(imino)methyl]piperidin-4-yl}-N$^1$-hydroxy-N$^2$-{[4-(phenyloxy)phenyl]sulfonyl}alaninamide | A | B | A | A | | | A | B |
| 54 | N$^2$-({-4-[(4-fluorophenyl)oxy]phenyl}sulfonyl)-N$^1$-hydroxy-5-morpholin-4-ylnorvalinamide | A | B | A | A | | | A | |
| 55 | N$^2$-({4-[(4-fluorophenyl)oxy]phenyl}sulfonyl)-N$^1$-hydroxy-6-morpholin-4-yl-D-norleucinamide | A | B | A | A | | | A | A |
| 56 | N$^2$-({3,5-difluoro-4-[(4-fluorophenyl)oxy]phenyl}sulfonyl)-N$^1$-hydroxy-3-[(2-morpholin-4-ylethyl)thio]-D-valinamide | B | C | B | B | | | B | |
| 57 | N$^2$-({6-[(4-fluorophenyl)oxy]pyridin-3-yl}sulfonyl)-N$^1$-hydroxy-D-argininamide | A | B | A | A | | | A | |
| 58 | N$^2$-({3,5-difluoro-4-[(4-fluorophenyl)oxy]phenyl}sulfonyl)-N$^1$-hydroxy-6-morpholin-4-yl-D-norleucinamide | A | D | A | B | | | A | |
| 59 | N$^6$-[(Z)-(cyanoimino)(morpholin-4-yl)methyl]-N$^2$-({3-fluoro-4-[(4-fluorophenyl)oxy]phenyl}sulfonyl)-N$^1$-hydroxy-D-lysinamide | A | B | A | A | | | A | |
| 60 | 3-[1-((E)-(cyanoimino){[2-(methyloxy)ethyl]amino}methyl)piperidin-4-yl]-N$^2$-({3,5-difluoro-4-[(4-fluorophenyl)oxy]phenyl}sulfonyl)-N$^1$-hydroxyalaninamide | B | C | A | B | | | A | |

TABLE 4-continued

| # | Compound Name | ADAM-10 IC$_{50}$ | MMP1 IC$_{50}$ | MMP2 IC$_{50}$ | MMP3 IC$_{50}$ | MMP8 IC$_{50}$ | MMP9 IC$_{50}$ | MMP13 IC$_{50}$ | TACE IC$_{50}$ |
|---|---|---|---|---|---|---|---|---|---|
| 61 | N$^2$-({6-[(4-chlorophenyl)oxy]pyridin-3-yl}sulfonyl)-N$^1$-hydroxy-D-argininamide | A | B | A | A | | | A | |
| 62 | N$^2$-({3,5-difluoro-4-[(4-fluorophenyl)oxy]phenyl}sulfonyl)-N$^1$-hydroxy-N$^6$-(morpholin-4-ylcarbonyl)-D-lysinamide | A | C | A | B | | | A | |
| 63 | 4-cyano-N-hydroxy-N-{[4-(phenyloxy)phenyl]sulfonyl}-D-phenylalaninamide | A | B | A | A | | | A | |
| 64 | 4-cyano-N-({3,5-difluoro-4-[(4-fluorophenyl)oxy]phenyl}sulfonyl)-N-hydroxy-D-phenylalaninamide | B | | B | | | | | |
| 65 | N$^2$-({4-[(4-chlorophenyl)oxy]-3,5-difluorophenyl}sulfonyl)-N$^1$-hydroxy-6-morpholin-4-yl-D-norleucinamide | A | C | A | B | | | A | |
| 66 | 3-cyano-N-({3,5-difluoro-4-[(4-fluorophenyl)oxy]phenyl}sulfonyl)-N-hydroxy-D-phenylalaninamide | B | C | B | C | | | B | |
| 67 | 3-cyano-N-hydroxy-N-{[4-(phenyloxy)phenyl]sulfonyl}-D-phenylalaninamide | A | B | A | A | | | A | |
| 68 | N$^2$-{[3-fluoro-4-(phenyloxy)phenyl]sulfonyl}-N$^1$-hydroxy-6-morpholin-4-yl-D-norleucinamide | A | C | A | B | | | A | |
| 69 | N$^2$-({3,5-difluoro-4-[(4-hydroxy-phenyl)oxy]phenyl}sulfonyl)-N$^1$-hydroxyargininamide | A | D | A | B | | | A | |
| 70 | N$^2$-{[3,5-difluoro-4-(pyridin-3-yloxy)phenyl]sulfonyl}-N$^1$-hydroxyargininamide | B | D | B | D | | | C | |
| 71 | N$^2$-({3,5-difluoro-4-[(4-fluorophenyl)oxy]phenyl}sulfonyl)-N$^1$-hydroxy-N$^6$-({[2-(methyloxy)ethyl]amino}carbonyl)-D-lysinamide | A | C | A | | | | A | |
| 72 | N$^2$-({3,5-difluoro-4-[(4-fluorophenyl)oxy]phenyl}sulfonyl)-N$^6$-[1-(4,4-dimethyl-2,6-dioxocyclohexylidene)ethyl]-N$^1$-hydroxy-D-lysinamide | B | C | A | B | | | A | |
| 73 | N$^2$-{[3,5-difluoro-4-({4-[(phenyl-methyl)oxy]phenyl}oxy)phenyl]sulfonyl}-N$^1$-hydroxyargininamide | A | D | A | B | | | A | |
| 74 | N$^2$-({3-fluoro-4-[(4-fluorophenyl)oxy]phenyl}sulfonyl)-N$^1$-hydroxy-3-[(2-morpholin-4-ylethyl)thio]-D-valinamide | B | B | A | B | | | A | |
| 75 | N$^2$-({4-[(4-bromophenyl)oxy]-3,5-difluorophenyl}sulfonyl)-N$^1$-hydroxy-D-argininamide | A | C | A | B | | | A | |
| 76 | N$^2$-({3-fluoro-4-[(4-fluorophenyl)oxy]phenyl}sulfonyl)-N$^1$-hydroxy-3-[(2-morpholin-4-yl-2-oxoethyl)thio]-D-valinamide | A | B | A | A | | | A | |
| 77 | N$^2$-({3-fluoro-4-[(4-fluorophenyl)oxy]phenyl}sulfonyl)-N$^1$-hydroxy-3-morpholin-4-yl-D-alaninamide | B | C | A | B | | | A | |

TABLE 4-continued

| # | Compound Name | ADAM-10 IC$_{50}$ | MMP1 IC$_{50}$ | MMP2 IC$_{50}$ | MMP3 IC$_{50}$ | MMP8 IC$_{50}$ | MMP9 IC$_{50}$ | MMP13 IC$_{50}$ | TACE IC$_{50}$ |
|---|---|---|---|---|---|---|---|---|---|
| 78 | N-({3,5-difluoro-4-[(4-fluorophenyl)oxy]phenyl}sulfonyl)-N-hydroxy-4-[(hydroxyamino)(imino)methyl]-D-phenylalaninamide | | D | B | C | | | B | |
| 79 | N-({3,5-difluoro-4-[(4-fluorophenyl)oxy]phenyl}sulfonyl)-N-hydroxy-3-[(hydroxyamino)(imino)methyl]-D-phenylalaninamide | A | C | A | C | | | B | |
| 80 | N$^2$-({4-[(4-chlorophenyl)oxy]-3,5-difluorophenyl}sulfonyl)-N$^1$-hydroxy-3-[1-(morpholin-4-ylcarbonyl)piperidin-4-yl]alaninamide | A | D | A | C | | | B | |
| 81 | 3-[amino(imino)methyl]-N-({3,5-difluoro-4-[(4-fluorophenyl)oxy]phenyl}sulfonyl)-N-hydroxy-D-phenylalaninamide | A | D | A | C | | | B | |
| 82 | 4-[amino(imino)methyl]-N-({3,5-difluoro-4-[(4-fluorophenyl)oxy]phenyl}sulfonyl)-N-hydroxy-D-phenylalaninamide | A | D | B | C | | | B | |
| 83 | N$^5$-(aminocarbonyl)-N$^2$-({3-fluoro-4-[(4-fluorophenyl)oxy]phenyl}sulfonyl)-N$^1$-hydroxy-D-ornithinamide | A | B | A | A | | | A | |
| 84 | (2R)-2-[({4-[(4-chlorophenyl)oxy]-3,5-difluorophenyl}sulfonyl)amino]-4-(dimethylamino)-N-hydroxybutanamide | B | | A | C | | | B | |
| 85 | (2R)-2-[({4-[(4-chlorophenyl)oxy]-3,5-difluorophenyl}sulfonyl)amino]-4-{[1-(4,4-dimethyl-2,6-dioxocyclohexylidene)-2-methylbutyl]amino}-N-hydroxybutanamide | B | D | B | C | | | B | |
| 86 | N$^2$-({4-[(4-chlorophenyl)oxy]-3,5-difluorophenyl}sulfonyl)-N$^1$-hydroxy-3-[(2-morpholin-4-yl-2-oxoethyl)thio]-D-valinamide | B | C | B | C | | | B | |
| 87 | (2R)-4-amino-2-[({4-[(4-chlorophenyl)oxy]-3,5-difluorophenyl}sulfonyl)amino]-N-hydroxybutanamide | A | C | A | C | | | A | |
| 88 | (2R)-4-{[amino(imino)methyl]amino}-2-[({4-[(4-chlorophenyl)oxy]-3,5-difluorophenyl}sulfonyl)amino]-N-hydroxybutanamide | A | C | A | C | | | A | |
| 89 | 2-[({4-[(4-chlorophenyl)oxy]-3,5-difluorophenyl}sulfonyl)amino]-N-hydroxy-2-piperidin-4-ylacetamide | A | | A | C | | | B | |
| 90 | 2-[({4-[(4-chlorophenyl)oxy]-3-fluorophenyl}sulfonyl)amino]-N-hydroxy-2-piperidin-4-ylacetamide | A | | A | B | | | A | |
| 91 | 2-[({3-fluoro-4-[(4-fluorophenyl)oxy]phenyl}sulfonyl)amino]-N-hydroxy-2-piperidin-4-ylacetamide | B | | A | B | | | A | |
| 92 | 2-[({4-[(4-fluorophenyl)oxy]phenyl}sulfonyl)amino]-N-hydroxy-2-piperidin-4-ylacetamide | A | | A | B | | | A | |

TABLE 4-continued

| # | Compound Name | ADAM-10 IC$_{50}$ | MMP1 IC$_{50}$ | MMP2 IC$_{50}$ | MMP3 IC$_{50}$ | MMP8 IC$_{50}$ | MMP9 IC$_{50}$ | MMP13 IC$_{50}$ | TACE IC$_{50}$ |
|---|---|---|---|---|---|---|---|---|---|
| 93 | 2-({[6-(3-fluorophenyl)pyridin-3-yl]sulfonyl}amino)-N-hydroxy-2-piperidin-4-ylacetamide | B | | | | | | | |
| 94 | 2-[({4-[(3,5-dimethylphenyl)oxy]-3,5-difluorophenyl}sulfonyl)amino]-N-hydroxy-2-piperidin-4-ylacetaxmide | B | | C | C | | | C | |
| 95 | 3-[4-(aminomethyl)cyclohexyl]-N$^2$-({4-[(4-chlorophenyl)oxy]-3,5-difluorophenyl}sulfony)-N$^1$-hydroxyalaninamide | B | | B | C | | | A | |
| 96 | 3-[4-(aminomethyl)cyclohexyl]-N$^2$-({3,5-difluoro-4-[(4-fluorophenyl)oxy]phenyl}sulfonyl)-N$^1$-hydroxyalaninamide | A | | B | C | | | B | |
| 97 | 3-[4-(aminomethyl)cyclohexyl]-N$^2$-({4-[(4-chlorophenyl)oxy]-3-fluorophenyl}sulfonyl)-N$^1$-hydroxyalaninamide | A | | A | A | | | A | |
| 98 | 3-[4-(aminomethyl)cyclohexyl]-N$^2$-({3-fluoro-4-[(4-fluorophenyl)oxy]phenyl}sulfonyl)-N$^1$-hydroxyalaninamide | A | C | A | A | | | A | |
| 99 | 3-[4-(aminomethyl)cyclohexyl]-N$^2$-({4-[(4-fluorophenyl)oxy]phenyl}sulfonyl)-N$^1$-hydroxyalaninamide | A | | A | A | | | A | |
| 100 | 3-[4-(aminomethyl)cyclohexyl]-N$^2$-{[(6-(3-fluorophenyl)pyridin-3-yl]sulfonyl}-N$^1$-hydroxyalaninamide | A | | A | B | | | A | |
| 101 | 3-[4-(aminomethyl)cyclohexyl]-N$^2$-({4-[(3,5-dimethylphenyl)oxy]-3,5-difluorophenyl}sulfonyl)-N$^1$-hydroxyalaninamide | C | | | | | | | |

We claim:

1. A compound of structural formula I:

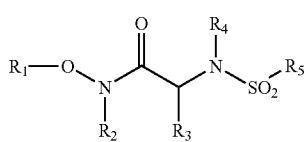

or a pharmaceutically acceptable salt thereof, wherein $R_1$ is selected from hydrogen, alkyl, alkanoyl, arylalkyl, and arylalkanoyl, wherein
the arylalkyl and arylalkanoyl groups are unsubstituted or substituted with 1, 2, 3, 4, or 5 $R_6$ groups;

$R_6$ at each occurrence is independently selected from halogen, hydroxy, —NO$_2$, —CO$_2$R$_{10}$, —CN, alkyl, alkoxy, haloalkyl, and haloalkoxy;

$R_2$ is selected from hydrogen, alkyl, alkoxy, alkanoyl, arylalkyl and arylalkanoyl, wherein
the arylalkyl and arylalkanoyl groups are unsubstituted or substituted with 1, 2, 3, 4, or 5 $R_6$ groups;

$R_3$ is —Z—Q—J, wherein
Z is selected from alkyl, alkoxyalkyl, alkylthioalkyl, and alkenyl, each of which is unsubstituted or substituted with 1 or 2 groups that are independently selected from alkoxy, hydroxy, and halogen;

Q is selected from a direct bond between Z and J, —C(=O)—, aryl, heteroaryl, and heterocycloalkyl, wherein
the aryl, heteroaryl, or heterocycloalkyl group is unsubstituted or substituted with 1 or 2 groups that are independently selected from alkyl, halogen, —NR$_8$R$_9$, and alkoxy;

J is —C(=NR$_7$)NR$_8$R$_9$ or —NH—C(=NR$_7$)NR$_8$R$_9$ wherein $R_7$ is selected from H, CN, NO$_2$, alkyl, alkanoyl, arylalkanoyl and —C(=O)NR$_{10}$R$_{11}$, wherein
$R_{10}$ and $R_{11}$ are independently selected from H, and alkyl, and $R_8$ and $R_9$ are independently selected from H, alkyl, hydroxy, alkoxy, alkoxyalkyl, heterocycloalkylalkyl, arylalkyl, and heteroarylalkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently selected from alkyl, alkoxy, hydroxy, and halogen;

or $R_7$, $R_8$, and the nitrogens to which they are attached form a 5, 6 or 7 membered heterocycloalkyl group that is unsubstituted or substituted with 1, 2 or 3 groups that are independently selected from alkyl, alkoxy, hydroxy, and halogen; and $R_9$ is selected from H, alkyl, hydroxy, alkoxy, alkoxyalkyl, heterocycloalkylalkyl, arylalkyl, and heteroarylalkyl, wherein each of the above is unsubstituted or substituted with 1, 2, 3, or 4 $R_6$ groups;

$R_4$ is selected from H, alkyl, and arylalkyl, wherein the arylalkyl group is unsubstituted or substituted with 1, 2, 3, 4, or 5 $R_6$ groups; and $R_5$ is —M—G—A, wherein M is aryl, wherein M is unsubstituted or substituted with 1, 2, 3, or 4 groups that are independently selected from halogen, alkyl, hydroxy, alkoxy, haloalkyl, —CN, haloalkoxy, and hydroxyalkyl;

G is selected from a direct bond between M and A, $CH_2$, -alkyl-O—, —O-alkyl-, O, S, SO, and $SO_2$;

A is aryl, wherein A is unsubstituted or substituted with 1, 2, 3, 4, or 5 groups that are independently selected from halogen, alkyl, alkoxy, haloalkyl, aryloxy, heteroaryloxy, arylalkoxy, heteroarylalkoxy, haloalkoxy, —CN, and $NO_2$;

with the proviso that when M is phenyl, G is a direct bond between M and A, and A is phenyl, then at least one of the four remaining hydrogens on the phenyl ring of M, of M—G—A, must be substituted with a group independently selected from halogen, alkyl, hydroxy, alkoxy, haloalkyl, —CN, haloalkoxy, and hydroxyalkyl.

2. The compound according to claim 1, wherein $R_1$ is selected from the group consisting of hydrogen, $C_1$-$C_6$ alkyl, phenyl $C_1$-$C_6$ alkyl, and phenyl $C_1$-$C_6$ alkanoyl, wherein the phenylalkyl and phenylalkanoyl groups are unsubstituted or substituted with 1, 2, 3, 4, or 5 $R_6$ groups, and $R_2$ is selected from the group consisting of hydrogen, $C_1$-$C_6$ alkyl, $C_1$-$C_6$ alkanoyl, phenyl $C_1$-$C_6$ alkyl and phenyl $C_1$-$C_6$ alkanoyl, wherein the phenylalkyl and phenylalkanoyl groups are unsubstituted or substituted with 1, 2, 3, 4, or 5 $R_6$ groups, wherein $R_6$ at each occurrence is independently selected from the group consisting of halogen, hydroxy, —$NO_2$, —CN, $C_1$-$C_6$ alkyl, $C_1$-$C_6$ alkoxy, $CF_3$, and $OCF_3$.

3. The compound according to claim 1, wherein $R_3$ is —Z—Q—J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 groups independently selected from $C_1$-$C_4$ alkyl, halogen, and $C_1$-$C_4$ alkoxy;

Q is a direct bond between Z and J, —C(=O)—, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently selected from $C_1$-$C_4$ alkyl, halogen, and $C_1$-$C_4$ alkoxy;

J is —C(=$NR_7$)$NR_8R_9$ or —NH—C(=$NR_7$)$NR_8R_9$, wherein $R_7$ is selected from the group consisting of H, —CN, —$NO_2$, $C_1$-$C_6$ alkyl, $C_1$-$C_6$ alkanoyl, phenyl $C_1$-$C_6$ alkanoyl and —C(=O)$NR_{10}R_{11}$, wherein $R_{10}$ and $R_{11}$ are independently selected from H and $C_1$-$C_6$ alkyl, $R_8$ and $R_9$ are each independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently selected from $C_1$-$C_6$ alkyl, $C_1$-$C_6$ alkoxy, hydroxy, and halogen; or $R_7$, $R_8$, and the nitrogens to which they are attached form a 5, 6 or 7 membered heterocycloalkyl group that is unsubstituted or substituted with 1, 2 or 3 groups that are independently selected from $C_1$-$C_6$ alkyl, $C_1$-$C_6$ alkoxy, hydroxy, and halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, thiomorpholinyl S-oxide, phenyl, naphthyl, thiomorpholinyl S,S-dioxide, pyrrolidinyl, pyridyl, pyridazyl, pyrimidyl, pyrazinyl, and imidazolyl, wherein each of the above is unsubstituted or substituted with 1, 2, 3, or 4 $R_6$ groups, wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

4. The compound according to claim 1, wherein $R_5$ is —M—G—A, wherein

M is phenyl, wherein M is unsubstituted or substituted with 1, 2, 3, or 4 groups that are independently selected from the group consisting of halogen, $C_1$-$C_6$ alkyl, hydroxy, $C_1$-$C_6$ alkoxy, halo $C_1$-$C_6$ alkyl, halo $C_1$-$C_6$ alkoxy, and hydroxy $C_1$-$C_6$ alkyl, G is selected from a direct bond between M and A, $CH_2$, O, S, SO, and $SO_2$;

A is selected from the group consisting of phenyl, naphthyl, tetrahydronaphthyl, and dihydronaphthyl, wherein each of the above is unsubstituted or substituted with 1, 2, 3, 4, or 5 groups that are independently selected from halogen, $C_1$-$C_6$ alkyl, $C_1$-$C_6$ alkoxy, halo $C_1$-$C_6$ alkyl, halo $C_1$-$C_6$ alkoxy, CN, and $NO_2$.

5. The compound according to claim 1, wherein $R_1$ is hydrogen, $C_1$-$C_6$ alkyl or benzyl;

$R_2$ is hydrogen, $C_1$-$C_6$ alkyl or benzyl; and $R_3$ is —Z—Q—J, wherein

Z is $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy;

Q is a direct bond between Z and J, —C(=O)—, piperidinyl, pyrrolyl, piperazinyl, imidazolidinyl, morpholinyl, thiomorpholinyl, azepanyl, or azocanyl wherein each of the above is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ or —NH—C(=NR$_7$)NR$_8$R$_9$, wherein

R$_7$ is selected from the group consisting of H, —CN, —NO$_2$, $C_1$-$C_6$ alkyl, $C_1$-$C_6$ alkanoyl, phenyl $C_1$-$C_6$ alkanoyl and —C(=O)NR$_{10}$R$_{11}$, wherein R$_{10}$ and R$_{11}$ are independently H, or $C_1$-$C_6$ alkyl, and R$_8$ and R$_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 R$_6$ groups; or R$_8$ and R$_9$ and the nitrogen to which they are attached form a 5, 6 or 7 membered heterocycloalkyl ring, which is unsubstituted or substituted with 1, 2, or 3 groups that are independently selected from $C_1$-$C_6$ alkyl, $C_1$-$C_6$ alkoxy, hydroxy, and halogen; or R$_7$, R$_8$, and the nitrogens to which they are attached form a 5, 6, or 7 membered heterocycloalkyl group that is unsubstituted or substituted with 1, 2 or 3 groups that are independently selected from $C_1$-$C_6$ alkyl, $C_1$-$C_6$ alkoxy, hydroxy, and halogen, wherein each of the above is unsubstituted or substituted with 1, 2, 3, or 4 R$_6$ groups, wherein R$_6$ at each occurrence is independently selected from the group consisting of halogen, hydroxy, NO$_2$, $C_1$-$C_6$ alkyl, $C_1$-$C_6$ alkoxy, CF$_3$, and OCF$_3$; and R$_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, thiomorpholinyl S-oxide, phenyl, naphthyl, thiomorpholinyl S,S-dioxide, pyrrolidinyl, pyridyl, pyridazyl, pyrimidyl, pyrazinyl, and imidazolyl, wherein each of the above is unsubstituted or substituted with 1, 2, 3, or 4 R$_6$ groups;

R$_4$ is selected from the group consisting of H, $C_1$-$C_4$ alkyl, benzyl and phenethyl, wherein the benzyl and phenethyl groups are unsubstituted or substituted with 1, 2, 3, or 4 R$_6$ groups;

R$_5$ is —M—G—A, wherein

M is phenyl, wherein M is unsubstituted or substituted with 1, 2, 3, or 4 groups that are independently selected from the group consisting of halogen, $C_1$-$C_6$ alkyl, hydroxy, $C_1$-$C_6$ alkoxy, halo $C_1$-$C_6$ alkyl, halo $C_1$-$C_6$ alkoxy, and hydroxy $C_1$-$C_6$ alkyl, G is selected from a direct bond between M and A, CH$_2$, O, S, SO, and SO$_2$;

A is selected from the group consisting of phenyl, naphthyl, tetrahydronaphthyl, and dihydronaphthyl, wherein each of the above is unsubstituted or substituted with 1, 2, 3, 4, or 5 groups that are independently halogen, $C_1$-$C_6$ alkyl, $C_1$-$C_6$ alkoxy, halo $C_1$-$C_6$ alkyl, halo $C_1$-$C_6$ alkoxy, CN, or NO$_2$.

6. The compound according to claim 5, wherein

R$_5$ is —M—G—A, wherein

M is phenyl, which is unsubstituted or substituted with 1, 2, or 3 groups that are independently selected from the group consisting of F, Cl, Br, $C_1$-$C_4$ alkyl, hydroxy, methoxy, ethoxy, isopropoxy, CF$_3$, OCF$_3$, halo $C_1$-$C_4$ alkyl, halo $C_1$-$C_4$ alkoxy, and hydroxy $C_1$-$C_4$ alkyl;

G is selected from a direct bond between M and A, CH$_2$, O, S, SO, and SO$_2$;

A is selected from the group consisting of phenyl, naphthyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, CF$_3$, OCF$_3$, —CN, and —NO$_2$.

7. The compound according to claim 6, wherein

R$_3$ is —Z—Q—J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=NR$_7$)NR$_8$R$_9$ or —NH—C(=NR$_7$)NR$_8$R$_9$, wherein

R$_7$ is selected from the group consisting of H, CN, NO$_2$, $C_1$-$C_6$ alkyl, $C_1$-$C_6$ alkanoyl, and —C(=O)NR$_{10}$R$_{11}$, wherein R$_{10}$ and R$_{11}$ are independently H, or $C_1$-$C_6$ alkyl, and R$_8$ and R$_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 R$_6$ groups; wherein R$_6$ at each occurrence is independently selected from the group consisting of halogen, hydroxy, NO$_2$, $C_1$-$C_6$ alkyl, $C_1$-$C_6$ alkoxy, CF$_3$, and OCF$_3$; or R$_8$ and R$_9$ and the nitrogen to which they are attached form a 5 or 6 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

8. The compound according to claim 7, wherein

R$_3$ is —Z—Q—J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy; and J is —C(=NR$_7$)NR$_8$R$_9$, wherein R$_7$ is selected from the group consisting of H, CN, NO$_2$, $C_1$-$C_6$ alkyl, $C_1$-$C_6$ alkanoyl, and —C(=O)NR$_{10}$R$_{11}$, wherein R$_{10}$ and R$_{11}$ are independently H, or $C_1$-$C_6$ alkyl, and R$_8$ and R$_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups, wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$; or $R_8$ and $R_9$ and the nitrogen to which they are attached form a 5 or 6 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

9. The compound according to claim 7, wherein $R_8$ and $R_9$ and the nitrogen to which they are attached form a morpholinyl, thiomorpholinyl, piperazinyl, piperidinyl or pyrrolidinyl ring, each of which is unsubstituted or substituted with 1, 2, or 3 groups that are independently $C_1$-$C_6$ alkyl, $C_1$-$C_6$ alkoxy, hydroxy, or halogen.

10. The compound according to claim 6, wherein $R_3$ is —Z—Q—J wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein $R_7$, $R_8$, and the nitrogens to which they are attached form a 5, 6, or 7 membered heterocycloalkyl group that is unsubstituted or substituted with 1, or 2 groups that are independently $C_1$-$C_6$ alkyl, $C_1$-$C_6$ alkoxy, hydroxy, or halogen; and $R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, phenyl, naphthyl, pyrrolidinyl, pyridyl, pyridazyl, and imidazolyl, wherein each of the above is unsubstituted or substituted with 1, or 2 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

11. The compound according to claim 6, wherein $R_3$ is —Z—Q—J wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy; and J is —C(=$NR_7$)$NR_8R_9$ or —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, and —C(=O)$NR_{10}R_{11}$, wherein $R_{10}$ and $R_{11}$ are independently H, or $C_1$-$C_6$ alkyl, and $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

12. The compound as in claim 1 of structural formula II wherein $R_3$, $R_4$, and $R_5$ are as defined in claim 1.

13. The compound according to claim 12, wherein $R_4$ is selected from the group consisting of H, $C_1$-$C_4$ alkyl, and benzyl wherein the benzyl group is unsubstituted or substituted with 1, 2, 3, or 4 $R_6$ groups, wherein $R_6$ at each occurrence is independently selected from the group consisting of halogen, hydroxy, —$NO_2$, $C_1$-$C_6$ alkyl, $C_1$-$C_6$ alkoxy, $CF_3$, and $OCF_3$.

14. The compound according to claim 13, wherein $R_5$ is —M—G—A, wherein

M is phenyl, which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;

G is selected from a direct bond between M and A, $CH_2$, O, S, SO, and $SO_2$;

A is selected from the group consisting of phenyl, naphthyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$.

15. The compound according to claim 13, wherein $R_3$ is —Z—Q—J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, phenyl $C_1$-$C_6$ alkanoyl and —C(=O)$NR_{10}R_{11}$, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen, wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

16. The compound according to claim 12, of structural formula III

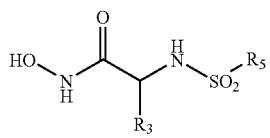

III wherein $R_3$ is —Z—Q—J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, phenyl $C_1$-$C_6$ alkanoyl and —C(=O)$NR_{10}R_{11}$, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, thiomorpholinyl, thiomorpholinyl S,S-dioxide, thiomorpholinyl S-oxide, piperidinyl $C_1$-$C_6$ alkyl, pyrrolidinyl $C_1$-$C_6$ alkyl, imidazolidinyl $C_1$-$C_6$ alkyl, $C_3$-$C_8$ cycloalkyl, $C_3$-$C_8$ cycloalkyl $C_1$-$C_6$ alkyl, phenyl $C_1$-$C_6$ alkyl, and pyridyl $C_1$-$C_6$ alkyl, pyridazyl $C_1$-$C_6$ alkyl, pyrimidyl $C_1$-$C_6$ alkyl, pyrazinyl $C_1$-$C_6$ alkyl, thienyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen; wherein each of the above is unsubstituted or substituted with 1, 2, 3, or 4 $R_6$ groups; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$; and $R_5$ is —M—G—A, wherein M is phenyl, which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;

G is selected from a direct bond between M and A, $CH_2$, O, S, SO, and $SO_2$; and A is selected from the group consisting of phenyl, naphthyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$.

17. The compound according to claim 16, wherein $R_3$ is —Z—Q—J, wherein

Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;

Q is a direct bond between Z and J, —C(=O)—, piperidinyl, pyrrolyl, piperazinyl, imidazolidinyl, morpholinyl, or thiomorpholinyl, wherein each is unsubstituted or substituted with 1 or 2 groups that are independently $C_1$-$C_4$ alkyl, halogen, or $C_1$-$C_4$ alkoxy;

J is —C(=$NR_7$)$NR_8R_9$ or —NH—C(=$NR_7$)$NR_8R_9$, wherein $R_7$ is selected from the group consisting of H, CN, $NO_2$, $C_1$-$C_6$ alkyl, $C_1$-$C_6$ alkanoyl, and —C(=O)$NR_{10}R_{11}$, wherein $R_{10}$ and $R_{11}$ are independently H, or $C_1$-$C_6$ alkyl, $R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, piperidinyl $C_1$-$C_6$ alkyl, pyrrolidinyl $C_1$-$C_6$ alkyl, $C_3$-$C_8$ cycloalkyl, $C_3$-$C_8$ cycloalkyl $C_1$-$C_6$ alkyl, benzyl, phenethyl, and pyridyl $C_1$-$C_6$ alkyl, pyridazyl $C_1$-$C_6$ alkyl, and furyl $C_1$-$C_6$ alkyl, wherein each of the above is unsubstituted or substituted with 1, 2, 3, or 4 $R_6$ groups; or $R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen; or $R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen; wherein $R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$; and $R_5$ is —M—G—A, wherein
M is phenyl, which is unsubstituted or substituted with 1, 2, or 3 groups that are independently selected from the group consisting of F, Cl, Br, $C_1$-$C_4$ alkyl, hydroxy, methoxy, ethoxy, isopropoxy, $CF_3$, $OCF_3$, halo $C_1$-$C_4$ alkyl, halo $C_1$-$C_4$ alkoxy, and hydroxy $C_1$-$C_4$ alkyl;
G is selected from a direct bond between M and A, $CH_2$, and O; and
A is selected from the group consisting of phenyl, naphthyl, tetrahydronaphthyl, and dihydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$.

18. The compound according to claim 17, of structural formula IV

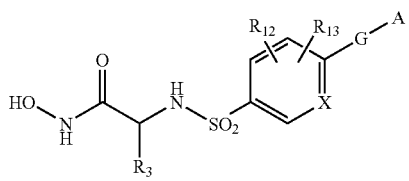

IV wherein
$R_3$ is defined in claim 17, and
X is CH or $CR_{11}$;
$R_{12}$ and $R_{13}$ are at each occurrence are independently selected from the group consisting of H, halogen, $CF_3$, $C_1$-$C_4$ alkyl, and $C_1$-$C_4$ alkoxy;
A is selected from the group consisting of phenyl, naphthyl, and tetrahydronaphthyl, wherein each is unsubstituted or substituted with 1, 2, or 3 groups that are independently selected from the group consisting of F, Cl, Br, $C_1$-$C_4$ alkyl, $C_1$-$C_4$ alkoxy, halo $C_1$-$C_4$ alkyl, $CF_3$, $OCF_3$, CN, and $NO_2$; and
G is selected from a direct bond between M and A, $CH_2$, and O.

19. The compound according to claim 18, of structural formula V

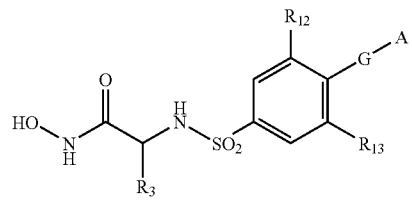

V wherein
$R_3$, is as defined in claim 18,
A is phenyl, 3-fluorophenyl, 4-fluorophenyl, 4-chlorophenyl, 4-cyanophenyl, benzo[1,3]dioxyl, 3,5-dimethylphenyl, 2-naphthyl, or 2-tetrahydronaphthyl;
G is a direct bond between M and A, or G is oxygen; and
$R_{12}$ and $R_{13}$ are independently H, fluoro, chloro, $CF_3$, methyl or methoxy.

20. The compound according to claim 19, wherein
$R_3$ is —Z—Q—J, wherein
Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;
Q is a direct bond between Z and J or —C(=O)—,
J is —NH—C(=NR_7)$NR_8R_9$, wherein
$R_7$ is selected from the group consisting of H, CN, $NO_2$, $C_1$-$C_6$ alkyl, $C_1$-$C_6$ alkanoyl, and —C(=O)$NR_{10}R_{11}$, wherein
$R_{10}$ and $R_{11}$ are independently H, or $C_1$-$C_6$ alkyl, and
$R_8$ and $R_9$ are independently selected from the group consisting of H, $C_1$-$C_6$ alkyl, hydroxy, $C_1$-$C_6$ alkoxy, alkoxy $C_1$-$C_6$ alkyl, morpholinyl $C_1$-$C_6$ alkyl, $C_3$-$C_8$ cycloalkyl, and $C_3$-$C_8$ cycloalkyl $C_1$-$C_6$ alkyl, wherein each of the above is unsubstituted or substituted with 1, 2, 3, or 4 $R_6$ groups, wherein
$R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$, or
$R_8$ and $R_9$ and the nitrogen to which they are attached form a 5, 6 or 7 membered heterocycloalkyl ring, which is unsubstituted or substituted with 1, 2, or 3 groups that are independently $C_1$-$C_6$ alkyl, $C_1$-$C_6$ alkoxy, hydroxy, or halogen.

21. The compound according to claim 19, wherein
$R_3$ is —Z—Q—J, wherein
Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;
Q is a direct bond between Z and J or —C(O)—,
J is —NH—C(=NR_7)$NR_8R_9$, wherein
$R_7$, $R_8$, and the nitrogens to which they are attached form a 5, 6, or 7 membered heterocycloalkyl group that is unsubstituted or substituted with 1, 2 or 3 groups that are independently $C_1$-$C_6$ alkyl, $C_1$-$C_6$ alkoxy, hydroxy, or halogen; and
$R_9$ is selected from the group consisting of H, $C_1$-$C_6$ alkyl, $C_1$-$C_6$ alkoxy, $C_1$-$C_6$ alkoxy $C_1$-$C_6$ alkyl, $C_3$-$C_8$ cycloalkyl, and $C_1$-$C_6$ alkyl substituted with at least one of morpholinyl, piperidinyl, thiomorpholinyl, phenyl, naphthyl, pyrrolidinyl, pyridyl, pyridazyl, pyrimidyl, pyrazinyl, and imidazolyl, wherein each of the above is unsubstituted or substituted with 1, 2, 3, or 4 $R_6$ groups, wherein
$R_6$ at each occurrence is independently selected from the group consisting of halogen, hydroxy, $NO_2$, $C_1$-$C_6$ alkyl, $C_1$-$C_6$ alkoxy, $CF_3$, and $OCF_3$.

22. The compound according to claim 19, wherein
$R_3$ is —Z—Q—J, wherein
Z is a $C_1$-$C_6$ alkyl, $C_1$-$C_6$ alkoxy $C_1$-$C_6$ alkyl, or $C_1$-$C_6$ alkylthio $C_1$-$C_6$ alkyl, each of which is unsubstituted or substituted with 1 or 2 $C_1$-$C_4$ alkyl, halogen, or $C_1$-$C_4$ alkoxy groups;
Q is a direct bond between Z and J, piperidinyl, pyrrolyl, piperazinyl, imidazolidinyl, morpholinyl, or thiomorpholinyl, wherein
each is unsubstituted or substituted with 1 or 2 groups that are independently $C_1$-$C_4$ alkyl, halogen, or $C_1$-$C_4$ alkoxy;
J is —C(=NR_7)$NR_8R_9$ wherein
$R_7$ is selected from the group consisting of H, CN, $NO_2$, $C_1$-$C_6$ alkyl, $C_1$-$C_6$ alkanoyl, and —C(=O)$NR_{10}R_{11}$, wherein

93

R$_{10}$ and R$_{11}$ are independently H, or C$_1$-C$_6$ alkyl,

R$_8$ and R$_9$ are independently selected from the group consisting of H, C$_1$-C$_6$ alkyl, hydroxy, C$_1$-C$_6$ alkoxy, alkoxy C$_1$-C$_6$ alkyl, morpholinyl C$_1$-C$_6$ alkyl, C$_3$-C$_8$ cycloalkyl, and C$_3$-C$_8$ cycloalkyl C$_1$-C$_6$ alkyl, wherein each of the above is unsubstituted or substituted with 1, 2, 3, or 4 R$_6$ groups; or R$_8$ and R$_9$ and the nitrogen to which they are attached form a 5, 6 or 7 membered heterocycloalkyl ring, which is unsubstituted or substituted with 1, 2, or 3 groups that are independently C$_1$-C$_6$ alkyl, C$_1$-C$_6$ alkoxy, hydroxy, or halogen; wherein R$_6$ at each occurrence is independently selected from the group consisting of halogen, hydroxy, NO$_2$, C$_1$-C$_6$ alkyl, C$_1$-C$_6$ alkoxy, CF$_3$, and OCF$_3$.

23. The compound of structural formula VII

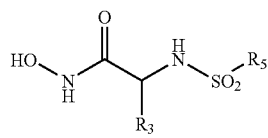

VII wherein

R$_3$ is —Z—Q—J, wherein

Z is a C$_1$-C$_{10}$ alkyl, C$_1$-C$_6$ alkoxy C$_1$-C$_6$ alkyl, or C$_1$-C$_6$ alkylthio C$_1$-C$_6$ alkyl, each of which is unsubstituted or substituted with 1 or 2 C$_1$-C$_4$ alkyl, halogen, or C$_1$-C$_4$ alkoxy groups;

Q is a direct bond between Z and J, —C(=O)—, piperidinyl, pyrrolyl, piperazinyl, imidazolidinyl, morpholinyl, thiomorpholinyl, azepanyl, or azocanyl wherein each is unsubstituted or substituted with 1 or 2 groups that are independently C$_1$-C$_4$ alkyl, halogen, or C$_1$-C$_4$ alkoxy;

J is —NH—C(=NR$_7$)NR$_8$R$_9$, wherein

R$_7$ is selected from the group consisting of H, CN, NO$_2$, C$_1$-C$_6$ alkyl, C$_1$-C$_6$ alkanoyl, phenyl C$_1$-C$_6$ alkanoyl and —C(=O)NR$_{10}$R$_{11}$, wherein R$_{10}$ and R$_{11}$ are independently H, or C$_1$-C$_6$ alkyl, R$_8$ and R$_9$ are independently selected from the group consisting of H, C$_1$-C$_6$ alkyl, hydroxy, C$_1$-C$_6$ alkoxy, alkoxy C$_1$-C$_6$ alkyl, morpholinyl C$_1$-C$_6$ alkyl, thiomorpholinyl, thiomorpholinyl S,S-dioxide, thiomorpholinyl S-oxide, piperidinyl C$_1$-C$_6$ alkyl, pyrrolidinyl C$_1$-C$_6$ alkyl, imidazolidinyl C$_1$-C$_6$ alkyl, C$_3$-C$_8$ cycloalkyl, C$_3$-C$_8$ cycloalkyl C$_1$-C$_6$ alkyl, phenyl C$_1$-C$_6$ alkyl, and pyridyl C$_1$-C$_6$ alkyl, pyridazyl C$_1$-C$_6$ alkyl, pyrimidyl C$_1$-C$_6$ alkyl, pyrazinyl C$_1$-C$_6$ alkyl, thienyl C$_1$-C$_6$ alkyl, and furyl C$_1$-C$_6$ alkyl, wherein each of the above is unsubstituted or substituted with 1, 2, 3, or 4 R$_6$ groups; or R$_8$ and R$_9$ and the nitrogen to which they are attached form a 5, 6 or 7 membered heterocycloalkyl ring, which is unsubstituted or substituted with 1, 2, or 3 groups that are independently C$_1$-C$_6$ alkyl, C$_1$-C$_6$ alkoxy, hydroxy, or halogen; or R$_7$, R$_8$, and the nitrogens to which they are attached form a 5, 6, or 7 membered heterocycloalkyl group that is unsubstituted or substituted with 1, 2 or 3 groups that are independently C$_1$-C$_6$ alkyl, C$_1$-C$_6$ alkoxy, hydroxy, or halogen; wherein each of the above is unsubstituted or substituted with 1, 2, 3, or 4 R$_6$ groups; wherein R$_6$ at each occurrence is independently selected from the group consisting of halogen, hydroxy, NO$_2$, C$_1$-C$_6$ alkyl, C$_1$-C$_6$ alkoxy, CF$_3$, and OCF$_3$; and R$_5$ is —M—G—A, wherein M is phenyl, which is substituted with 1, 2, or 3 groups that are independently selected from the group consisting of F, Cl, Br, C$_1$-C$_4$ alkyl, hydroxy, methoxy, ethoxy, isopropoxy, CF$_3$, OCF$_3$, halo C$_1$-C$_4$ alkyl, halo C$_1$-C$_4$ alkoxy, and hydroxy C$_1$-C$_4$ alkyl;

G is selected from a direct bond between M and A, and O; and

A is selected from the group consisting of phenyl, naphthyl, tetrahydronaphthyl, and dihydronaphthyl, wherein each is unsubstituted or substituted with 1, 2, or 3 groups that are independently selected from the group consisting of F, Cl, Br, C$_1$-C$_4$ alkyl, C$_1$-C$_4$ alkoxy, halo C$_1$-C$_4$ alkyl, CF$_3$, OCF$_3$, CN, and NO$_2$.

24. A compound or pharmaceutically acceptable salt thereof of structural formula VIII:

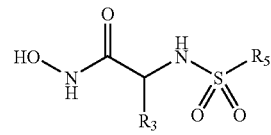

VIII wherein R$_3$ is selected from:

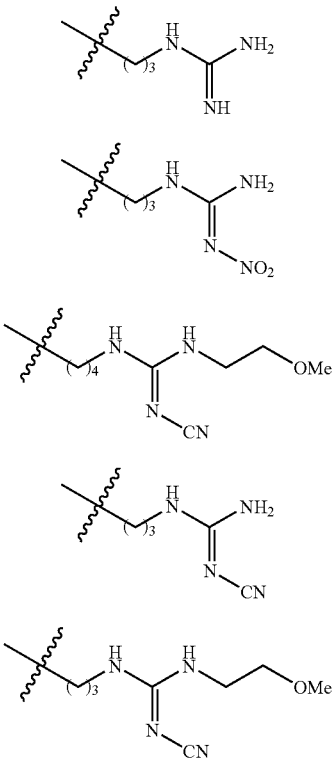

| 95 | 96 |
|---|---|
| -continued | -continued |
| 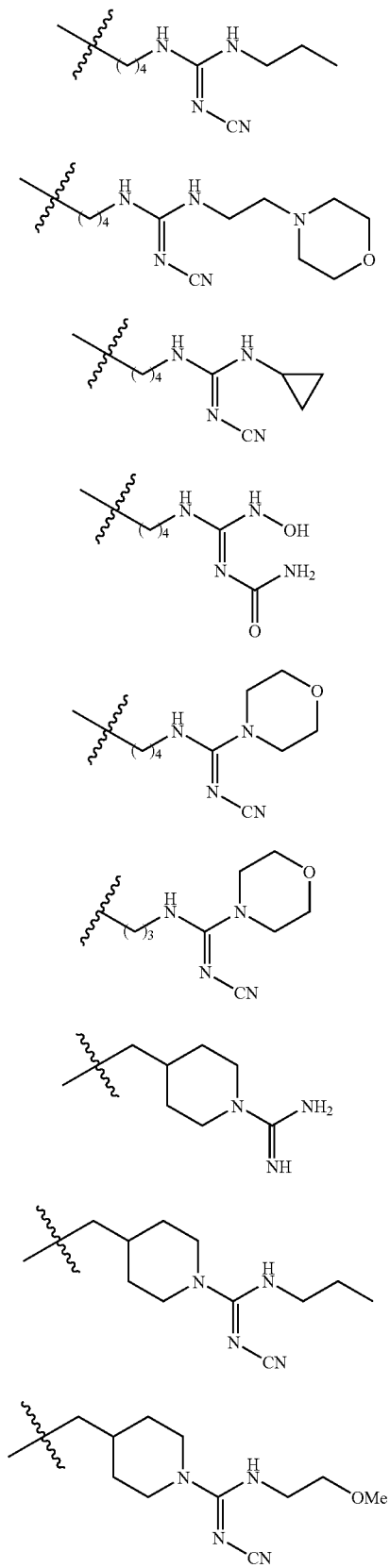 | 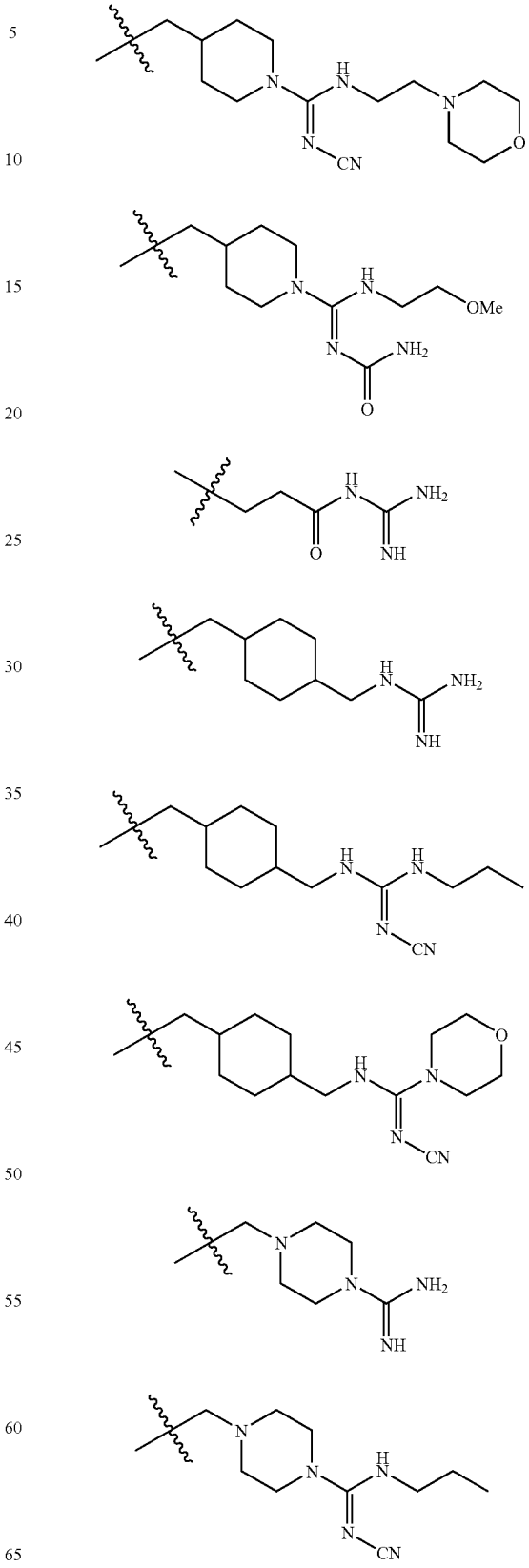 |

-continued
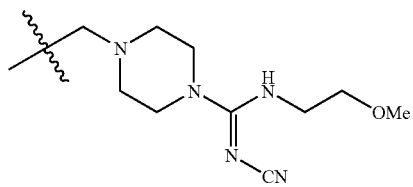
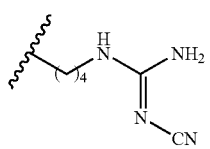
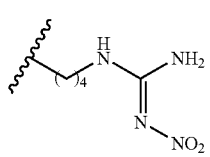
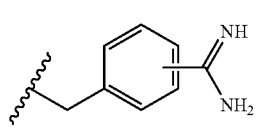
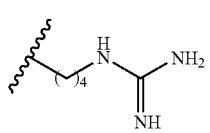
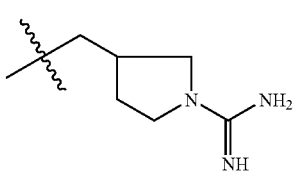
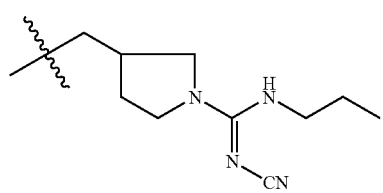
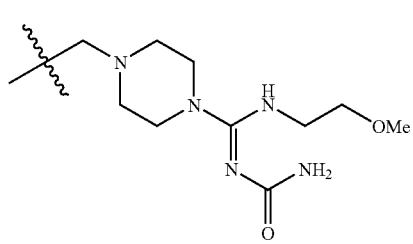
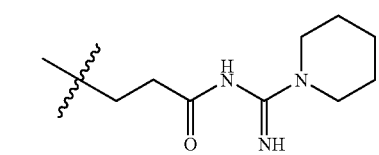
-continued
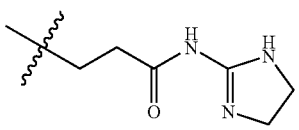
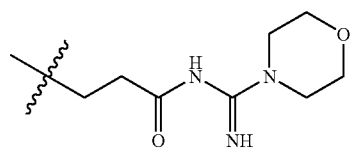
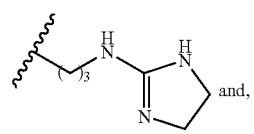 and,
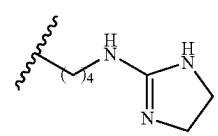
and $R_5$ is selected from:
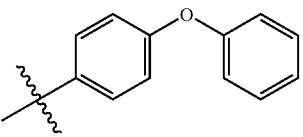
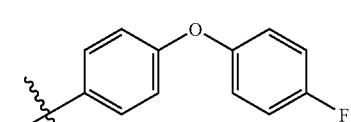
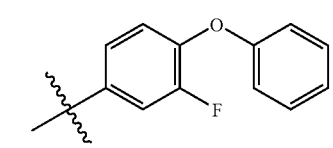
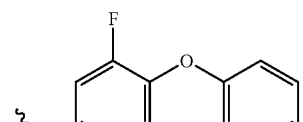
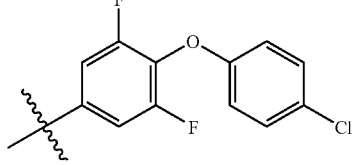

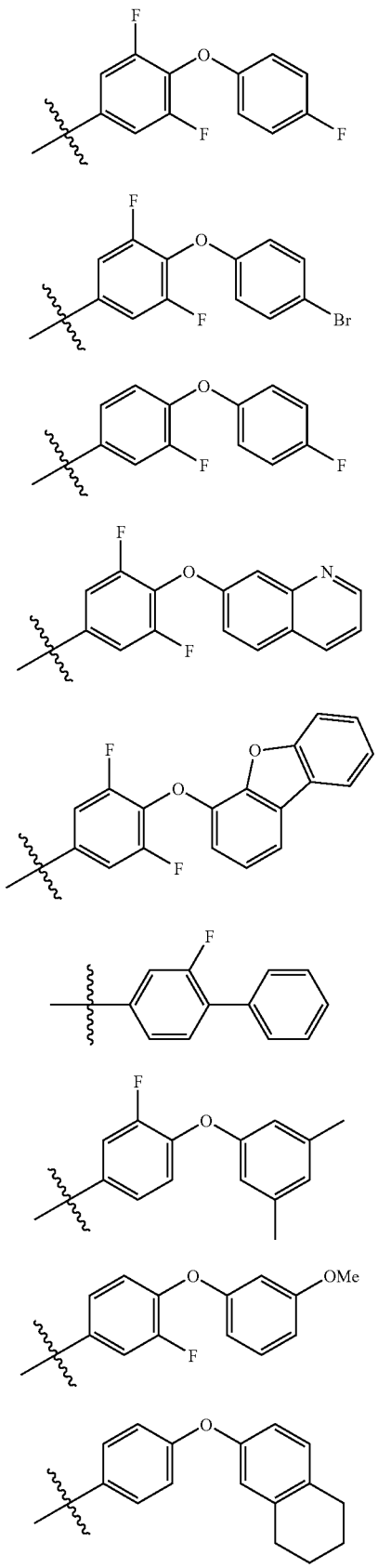
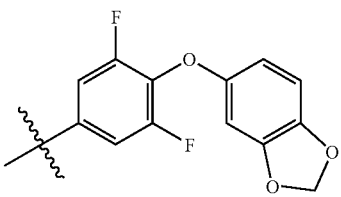
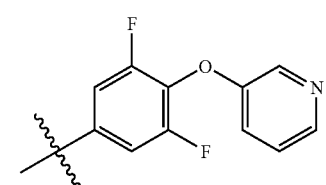
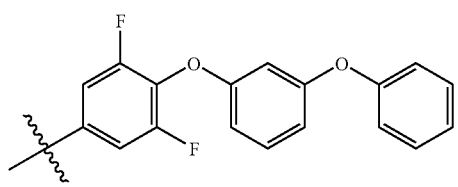
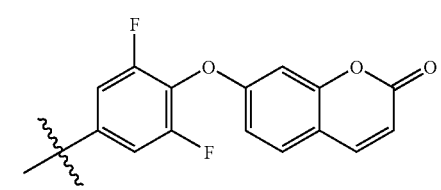
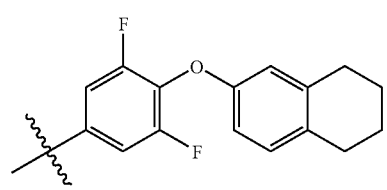
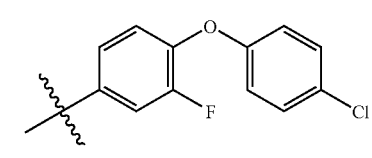
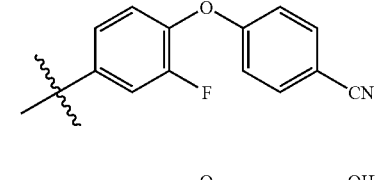
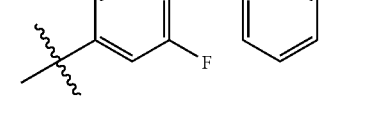
and -continued

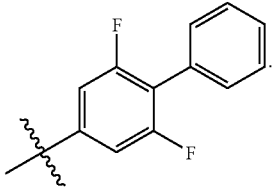

25. A compound or pharmaceutically acceptable salt thereof listed in the following table:

| 2 | $N^1$-hydroxy-$N^2$-[(4-phenoxyphenyl)sulfonyl]-D-argininamide |
|---|---|
| 3 | $N^2$-{[4-(4-fluorophenoxy)phenyl]sulfonyl}-$N^1$-hydroxy-D-argininamide |
| 4 | $N^2$-[(3-fluoro-4-phenoxyphenyl)sulfonyl]-$N^1$-hydroxy-D-argininamide |
| 5 | $N^2$-[(3,5-difluoro-4-phenoxyphenyl)sulfonyl]-$N^1$-hydroxy-D-argininamide |
| 6 | $N^2$-{[4-(4-chlorophenoxy)-3,5-difluorophenyl]sulfonyl}-$N^1$-hydroxy-D-argininamide |
| 7 | $N^2$-{[3,5-difluoro-4-(4-fluorophenoxy)phenyl]sulfonyl}-$N^1$-hydroxy-D-argininamide |
| 8 | $N^2$-{[4-(4-bromophenoxy)-3,5-difluorophenyl]sulfonyl}-$N^1$-hydroxy-D-argininamide |
| 9 | $N^2$-{[3-fluoro-4-(4-fluorophenoxy)phenyl]sulfonyl}-$N^1$-hydroxy-D-argininamide |
| 10 | $N^2$-{[4-(4-chlorophenoxy)-3-fluorophenyl]sulfonyl}-$N^1$-hydroxy-D-argininamide |
| 11 | $N^2$-{[4-(4-cyanophenoxy)-3-fluorophenyl]sulfonyl}-$N^1$-hydroxy-D-argininamide |
| 12 | $N^2$-{[4-(3,5-dimethylphenoxy)-3-fluorophenyl]sulfonyl}-$N^1$-hydroxy-D-argininamide |
| 14 | $N^1$-hydroxy-$N^2$-{[6-(5,6,7,8-tetrahydronaphthalen-2-yloxy)pyridin-3-yl]sulfonyl}-D-argininamide |
| 16 | $N^5$-[(Z)-amino(nitroimino)methyl]-$N^1$-hydroxy-$N^2$-[(4-phenoxyphenyl)sulfonyl]-D-ornithinamide |
| 18 | $N^6$-[(E)-amino(cyanoimino)methyl]-$N^1$-hydroxy-$N^2$-[(4-phenoxyphenyl)sulfonyl]-D-lysinamide |
| 20 | $N^6$-{(Z)-(cyanoimino)[(2-methoxyethyl)amino]methyl}-$N^1$-hydroxy-$N^2$-[(4-phenoxyphenyl) sulfonyl]-D-lysinamide |
| 21 | $N^6$-{(Z)-(cyanoimino)[(2-methoxyethyl)amino]methyl}-$N^2$-{[4-(4-fluorophenoxy)phenyl] sulfonyl}-$N^1$-hydroxy-D-lysinamide |
| 23 | $N^6$-[(E)-(cyanoimino)(propylamino)methyl]-$N^1$-hydroxy-$N^2$-[(4-phenoxyphenyl)sulfonyl]-D-lysinamide |
| 24 | $N^6$-[(E)-(cyanoimino)(propylamino)methyl]-$N^2$-{[4-(4-fluorophenoxy)phenyl]sulfonyl}-$N^1$-hydroxy-D-lysinamide |
| 26 | $N^6$-{(Z)-(cyanoimino)[(2-morpholin-4-ylethyl)amino]methyl}-$N^1$-hydroxy-$N^2$-[(4-phenoxyphenyl) sulfonyl]-D-lysinamide |
| 27 | $N^6$-[(Z)-(cyanoimino)(cyclopropylamino)methyl]-$N^1$-hydroxy-$N^2$-[(4-phenoxyphenyl) sulfonyl]-D-lysinamide |
| 28 | $N^6$-[(E)-[(aminocarbonyl)imino](hydroxyamino)methyl]-$N^2$-{[4-(4-fluorophenoxy)phenyl] sulfonyl}-$N^1$-hydroxy-D-lysinamide |
| 37 | $N^6$-[(E)-(cyanoimino)(morpholin-4-yl)methyl]-$N^2$-{[4-(4-fluorophenoxy)phenyl]sulfonyl}-$N^1$-hydroxy-D-lysinamide |
| 38 | $N^6$-[(Z)-(cyanoimino)(morpholin-4-yl)methyl]-$N^2$-{[3-fluoro-4-(4-fluorophenoxy)phenyl] sulfonyl}-$N^1$-hydroxy-D-lysinamide |
| 39 | 3-{1-[amino(imino)methyl]piperidin-4-yl}-$N^1$-hydroxy-$N^2$-[(4-phenoxyphenyl)sulfonyl]alaninamide |
| 40 | 3-{1-[(Z)-(cyanoimino)(propylamino)methyl]piperidin-4-yl}-$N^1$-hydroxy-$N^2$-[(4-phenoxyphenyl)sulfonyl]alaninamide |
| 41 | 3-(1-{(Z)-(cyanoimino)[(2-methoxyethyl)amino]methyl}piperidin-4-yl)-$N^1$-hydroxy-$N^2$-[(4-phenoxyphenyl)sulfonyl]alaninamide |
| 42 | 3-(1-{(E)-(cyanoimino)[(2-methoxyethyl)amino]methyl}piperidin-4-yl)-$N^2$-{[3,5-difluoro-4-(4-fluorophenoxy)phenyl]sulfonyl}-$N^1$-hydroxyalaninamide |
| 43 | 3-(1-{(Z)-[(aminocarbonyl)imino][(2-methoxyethyl)amino]methyl}piperidin-4-yl)-$N^1$-hydroxy-$N^2$-[(4-phenoxyphenyl)sulfonyl]alaninamide |
| 48 | $N^6$-4,5-dihydro-1H-imidazol-2-yl-$N^2$-{[4-(4-fluorophenoxy)phenyl]sulfonyl}-$N^1$-hydroxy-D-lysinamide |
| 55 | $N^1$-hydroxy-$N^2$-{[4-(phenyloxy)phenyl]sulfonyl}-D-histidinamide |
| 62 | $N^1$-hydroxy-$N^2$-{[6-(naphthalen-1-yloxy)pyridin-3-yl]sulfonyl}-D-argininamide |
| 64 | $N^6$-[(E)-(cyanoimino)(hydroxyamino)methyl)]-$N^2$-({4-[(4-fluorophenyl)oxy]phenyl}sulfonyl)-$N^1$-hydroxy-D-lysinamide |
| 74 | $N^2$-({3,5-difluoro-4-[(4-hydroxyphenyl)oxy]phenyl}sulfonyl)-$N^1$-hydroxyargininamide |
| 75 | $N^2$-{[3,5-difluoro-4-(pyridin-3-yloxy)phenyl]sulfonyl}-$N^1$-hydroxyargininamide |
| 78 | $N^2$-{[3,5-difluoro-4-({4-[(phenylmethyl)oxy]phenyl}oxy)phenyl]sulfonyl}-$N^1$-hydroxyargininamide |
| 81 | $N^2$-({3,5-difluoro-4-[(4-fluorophenyl)oxy]phenyl}sulfonyl)-$N^1$-hydroxy-4-[(hydroxyamino)(imino)methyl]-D-phenylalaninamide |
| 82 | $N^2$-({3,5-difluoro-4-[(4-fluorophenyl)oxy]phenyl}sulfonyl)-$N^1$-hydroxy-3-[(hydroxyamino)(imino)methyl]-D-phenylalaninamide |
| 84 | $N^2$-({3,5-difluoro-4-[(4-fluorophenyl)oxy]phenyl}sulfonyl)-$N^1$-hydroxy-3-[1-(morpholin-4-ylcarbonyl)piperidin-4-yl]alaninamide |
| 85 | 3-[amino(imino)methyl]-$N^2$-({3,5-difluoro-4-[(4-fluorophenyl)oxy]phenyl}sulfonyl)-$N^1$-hydroxy-D-phenylalaninamide |
| 86 | 4-[amino(imino)methyl]-$N^2$-({3,5-difluoro-4-[(4-fluorophenyl)oxy]phenyl}sulfonyl)-$N^1$-hydroxy-D-phenylalaninamide |
| 92 | (2R)-4-{[amino(imino)methyl]amino}-$N^2$-[({4-[(4-chlorophenyl)oxy]-3,5-difluorophenyl}sulfonyl)amino]-$N^1$-hydroxybutanamide. |

26. A pharmaceutical composition comprising a compound according to claim 1 and a pharmaceutically acceptable carrier.

27. A method of treating breast cancer, arthritis, and stroke comprising administering to a mammal in need of such treatment a therapeutically effective amount of a pharmaceutical composition according to claim 26.

* * * * *

UNITED STATES PATENT AND TRADEMARK OFFICE
CERTIFICATE OF CORRECTION

PATENT NO. : 7,498,358 B2 Page 1 of 1
APPLICATION NO. : 10/498338
DATED : March 3, 2009
INVENTOR(S) : S. Brown et al.

It is certified that error appears in the above-identified patent and that said Letters Patent is hereby corrected as shown below:

On the cover page, item

[*] Notice:   Subject to any disclaimer, the term of this patent is extended or adjusted under 35 USC 154(b) by 391 days Delete the phrase "by 391 days" and insert -- by 621 days --

Signed and Sealed this

Eleventh Day of August, 2009

David J. Kappos
*Director of the United States Patent and Trademark Office*